(12) United States Patent
Van Der Horst

(10) Patent No.: US 8,834,875 B2
(45) Date of Patent: *Sep. 16, 2014

(54) NOTCH1 BINDING AGENTS AND METHODS OF USE THEREOF

(75) Inventor: Edward Thein Htun Van Der Horst, Palo Alto, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/005,966

(22) Filed: Jan. 13, 2011

(65) Prior Publication Data

US 2012/0213786 A1   Aug. 23, 2012

Related U.S. Application Data

(60) Provisional application No. 61/294,762, filed on Jan. 13, 2010, provisional application No. 61/410,651, filed on Nov. 5, 2010.

(51) Int. Cl.
*A61K 39/395* (2006.01)
*A61P 35/02* (2006.01)
*C07K 16/30* (2006.01)
*C07K 16/28* (2006.01)
*A61K 39/00* (2006.01)

(52) U.S. Cl.
CPC ............ *C07K 16/28* (2013.01); *C07K 2317/92* (2013.01); *C07K 2317/76* (2013.01); *C07K 2317/565* (2013.01); *A61K 2039/505* (2013.01); *C07K 2317/24* (2013.01); *C07K 2317/73* (2013.01)
USPC .................. 424/133.1; 424/155.1; 424/136.1; 424/174.1; 530/387.3; 530/387.7

(58) Field of Classification Search
None
See application file for complete search history.

(56) References Cited

U.S. PATENT DOCUMENTS

| | | | |
|---|---|---|---|
| 5,648,464 A | 7/1997 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,854,027 A | 12/1998 | Steipe et al. |
| 6,004,528 A | 12/1999 | Bergstein |
| 6,080,588 A | 6/2000 | Glick |
| 6,083,904 A | 7/2000 | Artavanis-Tsakonas |
| 6,090,922 A | 7/2000 | Artavanis-Tsakonas et al. |
| 6,180,370 B1 | 1/2001 | Queen et al. |
| 6,379,925 B1 | 4/2002 | Kitajewski et al. |
| 6,537,775 B1 | 3/2003 | Tournier-Lasserve et al. |
| 6,689,744 B2 | 2/2004 | Gao et al. |
| 6,692,919 B1 | 2/2004 | Artavanis-Tsakonas et al. |
| 6,984,522 B2 | 1/2006 | Clarke et al. |
| 7,115,360 B2 | 10/2006 | Clarke et al. |
| 7,282,203 B2 | 10/2007 | Coignet |
| 7,632,926 B2 | 12/2009 | Kim et al. |
| 7,713,710 B2 | 5/2010 | Clarke et al. |
| 7,754,206 B2 | 7/2010 | Clarke et al. |
| 7,850,961 B2 | 12/2010 | Clarke et al. |
| 8,088,617 B2 | 1/2012 | Gurney et al. |
| 8,206,713 B2 | 6/2012 | Lewicki et al. |
| 8,404,237 B2 | 3/2013 | Lewicki et al. |
| 8,435,513 B2 | 5/2013 | Gurney et al. |
| 2002/0086014 A1 | 7/2002 | Korman et al. |
| 2002/0119565 A1 | 8/2002 | Clarke et al. |
| 2002/0122802 A1 | 9/2002 | Wands et al. |
| 2003/0082651 A1 | 5/2003 | Gao et al. |
| 2003/0083465 A1 | 5/2003 | Zimrin et al. |
| 2003/0186290 A1 | 10/2003 | Tournier-Lasserve et al. |
| 2004/0229301 A1 | 11/2004 | Wang |
| 2005/0026831 A1 | 2/2005 | Bodmer et al. |
| 2005/0089518 A1 | 4/2005 | Clarke et al. |
| 2005/0112121 A1 | 5/2005 | Artavanis-Tsakonas et al. |
| 2005/0142635 A1 | 6/2005 | Tsuchiya et al. |
| 2005/0187179 A1 | 8/2005 | Miele et al. |
| 2005/0232927 A1 | 10/2005 | Clarke et al. |
| 2006/0030694 A1 | 2/2006 | Kitajewski et al. |
| 2006/0051325 A1 | 3/2006 | Clarke et al. |
| 2006/0073125 A1 | 4/2006 | Clarke et al. |
| 2006/0083682 A1 | 4/2006 | Bergstein |

(Continued)

FOREIGN PATENT DOCUMENTS

DE    4425115 A1    1/1996
EP    0662827 B2    7/1995

(Continued)

OTHER PUBLICATIONS

Bendig, Humanization of rodent monoclonal antibodies by CDR grafting, 1995, Methods: A companion to methods in enzymology, vol. 8, p. 83-93.*

(Continued)

*Primary Examiner* — Hong Sang
*Assistant Examiner* — Michael D Allen
(74) *Attorney, Agent, or Firm* — Sterne, Kessler, Goldstein & Fox P.L.L.C.

(57) ABSTRACT

The present invention relates to Notch1 binding agents and methods of using the agents for treating diseases, such as hematologic cancers. The present invention provides antibodies that specifically bind to a non-ligand binding membrane proximal region of the extracellular domain of human Notch1. The present invention further provides methods of using agents that inhibit Notch1 activity for treating cancer. Also described are methods of treating hematologic cancers comprising administering a therapeutically effective amount of a binding agent or antibody of the present invention to a subject having a hematologic cancer such as T-cell lymphoblastic leukemia.

11 Claims, 8 Drawing Sheets

(56) References Cited

U.S. PATENT DOCUMENTS

| | | |
|---|---|---|
| 2006/0263774 A1 | 11/2006 | Clark et al. |
| 2007/0036800 A1 | 2/2007 | Bergstein |
| 2007/0036801 A1 | 2/2007 | Bergstein |
| 2007/0036804 A1 | 2/2007 | Bergstein |
| 2007/0041984 A1 | 2/2007 | Bergstein |
| 2007/0196047 A9 | 8/2007 | Levner et al. |
| 2007/0212737 A1 | 9/2007 | Clarke et al. |
| 2007/0265246 A1 | 11/2007 | Clevers et al. |
| 2008/0076670 A1 | 3/2008 | Sivan et al. |
| 2008/0112940 A1 | 5/2008 | Liaw |
| 2008/0118520 A1 | 5/2008 | Li et al. |
| 2008/0131434 A1* | 6/2008 | Lewicki et al. ............ 424/138.1 |
| 2008/0131908 A1 | 6/2008 | Li et al. |
| 2008/0132423 A1 | 6/2008 | Kondo |
| 2008/0178305 A1 | 7/2008 | Clarke et al. |
| 2008/0187532 A1 | 8/2008 | Gurney et al. |
| 2008/0188405 A1 | 8/2008 | Di Fiore et al. |
| 2008/0194022 A1 | 8/2008 | Clarke et al. |
| 2008/0226621 A1 | 9/2008 | Fung et al. |
| 2008/0260734 A1 | 10/2008 | Clarke et al. |
| 2009/0004205 A1 | 1/2009 | Clarke et al. |
| 2009/0028856 A1 | 1/2009 | Chen et al. |
| 2009/0047285 A1 | 2/2009 | Gurney et al. |
| 2009/0081238 A1 | 3/2009 | Siebel et al. |
| 2009/0208491 A1 | 8/2009 | Gurney et al. |
| 2010/0111958 A1 | 5/2010 | Gurney et al. |
| 2011/0033481 A1 | 2/2011 | Clarke et al. |
| 2011/0092378 A1 | 4/2011 | Clarke et al. |
| 2011/0195065 A1 | 8/2011 | Lewicki et al. |
| 2011/0311552 A1* | 12/2011 | Gurney et al. ............ 424/172.1 |
| 2012/0308558 A1 | 12/2012 | Gurney et al. |

FOREIGN PATENT DOCUMENTS

| | | |
|---|---|---|
| JP | 2002-526109 A | 8/2002 |
| WO | WO 94/07474 A1 | 4/1994 |
| WO | WO 97/37004 A1 | 10/1997 |
| WO | WO 97/45143 A1 | 12/1997 |
| WO | WO 98/57621 A1 | 12/1998 |
| WO | WO 00/20576 A2 | 4/2000 |
| WO | WO 00/52143 A2 | 9/2000 |
| WO | WO 02/00576 A1 | 1/2002 |
| WO | WO 02/12447 A2 | 2/2002 |
| WO | WO 02/18544 A2 | 3/2002 |
| WO | WO 03/042246 A2 | 5/2003 |
| WO | WO 03/050502 A2 | 6/2003 |
| WO | WO 03/062273 A2 | 7/2003 |
| WO | WO 2004/001004 A2 | 12/2003 |
| WO | WO 2004/052389 A2 | 6/2004 |
| WO | WO 2004/091383 A2 | 10/2004 |
| WO | WO 2004/094475 A2 | 11/2004 |
| WO | WO 2005/026334 A2 | 3/2005 |
| WO | WO 2005/054434 A2 | 6/2005 |
| WO | WO 2005/074633 A2 | 8/2005 |
| WO | WO 2006/110581 A2 | 10/2006 |
| WO | WO 2007/145840 A2 | 12/2007 |
| WO | WO 2008/051797 A3 | 5/2008 |
| WO | WO 2008/057144 A2 | 5/2008 |
| WO | WO 2008/076960 A2 | 6/2008 |
| WO | WO 2008/091641 A2 | 7/2008 |
| WO | WO 2008/108910 A2 | 9/2008 |
| WO | WO 2008/136848 A2 | 11/2008 |
| WO | WO 2008/150525 A1 | 12/2008 |
| WO | WO 2009/025867 A2 | 2/2009 |
| WO | WO 2009/035522 A1 | 3/2009 |
| WO | WO 2010/005567 A2 | 1/2010 |

OTHER PUBLICATIONS

Casset et Al., A peptide mimetic of an anti-CD4 monoclonal antibody by rational design, 2003, Biochemical and Biophysical Research Communications, vol. 307, p. 198-205.*

Colman, Effects of amino acid sequence changes on antibody-antigen interactions, 55th Forum in Immunology, p. 33-36.*

Greenspan et Al., Defining epitopes: It's not as easy as it seems, 1999, Nature Biotechnology, vol. 17, p. 936-937.*

MacCallum et Al., Antibody-antigen interactions: Contact analysis and binding site topograph, 1996, Journal of Molecular biology, vol. 262, p. 732-745.*

Panka et Al., Variable region framework differences result in decreased or increased affinity of variant anti-digoxin antibodies, 1988, Proceedings of the National Academy of Sciences, USA, vol. 85, p. 3080-3084.*

Paul, Fundamental Immunology, Third Edition, 1993, p. 292-295.*

Rudikoff et Al., Single amino acid substitution altering antigen-binding specificity, 1982, Proceedings of the National Academy of Sciences, USA, vol. 79, p. 1979-1983.*

Real, Leukemia, vol. 23, p. 1374-1377, 2009.*

Al-Hajj, M., et al., "Prospective identification of tumorigenic breast cancer cells," *PNAS* 100(7):3983-3988, Proceedings of the National Academy of Science, United States (Apr. 1, 2003).

Arias, A.M., et al., "CSL-independent Notch signalling: a checkpoint in cell fate decisions during development?," *Current Opinion In Genetics & Development* 12:524-533, Elsevier Science, Ltd., England, (2002).

Artavanis-Tsakonas, S., et al., "Notch Signalling: Cell Fate Control and Signal Integration in Development," *Science* 284:770-776, American Association for the Advancement of Science, United States (Apr. 30, 1999).

Brennan, K. and Brown, A.M.C., "Is there a role for Notch signalling in human breast cancer?," *Breast Cancer Research* 5:69-75, BioMed Central Ltd., England (Jan. 20, 2003).

Brennan, K., et al., "Repression by Notch is required before Wingless signalling during muscle progenitor cell development in *Drosophila,*" *Current Biology* 9:707-710, Current Biology Publications, England (Jun. 21, 1999).

Cole, S.P.C., et al., "The EBV-hybridoma technique and its application to human lung cancer," *Monoclonal Antibodies and Cancer Therapy* 77-96, Alan R. Liss, Inc., United States (1985).

Del Amo, F.F., et al., "Cloning, Analysis, and Chromosomal Localization of *Notch-1,* a Mouse Homolog of *Drospholia Notch"* *Genomics* 15:259-264, Academic Press, Inc., United States (1993).

Domenga, V., et al., "*Notch3* is required for arterial identity and maturation of vascular smooth muscle cells," *Genes & Development* 18:2730-2735, Cold Spring Harbor Laboratory Press, United States (2004).

Duncan, A.W., et al., "Integration of Notch and Wnt signaling in hematopoietic stem cell maintenance," *Nature Immunology* 6(3):314-322, Nature Publishing Group, United States (Mar. 2005; Epub Jan. 23, 2005).

Ellisen, L.W., et al., "*TAN-1,* The Human Homolog of the *Drosophila Notch* Gene , Is Broken by Chromosomal Translocations in T Lymphoblastic Neoplasms," *Cell* 66:649-661, Cell Press, United States (Aug. 23, 1991).

Gale, N.W., et al., "Haploinsufficiency of delta-like 4 ligand results in embryonic lethality due to major defects in arterial and vascular development," *PNAS* 101(45):15949-15954, National Academy of Science, United States (Nov. 9, 2004).

Gallahan, D., et al., "Expression of a Truncated *Int3* Gene in Developing Secretory Mammary Epithelium Specifically Retards Lobular Differentiation Resulting in Tumorigenesis," *Cancer Research* 56:1775-1785, American Association for Cancer Research, United States (Apr. 15, 1996).

Gridley, T., "Notch signaling and inherited disease syndromes," *Human Molecular Genetics* 12(R1):R9-R13, Oxford University Press, England (2003).

Gridley, T., "Notch signaling during vascular development," *PNAS* 98(10):5377-5378, National Academy of Sciences, United States (May 8, 2001).

Gridley, T., "Vessel guidance," *Nature* 445:722-723, Nature Publishing Group, United States (Feb. 15, 2007).

Gridley, T., "Notch Signaling in Vertebrate Development and Disease," *Mol. Cell. Neurosci, 9:*103-108, Academic Press, United States (1997).

Hadland, B.K., et al., "A requirement for Notch1 distinguishes 2 phases of definitive hematopoiesis during development," *Blood*

(56) References Cited

OTHER PUBLICATIONS

*104*:3097-3105, The American Society of Hematology, United States (Nov. 15, 2004; Epub Jul. 13, 2004).

Hainaud, P., et al., "The Role of the Vascular Endothelial Growth Factor—Delta-like 4 Ligand/Notch4-Ephrin B2 Cascade in Tumor Vessel Remodeling and Endothelial Cell Functions," *Cancer Res.* 66(17):8501-8510, American Association for Cancer Research, United States (Sep. 1, 2006).

Hallahan, A.R., et al., "The SmoA1 Mouse Model Reveals That Notch Signaling Is Critical for the Growth and Survival of Sonic Hedgehog-Induced Medulloblastomas," *Cancer Research 64*:7794-7800, American Association for Cancer Research, United States (Nov. 1, 2004).

Hitoshi, S., et al., "Notch pathway molecules are essential for the maintenance, but not the generation, of mammalian neural stem cells," *Genes & Development* 16:846-, Cold Spring Harbor Laboratory Press, United States (2002).

Iso, T. et al., "Notch Signaling in Vascular Development," *Arterioscler. Thromb. Vasc. Biol.* 23:543-553, American Heart Association, Inc., United States (2003).

Jhappan, C., et al., "Expression of an activated *Notch*-related *int-3* transgene interferes with cell differentiation and induces neoplastic transformation in mammary and salivary glands," *Genes& Development* 6:345-355, Cold Spring Harbor Laboratory Press, United States (1992).

Joutel, A. and Tournier-Lasserve, E., "Notch signalling pathway and human diseases," *Seminars In Cell & Departmental Biology* 9:619-625, Academic Press, United States (1998).

Joutel, A., et al., "*Notch3* mutations in CADASIL, a hereditary adult-onset condition causing stroke and dementia," *Nature 383*(6602):707-710, Macmillan Magazines Ltd., England (Oct. 24, 1996).

Karanu, F.N., et al., "The Notch Ligand Jagged-1 Represents a Novel Growth Factor of Human Hematopoietic Stem Cells," *J. Exp. Med.* 192(9): 1365-1372, The Rockefeller University Press, United States (Nov. 6, 2000).

Kidd, S., et al., "Sequence of the Notch Locus of *Drosophila melanogaster*: Relationship of the Encoded Protein to Mammalian Clotting and Growth Factors," *Molecular and Cellular Biology 6*(9):3094-3108, American Society for Microbiology, United States (Sep. 1986).

Kopper, L. and Hajdú, M., "Tumor Stem Cells," *Pathology Oncology Research 10*(2):69-73, Arányi Lajos Foundation, Hungary (2004).

Krebs, L.T., et al., "Notch signaling is essential for vascular morphogenesis in mice," *Genes & Development 14*:1343-1352, Cold Spring Harbor Laboratory Press, United States (2000).

Kuukasjärvi, T., et al., "Genetic Heterogeneity and Clonal Evolution Underlying Development of Asynchronous Metastasis in Human Breast Cancer," *Cancer Research 57*:1597-1604 American Association for Cancer Research, United States (Apr. 15, 1997).

Lapidot, T., et al., "A cell initiating acute myeloid leukaemia after transplantation into SCID mice," *Nature 367*:645-648, Macmillian Magazines Ltd., England (Feb. 17, 1994).

Lawrence, N., et al., "Notch signaling targets the Wingless responsiveness of a *Ubx* visceral mesoderm enhancer in *Drosophila*,"*Current Biology 11*(6):375-385, Cell Press, United States (Mar. 20, 2001).

Leethanakul et al., "Distinct Pattern of Expression of Differentiation and Growth-Related Genes in Squamous Cell Carcinomas of the Head and Neck Revealed by the Use of Laser Capture Microdissection and Cdna Arrays," *Oncogene 19*:3220-3224 (2000), Nature Publishing Group, Houndmills, Basingstoke, Hampshire RG21 6XS, UK.

Leong and Karsan, "Recent insights into the role of Notch signaling tumorigenesis," *Blood 107*:2223-2233 (2006), American Society of Hematology, United States.

Leong et al., "Activated Notch4 Inhibits Angiogenesis: Role of β1-Integrin Activartion," *Mol. Cell. Biol.* 22:2830-2841, (2002) American Society for Microbiology, United States.

McCright et al., "Defects In Development of the Kidney, Heart and Eye Vasculature in Mice Homozygous for a Hypomorphic Notch2 Mutation," *Development 128*:491-502 (2001), The Company of Biologists Limited Bidder Building, 140 Cowley Road, Cambridge CB4 ODL, UK.

Mohr, "Character Caused By Mutation of an Entire Region of a Chromosome in *Drosophila,*" *Genetics 4*:275-282 (1919), The Genetics Society of America, Genetics Mellon Institute, Box I 4400 Fifth Avenue Pittsburgh, Pennsylvania 15213-2683.

Parr et al., "The Possible Correlation of Notch-1 and Notch-2 with Clinical Outcome and Tumor Clinicpathological Parameters in Human Breast Cancer," *International Journal of Molecular Medicine 14*:779-786 (2004), Springer Verlag, Tiergartenstasse 17, 69121 Heidelberg, Germany.

Pear and Aster, "T Cell Acute Lymphoblastic Leukemia/Lymphoma: A Human Cancer Commonly Associated with Aberrant Notch1 Signaling," *Current Opinion in Hematology 11*:426-433 (2004), Lippincott Williams & Wilkins, Philadelphia, PA 19106.

Politi et al., "Notch in Mammary Gland Development and Breast Cancer," *Seminars in Cancer Biology 14*:341-347 (2004), Academic Press, 6277 Sea Harbor Drive, Orlando, FL, 32887-4900.

Purow et al., "Expression of Notch-1 and Its Ligands, Delta-Like-1 and Jagged-1, is Critical for Glioma Cell Survival and Proliferation," *Clinical Research 65*:2354-2363 (2005), American Association for Cancer Research, Philadelphia, PA 19106-4404.

Rae et al., "Novel Association of a Diverse Range of Genes with Renal Cell Carcinoma as Identified by Differential Display," *Inter. J. Cancer 88*:726-732 (2000), John Wiley & Sons Inc, 350 Main Street, Malden MA 02148, United States.

Rebay et al., "Specific Egf Repeats of Notch Mediate Interactions with Delta and Serrate: Implications for Notch as a Multifunctional Receptor," *Cell 67*:687-699 (1991), Cell Press, 50 Church Street, Cambridge, Massachusetts 02138.

Reya et al., "Stem Cells, Cancer and Cancer Stem Cells ," *Nature 414*:105-111 (2001), Nature Publishing Group, New York, NY 10013-1917, USA.

Robey et al., "An Activated Form of Notch Influences the Choice Between Cd4 and Cd8 T Cell Lineages," *Cell 87*:483-492 (1996), Cell Press, 50 Church Street, Cambridge, Massachusetts 02138.

Smith et al., "Constitutive Expression of a Truncated Int3 Gene in Mouse Mammary Epithelium Impairs Differentiation and Functional Development," *Cell Growth & Differentiation 6*: 563-577 (1995), American Association for Cancer Research, Philadelphia, PA 19106-4404.

Soriano et al., "Expression of an Activated Notch4(Int-3) Oncoprotein Disrupts Morphogenesis and Induces an Invasive Phenotype in Mammary Epithelial Cells in Vitro," *Intl. J. Cancer 86*: 652-659 (2000), John Wiley & Sons Inc, 350 Main Street, Malden MA 02148, USA.

Suzuki et al., "Imbalanced Expression of Tan-L and Human Notch4 in Endometrial Cancers," *International Journal of Oncology 17*: 1131-1139 (2000), Spandidos-publications, Athens 116 10, Greece.

Swiatek et al., "Notch1 is essential for postimplantation development in mice," *Genes & Development 8*:707-719, (1994) Cold Spring Harbor Laboratory.

Takeshita et al., "Critical Role of Endothelial Notch1 Signaling in Postnatal Angiogenesis," *Cir. Res. 100*:70-78 (2007), American Heart Association, Inc.

Tavares et al., "Inhibition of Vascular Endothelium by the Notch-Ligand Delta-4 Unveils a Novel Therapeutic Target," Vascular Wall Biology, Poster Board #-Session: 115-II, Abstract# 1944, pp. 531a, (2003), American Society of Hematology, San Diego, California.

Uyttendaele et al., "Notch4 and Wnt-L Proteins Function to Regulate Branching Morphogenesis of Malnmary Epithelial Cells in an Opposing Fashion," *Developmental Biology 196*:204-217 (1998), Academic Press, Orlando, FL 32887•4900.

Van Es and Clevers, "Notch and Wnt Inhibitors as Potential New Drugs for Intestinal Neoplastic Disease," *Trends in Molecular Medicine 11*: 496-502 (2005), Elsevier, London, UK WC1X 8RR.

Van Limpt et al., "Sage Analysis of Neuroblastoma Reveals a High Expression of the Human Homologue of the *Drosophila* Delta Gene," *Medical and Pediatric Oncology 35*:554-558 (2000), Wiley-Liss, Inc, 605 Third Avenue, New York, NY 10158-0012.

(56) References Cited

OTHER PUBLICATIONS

Varnum-Finney et al., "Pluripotent, Cytokine-dependent, Hematopoietic Stem Cells are Immortalized by Constitutive Notch1 Signaling," *Nature Medicine* 6:1278-1281 (2000), Nature Publishing Group, New York, NY 10013-1917, USA.

Weijzen et al., "Activation of Notch-L Signaling Maintains the Neoplastic Phenotype in Human Ras-Transformed Cells," *Nature Medicine* 8:979-986 (2002), Nature Publishing Group, New York, NY 10013-1917, USA.

Wharton et al., "Nucleotide Sequence from the Neurogenic Locus Notch Implies a Gene Product that Shares Homology with Proteins Containing Egf-Like Repeats," *Cell* 43:567-581 (1985), Cell Press, 50 Church Street, Cambridge, Massachusetts 02138.

Xu et al., "Regions of *Drosophila* Notch that Contribute to Ligand Binding and the Modulatory Influence of Fringe," *The Journal of Biological Chemistry* 280:30158-30165 (2005), American Society for Biochemistry and Molecular Biology, Inc., 9650 Rockville Pike, Bethesda, MD 20814 U.S.A.

Xue et al., "Embryonic Lethality and Vascular Defects in Mice Lacking the Notch Ligand Jagged1," *Human Molecular Genetics* 8: 723-730 (1999), Oxford University Press, McLean, VA 22101-0850, USA.

Zagouras et al., "Alterations in Notch Signaling in Neoplastic Lesions of the Human Cervix," *PNAS* 92: 6414-6418 (1995), National Academy of Sciences, Washington, DC 20001.

Extended European Search Report issued in European Application No. EP 07 777 332.3, on Aug. 11, 2009 (10 pages).

Sakamoto, K., et al., "Distinct roles of EGF repeats for the Notch signaling system," *Experimental Cell Research* 2005, 281-291, 302(2), Elsevier, Orlando, FL, XP-004649921.

Shao, L., et al., "Fringe modifies O-fucose on mouse Notch1 at epidermal growth factor-like repeats with the ligand-binding site and the Abruptex region," *The Journal of Biological Chemistry* 2003, 7775-7782, 278 (10), American Society for Biochemistry and Molecular Biology, Bethesda, MD, XP-002538409.

Peters, N., et al., "CADASIL-associated Notch3 mutations have differential effects both on ligand binding and ligand-induced Notch3 receptor signaling through RBP-Jk," *Experimental Cell Research* 2004, 454-464, 299 (2), Elsevier, Orlando, FL, XP-004537012.

Pei, Z. and Baker, N., "Competition between Delta and the Abruptex domain of Notch," *BMC Dev. Biol.* 8:4, BioMed Central, England (2008).

Luo, B. et al., "Isolation and functional analysis of a cDNA for human Jagged2, a gene encoding a ligand for the Notch1 receptor," *Mol. Cell. Biol.* 17:6057-6067, American Society for Microbiology, United States (1997).

International Search Report for International Application No. PCT/US09/03994, ISA/US, Alexandria, Virginia, USA, mailed on Jul. 23, 2010.

Shimizu, K., et al., "Physical 1-15 interaction on Delta1, Jagged1, and Jagged2 with Notch1 and Notch3 receptors," *Biochem. Biophys. Res. Commun.* 276:385-389, Academic Press, United States (2000).

Rand, M., et al., "Calcium binding to tandem repeats of EGF-like modules. Expression and characterization of the EGF-like modules of human Notch-1 implicated in receptor-ligand interactions," *Protein Science* 6:2059-2071, Cambridge University Press, United Kingdom (1997).

Hambleton, S., et al., "Structural and Functional Properties of the Human Notch-1 Ligand Binding Region," *Structure* 12:2173-2183, Current Biology, Ltd., United States (2004).

Miele, L., Gamma-Secretase and Notch Signaling: Novel Therapeutic Targets in Breast Cancer, DTIC (Online), accessed at http://www.dtic.mil/cgi-bin/GetTRDoc?Location=U2&doc=GetTRDoc.pdf&AD=ADA446389 (retrieved on Jan. 12, 2010).

Bellavia, D., et al., "Constitutive activtion of NF-Kband T-cell leukemia/lymphoma in Notch3 transgenic mice," *EMBO J.* 19:3337-3348, Oxford University Press, United States (2000).

Callahan, R. & Raafat, A., "Notch Signaling in Mammary Gland Tumorigenesis," *Journal of Mammary Gland Biology and Neoplasia* 6:23-36, Plenum Publishing Corporation, United States (2001).

Campbell, A.M., "Monoclonal anitbody technology," vol. 13, pp. v-29, Elsevier Science Publishers B.V, The Netherlands, 1984.

Imatani, A. and Callahan, R., "Identification of a novel *Notch-4/INT-3* RNA species encoding an activated gene product in certain human tumor cell lines," *Oncogene* 19:223-231, Macmillan Publishers Ltd., England (2000).

International Search Report for International Application No. PCT/US2008/001948, USPTO, mailed on Oct. 15, 2008.

Jang, M.S., et al., "Notch signaling as target in multimodality cancer therapy," *Curr. Opin. Mol. Ther.* 2(1):55-65, Thomson Reuters (Scientific) Ltd., England (Feb. 2000).

Jarriault, S., et al., "Signaling downstream of activated mammalian Notch," *Nature* 377:355-358, Nature Publishing Group, England (1995).

Jehn, B.M., et al., "Cutting edge: protective effects of notch-1 on TCR-induced apoptosis," *J. Immunol.* 162:635-638, The American Association of Immunologists, United States (1999).

Jundt, F., et al., "Activated Notch1 signaling promotes tumor cell proliferation and survival in Hodgkin and anaplastic large cell lymphoma," *Blood* 99:3398-3403, The American Society of Hematology, United States (2002).

Lee, J-S, et al., "Intracisternal Type A Particle-Mediated Activation of the *Notch4/int3* Gene in a Mouse Mammary Tumor: Generation of Truncated *Notch4/int3* mRNAs by Retroviral Splicing Events." *J. Virol.* 73:5166-5171, American Society for Microbiology, United States (1999).

Lee, S-H, et al., "Mutational analysis of *Notch1*, 2, 3, and 4 genes in common solid cancers and acute leukemias," *APMIS* 115:1357-1363, The Authors Journal Compilation, United States (2007).

Li, K., et al., "Modulation of Notch Signaling by Antibodies Specific for the Extracellular Negative Regulatory Region of NOTCH3," *J. Biol. Chem.* 283:8046-8054, The American Society for Biochemistry and Molecular Biology, Inc., United States (2008).

Li, L., et al., "The Human Homolog of Rat *Jagged1* Expressed by Marrow Stroma Inhibits Differentiation of 32D Cells through Interaction with Notch1," *Immunity* 8:43-55, Cell Press, United States (1998).

Li, L., et al., "Cloning, Characterization, and the Complete 56.8-Kilobase DNA Sequence of the Human Notch4 Gene," *Genomics* 51:45-48, Academic Press, United States (1998).

Lindsell, C.E., et al., "Jagged: A Mammalian Ligand That Activates Notch1," *Cell* 80:909-917, Cell Press, United States (1995).

Liu, Z., et al., "Notch1 loss of heterozygosity causes vascular tumors and lethal hemorrhage in mice," *J. Clin. Invest.* 121(2):800-8, American Society for Clinical Investigation, United States (Feb. 2011; Epub Jan. 25, 2011).

Miele, L., & Osborne, B., "Arbiter of Differentiation and Death: Notch Signaling Meets Apoptosis," *J. Cell Physiol.* 181:393-409, Wiley-Liss, Inc., United States (1999).

Nam, Y., et al., "Notch signaling as a therapeutic target," *Curr. Opin. Chem. Biol.* 6:501-509, Elsevier Science Ltd., Holland (2002).

Pelegrin, A., et al., "[Immunotargeting of tumors: state of the art and prospects in 2000]," *Bull. Cancer* 87(11):777-91, John Libbey Eurotext, France (Nov. 2000) in the English language.

Pelegrin, A., et al., "[Immunotargeting of tumors: state of the art and prospects in 2000]," *Bull. Cancer* 87(11):777-91, John Libbey Eurotext, France (Nov. 2000) in the French language.

Sambandam, A., et al., "Notch signaling controls the generation and differentiation of early T lineage progenitors," *Nature Immunol.* 6:663-670, Nature Publishing Group, England (2005).

Soriano, J.V., et al., "Expression of an activated Notch(int-3) oncoprotein disrupts morphogenesis and induces and invasive phenotype in mammary epithelial cells in vitro," *Int. J. Cancer* 86: 652-659, Wiley-Liss, Inc., United States (2000).

Sugaya, K., et al., "Gene organization of human Notch4 and (CTG)n polymorphism in this human counterpart gene of mouse proto-oncogene *Int3*," *Gene* 189:235-244, Elsevier Science B.V., Holland (1997).

Summons to attend oral proceedings pursuant to Rule 115(1) EPC for European Patent Application 05722705.0-2402/1718767, European Patent Office, Germany, mailed on Feb. 9, 2011.

(56) References Cited

OTHER PUBLICATIONS

Thelu, J., et al., "Notch signaling is linked to epidermal cell differentiation level in basal cell carcinoma, psoriasis and wound healing," *BMC Dermatology* 2:7, BioMed Central, England (2002).
Van Es, J.H., et al., "Notch/γ-secretase inhibition turns proliferative cells in intestinal crypts and adenomas into goblet cells," *Nature* 435:959-963, Nature Publishing Group, England (2005).
Weng, A.P., and Aster, J.C., "Multiple niches for Notch in cancer: context is everything," *Curr. Opin. Genet. Dev.* 14(1):48-54, Elsevier, England (Feb. 2004).
Weng, A.P., et al., "Activation Mutations of *Notch1* in Human T Cell Acute Lymphoblastic Leukemia," *Science* 306:269-271, Nature Publishing Group, England (2004).
Weng, A.P., et al., "Growth Suppression of Pre-T Acute Lymphoblastic Leukemia Cells by Inhibition of Notch Signaling," *Mol. Cell Biol.* 23:655-644, American Society for Microbiology, United States (2003).
Axelson, H., "Notch signaling and cancer: emerging complexity," *Semin. Cancer Biol.* 14:317-319, Elsevier Ltd., England (2004).
Curry, C.L., et al., "Gamma secretase inhibitor blocks Notch activation and induces apoptosis in Kaposi's sarcoma tumor cells," *Oncogene* 24:6333-6344, Nature Publishing Group, England (2005).
Dontu, G., et al., "Role of Notch signaling in cell-fate determination of human mammary stem/progenitor cells," *Breast Cancer Res.* 6:R605-R615, BioMed Central Ltd., England (2004).
Duan, Z., et al., "A Novel Notch Protein, N2N, Targeted by Neutrophil Elastase and Implicated in Hereditary Neutropenia," *Mol. Cell. Biol.* 24(1):58-70, American Society for Microbiology, United States (2004).
Harper, J.A., et al., "Notch signaling in development and disease," *Clin. Genet.* 64:461-472, Blackwell Munksgaard, Denmark (2003).
Hopfer, O., et al., "The Notch pathway in ovarian carcinomas and adenomas," *Br. J. Cancer* 93:709-718, Cancer Research UK, England (2005).
Huang, E.Y., et al., "Surface Expression of Notch1 on Thymocytes: Correlation with the Double-Negative to Double-Positive Transition," *J. Immunol.* 171:2296-2304, The American Association of Immunologists, United States (2003).
Maillard, I., et al., "Mastermind critically regulates Notch-mediated lymphoid cell fate decisions," *Blood* 104:1696-1702, The American Society of Hematology, United States (2004).
Qin, J.-Z., et al., "p53-independent NOXA induction overcomes apoptotic resistance of malignant melanomas," *Mol. Cancer Ther.* 3(8):895-902, American Association for Cancer Research, Inc., United States (2004).
Santa Cruz Biotechnology, Inc., "Notch 2 (25-255): sc-5545 datasheet," downloaded on Dec. 2, 2009.
NCBI Entrez, GenBank Report, Accession No. P01724, Burstein, Y. and Schechter, I., Entry Date Jul. 21, 1986, last updated Nov. 4, 2008.
NCBI Entrez, GenBank Report, Accession No. Q8VDC9, Sembi, P., Entry Date Mar. 1, 2002, last updated Oct. 31, 2006.
International Search Report for International Application No. PCT/US11/21135, International Searching Authority, Alexandria, Virginia, USA, mailed on Jul. 20, 2011.
Written Opinion of the International Searching Authority for International Application No. PCT/US11/21135, International Searching Authority, Alexandria, Virginia, USA, mailed on Jul. 20, 2011.
Liu, H., et al., "Notch3 is Critical for Proper Angiogenesis and Mural Cell Investment," *Circ. Res.* 107(7):860-70, Lippincott Williams & Wilkins, United States (2010).
Bolos, V., et al., "Notch Signaling in Development and Cancer," *Endocrine Reviews* 28(3):339-363, The Endocrine Society, United States (2007).
Miele, L., et al., "Notch Signaling as Novel Cancer Therapeutic Target," *Curr. Cancer Drug Targets* 6(4):313-323, Bentham Science Publishers, Ltd., Netherlands (2006).
Tanaka, M., et al., "Asymmetric localization of Notch2 on the microvillous surface in choroid plexus epithelial cells," *Histochem. Cell Biol.* 127(4):449-56, Epub Jan. 12, 2007, Springer Verlag, Germany (2007).
Jurynczyk, M., et al., "Notch3 Inhibition in Myelin-Reactive T cells Down-Regulates Protein Kinase Cθ and Attenuates Experimental Autoimmune Encephalomyelitis," *J. Immunology*, 180(4):2634-40, The American Association of Immunologists Inc., United States (2008).
Bendig, M., "Humanization of rodent monoclonal antibodies by CDR grafting," *Methods: A companion to methods in Enzymology* 8:83-93, Academic Press, England (1995).
Casset, F., et al., "A peptide mimetic of an anti-CD4 monoclonal antibody by rational design," *Biochem Biophys Res Commun.* 307(1):198-205, Elsevier Science USA, (2003).
Colman, P.M., "Effects of amino acid sequence changes on antibody-antigen interactions," *Res. Immunol.* 145(1):33-6, Elsevier, France (1994).
Greenspan, N.S. and Di Cera, E., "Defining epitopes: It's not as easy as it seems," *Nat. Biotechnol.* 17(10):936-7, Nature America Publishing, United States (1999).
MacCallum, R.M., et al., "Antibody-antigen interactions: contact analysis and binding site topography," *J. Mol. Biol.* 262(5):732-45, Elsevier, England (1996).
Panka, D.J., et al., "Variable region framework differences result in decreased or increased affinity of variant anti-digoxin antibodies," *Proc. Natl. Acad. U S A.* 85(9):3080-4, National Academy of Sciences, United States (1988).
Paul, W.E., *Fundamental Immunology*, Third Edition, pp. 292-295, Raven Press, United States (1993).
Rudikoff, S., et al., "Single amino acid substitution altering antigen-binding specificity," *Proc. Natl. Acad. Sci. U S A.* 79(6):1979-83, National Academy of Sciences, United States (1982).
Sriuranpong, V., et al., "Notch signaling induces cell cycle arrest in small cell lung cancer cells," *Cancer Res.* 61(7):3200-5, American Association for Cancer Research, United States (2001).
De Pascalis, R., et al., "Grafting of "abbreviated"complementarity-determining regions containing specificity-determining regions containing specificity-determining residues essential for ligand contact to engineer a less immunogenic humanized monoclonal antibody," *J. Immunol.* 169(6):3076-84, American Association of Immunologists, United States (2002).
Vajdos, F.F., et al., "Comprehensive functional maps of the antigen-binding site of an anti-ErbB2 antibody obtained with shotgun scanning mutagenesis," *J. Mol. Biol.* 320(2):415-28, Elsevier, England (2002).
Holm, P., et al., "Functional mapping and single chain construction of the anti-cytokeratin 8 monoclonal antibody TS1," *Mol Immunol.* 44(6):1075-84, Pergamon Press, England (2007).
Chen, Y. et al., "Selection and Analysis of an Optimized Anti-VEGF Antibody: Crystal Structure of an Affinity-Matured Fab in Complex with Antigen," *J. Mol. Biol.* 293(4):865-81, Academic Press, England (1999).
Wu, H., et al., "Humanization of a Murine Monoclonal Antibody by Simultaneous Optimization of Framework and CDR Residues," *J. Mol. Biol.* 294(1):151-62, Elsevier, England (1999).
Talora, C., et al., "Specific down-modulation of Notch1 signaling in cervical cancer cells is required for sustained HPV-E6/E7 expression and late steps of malignant transformation," *Genes Dev.* 16(17):2252-63, Cold Spring Harbor Laboratory Press, United States (2002).
Ahmad, I., et al., "Involvement of Notch-1 in mammalian retinal neurogenesis: association of Notch-1 activity with both immature and terminally differentiated cells," *Mech. Dev.* 53(1):73-85, Elsevier, Ireland (1995).
Houde, C., et al., "Overexpression of the Notch ligand JAG2 in malignant plasma cells from multiple myeloma patients and cell lines," *Blood* 104(12):3697-704, American Society of Hematology, United States (2004).
Shawber, C., et al., "Notch signaling inhibits muscle cell differentiation through a CBF1-independent pathway," *Development* 122(12):3765-73, Company of Biologists Limited, England (1996).
"4G1" Notch1 monoclonal antibody; Abnova technical datasheet, www.abnova.com/products/products_details.asp?Catalog_id=1-100004851-M10; downloaded Nov. 9, 2012; 8 total pages.
Brorson, K., et al., "Mutational analysis of avidity and fine specificity of anti-levan antibodies," *J. Immunol.* 163(12):6694-701, American Association of Immunologists, United States (1999).

(56) References Cited

OTHER PUBLICATIONS

Brummell, D.A., et al., "Probing the combining site of an anti-carbohydrate antibody by saturation-mutagenesis: role of the heavy chain CDR3 residues," *Biochemistry* 32(4):1180-7, American Chemical Society, United States (1993).

Kobayashi, H., et al., "Trytophan H33 plays an important role in pyrimidine (6-4) pyrimidone photoproduct binding by a high-affinity antibody," *Protein Eng.* 12(10):879-84, Oxford University Press, England (1999).

Burks, E.A., et al., "In vitro scanning saturation mutagenesis of an antibody binding pocket," *Proc. Natl. Sci. U S A.* 94(2):412-7, National Academy of Sciences, United States (1997).

Jang, Y.J., et al., "The structural basis for DNA binding by an anti-DNA autoantibody," *Mol. Immunol.* 35(18):1207-17, Pergamon Press, England (1998).

McDaniell, R., et al., "Notch2 Mutations Cause Alagille Syndrome, a Heterogeneous Disorder of the Notch Signaling Pathway," *Am. J. Hum. Genet.* 79(1):169-73, University of Chicago Press, United States (2006).

Nickoloff, B.J., et al., "Notch signaling as a therapeutic target in cancer: a new approach to the development of cell fate modifying agents," *Oncogene* 22(42):6598-608, Nature Publishing Group, England (2003).

Varnum-Finney, B., et al., "The Notch ligand, Jagged-1, influences the development of primitive hematopoietic precursor cells," *Blood* 91(11):4084-91, The American Society of Hematology, United States (1998).

Jundt, F., et al., "Jagged1-induced Notch signaling drives proliferation of multiple myeloma cells," *Blood* 103:3511-3515, The American Society of Hematology, United States (2004).

Wu, Y., "Therapeutic antibody targeting of individual Notch receptors," *Nature* 464:1052-1057, Nature Publishing Group, England (2010).

Siebel, C.W. "PL07-04 Notch Antibody Antagonists for Cancer Therapy," Invited Abstracts (Plenary Session), Abstract nr PL07-04, American Association for Cancer Research, United States (2007).

Gordon, W.R., et al., "Structural basis for autoinhibition of Notch," *Nat. Struct. Mol. Biol.* 14(4):295-300, Nature Pub. Group, United States (2007).

Sanchez-Irizarry, C., "Notch Subunit Heterodimerization and Prevention of Ligand-Independent Proteolytic Activation Depend, Respectively, on a Novel Domain and the LNR Repeats," *Mol. Cell Biol.* 24(21):9265-9273, American Society for Microbiology, United States (2004).

Roy, M., et al., "The multifaced role of Notch in cancer," *Curr. Opin. Genet. Dev.* 17(1):52-59, Elsevier, England (2007).

Supplemental Data for Li, K., et al., "Modulation of Notch Signaling by Antibodies Specific for the Extracellular Negative Regulatory Region of Notch3," *J. Biol. Chem.* 283:8046-8054, The American Society for Biochemistry and Molecular Biology, Inc., United States (2008); 9 total pages.

NCBI Entrez, GenBank Report, Accession No. AAA39140, Pennell, C.A., et al., Entry Date Apr. 27, 1993, accessed on Jun. 3, 2013.

Aste-Amezaga, M., et al., "Characterization of Notch1 Antibodies That Inhibit Signaling of Both Normal and Mutated Notch1 Receptors," *PLoS One* 5(2):1-13, Public Library of Science, United States (2010).

Supplementary European Search Report for European Patent Application No. EP 11 73 3378 issued Apr. 26, 2013, The Hague.

Dikic, I., et al., "Notch: Implications of endogenous inhibitors for therapy," *Bioessays* 32:481-487, John Wiley & Sons, United States (2010).

Lin, L., et al., "Targeting Specific Regions of the Notch3 Ligand-Binding Domain Induces Apoptosis and Inhibits Tumor Growth in Lung Cancer," *Can. Res.* 70:632-638, American Assoc. for Cancer Research, United States (2010).

Bheeshmachar, G., et al., "Evidence for a Role for Notch Signaling in the Cytokine-Dependent Survival of Activated T cells," *J. Immunol.* 177:5041-5050, The American Association of Immunologists Inc., United States (2006).

Extended European Search Report of European Appl. No. 08 72 4737.5, European Patent Office, Munich, Germany, dated Sep. 24, 2010.

Novus, "Biologicals Product: Mouse Monoclonal anti-Notch 1 (A6) antibody datasheet," XP008115324, accessed at http://www.novusbio.com/data_sheet/pdf_data_sheet/5985.

Allenspach, E.J., et al., "Notch Signaling in Cancer," *Cancer Biol.* 1:466-476, Landes Bioscience, United States (2002).

Armstrong, F., et al., "Notch is a key regulator of human T-cell acute leukemia initiating cell activity," *Blood* 113:1730-1740, The American Society of Hematology, United States (2009).

Bellavia, D., et al., "Constitutive activation of NF-Kband T-cell leukemia/lymphoma in Notch3 transgenic mice," *EMBO J.* 19:3337-3348, Oxford University Press, United States (2000).

Callahan, R. & Raafat, A., "Notch Signaling in Mammary Gland Tumorigenesis," *Journal of Mammary Gland Biology and Neoplasia* 6:23-26, Plenum Publishing Corporation, United States (2001).

Campbell, A.M., "Monoclonal antibody technology," vol. 13, pp. v-29, Elsevier Science Publishers B.V, The Netherlands, 1984.

Cox, C.V., et al., "Characterization of acute lymphoblastic leukemia progenitor cells," *Blood* 104:2919-2925, The American Society of Hematology, United States (2004).

Deftos, M.L., et al., "Correlating notch signaling with thymocyte maturation," *Immunity* 9:777-786, Cell Press, United States (1998).

English language Abstract of WIPO Patent Publication No. WO 02/00576 A1.

Fleming, R.J., et al., "The Notch receptor and its ligands," *Trends in Cell Biol.* 7:437-441, Elsevier Science Ltd., The Netherlands (1997).

Fre, S., et al., "Notch signals control the fate of immature progenitor cells in the intestine," *Nature* 435:964-968, Nature Publishing Group, England (2005).

Gallahan, D., and Callahan, R., "The mouse mammary tumor associated gene INT3 is a unique member of the *Notch* gene family (*Notch4*)," *Oncogene* 14:1838-1890, Stockton Press, United States (1997).

Grabher, C., et al., "Notch 1 activation in the molecular pathogensis of T-cell acute lymphoblastic leukaemia," *Nature Reviews Cancer* 6:347-359, Nature Publishing Group, England (2006).

Imatani, A., and Callahan, R., "Identification of a novel *Notch-4/Int-3* RNA species encoding an activated gene product in certain human tumor cell lines," *Oncogene* 19:223-231, Macmillan Publishers Ltd., England (2000).

International Search Report for International Application No. PCT/US08/00884, United States Patent and Trademark Office, U.S.A., mailed on Oct. 1, 2008.

International Search Report for International Application No. PCT/US09/03995, United States Patent and Trademark Office, U.S.A., mailed on Mar. 2, 2010.

\* cited by examiner

NOTCH1 BINDING AGENTS AND METHODS OF USE THEREOF

CROSS REFERENCE TO RELATED APPLICATIONS

This application claims the priority benefit of U.S. Provisional Application No. 61/294,762, filed Jan. 13, 2010 and U.S. Provisional Application No. 61/410,651, filed Nov. 5, 2010, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: Subst_Seq_Listing_ascii.txt, Size: 43 kilobytes; and Date of Creation: May 3, 2012) is herein incorporated by reference in its entirety.

FIELD OF THE INVENTION

The field of this invention generally relates to antibodies and other agents that bind human Notch1, as well as methods of using the antibodies and other agents for the treatment of hematologic diseases, particularly diseases associated with the Notch pathway.

BACKGROUND OF THE INVENTION

The Notch signaling pathway is a universally conserved signal transduction system. It is involved in cell fate determination during development including embryonic pattern formation and post-embryonic tissue maintenance. In addition, Notch signaling has been identified as a critical factor in the maintenance of hematopoietic stem cells.

The mammalian Notch receptor family includes four members, Notch1, Notch2, Notch3 and Notch4. Notch receptors are large single-pass type I transmembrane proteins with several conserved structural motifs. The extracellular domain contains a variable number of epidermal growth factor (EGF)-like repeats involved in ligand binding and three cysteine-rich LIN-12/Notch repeats (LNRs) involved in Notch heterodimerization. The intracellular domain contains a RAM23 motif involved in binding Notch downstream signaling proteins, 7 cdc10/ankyrin repeats also involved in mediating downstream signaling and a PEST domain involved in Notch protein degradation.

Mammalian Notch ligands include Delta-like 1 (DLL1), Delta-like 3 (DLL3), Delta-like 4 (DLL4), Jagged1 and Jagged2. Similar to Notch receptors, Notch ligands are type I transmembrane proteins with several conserved structural motifs. Extracellular motifs common to all Notch ligands include a single Delta/Serrate/Lag-2 (DSL) domain involved in receptor binding, as well as a variable number of EGF-like repeats that may be involved in stabilizing receptor binding. The extracellular domain of Jagged proteins contains a cysteine-rich region which has partial homology to the von Willebrand factor type C domain and is likely involved in ligand dimerization. This motif is not present in DLL family members. (Leong et al., 2006, *Blood*, 107:2223-2233).

The extracellular domain of a Notch receptor interacts with the extracellular domain of a Notch ligand, typically on adjacent cells, resulting in two proteolytic cleavages of the Notch receptor. One extracellular cleavage is mediated by an ADAM (A Disintegrin And Metallopeptidase) protease and a second cleavage within the transmembrane domain is mediated by the gamma secretase complex. This latter cleavage generates the Notch intracellular domain (ICD), which translocates to the nucleus where it activates the CBF1, Suppressor of Hairless, Lag-2 (CSL) family of transcription factors as the major downstream effectors to increase transcription of nuclear basic helix-loop-helix transcription factors of the Hairy/Enhancer of Split (HES) family. (Artavanis et al., 1999, *Science*, 284:770; Brennan and Brown, 2003, *Breast Cancer Res.*, 5:69; Iso et al., 2003, *Arterioscler. Thromb. Vasc. Biol.*, 23:543).

The Notch pathway has been linked to the pathogenesis of both hematologic and solid tumors and cancers. Numerous cellular functions and microenvironmental cues associated with tumorigenesis have been shown to be modulated by Notch pathway signaling, including cell proliferation, apoptosis, adhesion, and angiogenesis. (Leong et al., 2006, *Blood*, 107:2223-2233). In addition, Notch receptors and/or Notch ligands have been shown to play potential oncogenic roles in a number of human cancers, including acute myelogenous leukemia, B cell chronic lymphocytic leukemia, Hodgkin lymphoma, multiple myeloma, T-cell acute lymphoblastic leukemia, brain cancer, breast cancer, cervical cancer, colon cancer, lung cancer, pancreatic cancer, prostate cancer and skin cancer. (Leong et al., 2006, *Blood*, 107:2223-2233).

The Notch1 gene in humans was first identified in a subset of T-cell acute lymphoblastic leukemias as a translocated locus resulting in activation of the Notch pathway (Ellisen et al., 1991, *Cell*, 66:649-61). More recently, it has been shown that more than 50% of human T-cell acute lymphoblastic leukemias have activating mutations that involve the extracellular heterodimerization domain and/or the C-terminal PEST domain of Notch1 (Weng et al., 2004, *Science*, 306: 269-271; Pear & Aster, 2004, *Curr. Opin. Hematol.*, 11:416-33). Constitutive activation of Notch1 signaling in T-cells in mouse models similarly generates T-cell lymphomas suggesting a causative role (Robey et al., 1996, *Cell*, 87:483-92; Pear et al., 1996, *J. Exp. Med.*, 183:2283-91; Yan et al., 2001, *Blood*, 98:3793-9; Bellavia et al., 2000, *EMBO J.* 19:3337-48). Retrovirally-activated Notch2 has been implicated in thymic lymphoma induced by feline leukemia virus (Rohn et al., 1996, *J. Virology*, 70:8071-8080). Human T-cell acute lymphoblastic leukemia samples have been shown to express Notch3 and its target gene HES-1, which were not expressed in normal peripheral T-cells nor in non-T-cell leukemias (Bellavia et al., 2002, *PNAS*, 99:3788-3793). Thus, the Notch pathway has been identified as a potential target for therapeutic intervention in several hematologic cancers.

Anti-Notch antibodies and their possible use as anti-cancer therapeutics have been reported. See, e.g., U.S. Patent Application Publication Nos. 2008/0131434 and 2009/0081238, each of which is incorporated by reference herein in its entirety. See also International Publication Nos. WO 2008/057144, WO 2008/076960, WO 2008/150525, WO 2010/005566 and WO 2010/005567; each of which is incorporated by reference herein in its entirety.

SUMMARY OF THE INVENTION

The present invention provides binding agents (e.g. antibodies) that specifically bind to a non-ligand binding membrane proximal region of the extracellular domain of a Notch1 receptor and compositions, such as pharmaceutical compositions, comprising those agents. The invention further provides methods of using the binding agents in the treatment of a hematologic cancer by administering the agents to a subject in need thereof. In some embodiments, the methods comprise inhibiting the growth of cancer cells. In some embodiments, the cancer is a hematologic cancer such as a leukemia or lymphoma. In some embodiments the hematologic cancer is acute myelogenous leukemia, Hodgkin lymphoma, multiple myeloma or T-cell acute lymphoblastic leukemia. In some embodiments, the hematologic cancer is T-cell acute lymphoblastic leukemia. In some embodiments, the method of treating hematologic cancers comprises inhibiting Notch1 signaling. In some embodiments, the method of treating hematologic cancers comprises inhibiting Notch1 activation. In some embodiments, the method of treating cancer or inhibiting growth of cancer cells comprises targeting cancer stem cells with the binding agents. In some embodiments, the cancer stem cells comprise leukemia initiating cells. In some embodiments, the methods comprise reducing the frequency of cancer stem cells in a subject, reducing the number of cancer stem cells in a subject, reducing the tumorigenicity of a cancer, and/or reducing the tumorigenicity of a cancer by reducing the number or frequency of cancer stem cells in the subject.

In one aspect, the invention provides methods of treating a hematologic cancer in a subject comprising administering to the subject a therapeutically effective amount of a binding agent that specifically binds a non-ligand binding membrane proximal region of an extracellular domain of human Notch1. In some embodiments the hematologic cancer is acute myelogenous leukemia, Hodgkin lymphoma, multiple myeloma or T-cell acute lymphoblastic leukemia. In some embodiments, the hematologic cancer is T-cell acute lymphoblastic leukemia. In some embodiments the binding agent is an antibody. In some embodiments the binding agent is an antibody comprising (a) a heavy chain CDR1 comprising RGYWIE (SEQ ID NO:15), a heavy chain CDR2 comprising QILPGTGRTNYNEKFKG (SEQ ID NO:16), and/or a heavy chain CDR3 comprising FDGNYGYYAMDY (SEQ ID NO:17); and/or (b) a light chain CDR1 comprising RSSTGAVTTSNYAN (SEQ ID NO:18), a light chain CDR2 comprising GTNNRAP (SEQ ID NO:19), and/or a light chain CDR3 comprising ALWYSNHWVFGGGTKL (SEQ ID NO:20).

In certain embodiments, the invention provides methods of treating a hematologic cancer in a subject comprising administering to the subject a therapeutically effective amount of a binding agent (e.g., an antibody) that specifically binds a non-ligand binding membrane proximal region of an extracellular domain of human Notch1, wherein the binding agent comprises: (a) a heavy chain CDR1 comprising RGYWIE (SEQ ID NO:15), or a variant thereof comprising 1, 2, 3, or 4 amino acid substitutions; (b) a heavy chain CDR2 comprising QILPGTGRTNYNEKFKG (SEQ ID NO:16), or a variant thereof comprising 1, 2, 3, or 4 amino acid substitutions; and/or (c) a heavy chain CDR3 comprising FDGNYGYYAMDY (SEQ ID NO:17), or a variant thereof comprising 1, 2, 3, or 4 amino acid substitutions. In certain embodiments, the binding agent (e.g. antibody) comprises (or further comprises) (a) a light chain CDR1 comprising RSSTGAVTTSNYAN (SEQ ID NO:18), or a variant thereof comprising 1, 2, 3, or 4 amino acid substitutions; (b) a light chain CDR2 comprising GTNNRAP (SEQ ID NO:19), or a variant thereof comprising 1, 2, 3, or 4 amino acid substitutions; and/or (c) a light chain CDR3 comprising ALWYSNHWVFGGGTKL (SEQ ID NO:20), or a variant thereof comprising 1, 2, 3, or 4 amino acid substitutions. In some embodiments, the amino acid substitutions are conservative amino acid substitutions. In some embodiments the hematologic cancer is acute myelogenous leukemia, Hodgkin lymphoma, multiple myeloma or T-cell acute lymphoblastic leukemia. In some embodiments, the hematologic cancer is T-cell acute lymphoblastic leukemia.

In certain embodiments, the invention provides methods of treating a hematologic cancer in a subject comprising administering to the subject a therapeutically effective amount of a binding agent (e.g., an antibody) that specifically binds a non-ligand binding membrane proximal region of an extracellular domain of human Notch1, wherein the binding agent comprises: (a) a heavy chain variable region having at least about 90%, at least about 95%, at least about 98%, or 100% sequence identity to SEQ ID NO:14 or SEQ ID NO:24; and/or (b) a light chain variable region having at least about 90%, at least about 95%, at least about 98%, or 100% sequence identity to SEQ ID NO:8, SEQ ID NO:28, or SEQ ID NO:32. In some embodiments, the binding agent (e.g. antibody) comprises a heavy chain variable region comprising SEQ ID NO:14 and a light chain variable region comprising SEQ ID NO:8. In some embodiments, the binding agent (e.g., an antibody) comprises a heavy chain variable region comprising SEQ ID NO:24 and a light chain variable region comprising SEQ ID NO:28. In some embodiments, the binding agent (e.g., an antibody) comprises a heavy chain variable region comprising SEQ ID NO:24 and a light chain variable region comprising SEQ ID NO:32. In some embodiments, the Notch1 binding agent is antibody 52M51. In some embodiments, the Notch1 binding agent is a humanized form of antibody 52M51.

In certain embodiments, the Notch1 binding agent comprises the heavy chains and light chains of the 52M51 antibody (with or without the signal/leader sequence). In certain embodiments, the Notch1 binding agent is the 52M51 antibody. In some embodiments, the Notch1 is a humanized form of antibody 52M51. The hybridoma cell line producing the 52M51 antibody was deposited with the American Type Culture Collection (ATCC), 10801 University Boulevard, Manassas, Va., USA, under the conditions of the Budapest Treaty on Aug. 7, 2008, and assigned designation number PTA-9405. In some embodiments, the antibody is a humanized version of antibody 52M51, 52M51H4L3, as encoded by the polynucleotide deposited with the ATCC, under the conditions of the Budapest Treaty on Oct. 15, 2008, and assigned designation number PTA-9549.

In certain embodiments of each of the aforementioned aspects or embodiments, as well as other aspects and/or embodiments described elsewhere herein, the binding agent (e.g., an antibody) specifically binds a non-ligand binding membrane proximal region of the extracellular domain of Notch1 receptor wherein the non-ligand binding membrane proximal region of a Notch1 receptor comprises about amino acid 1427 to about amino acid 1732 of a human Notch1 receptor. In some embodiments, the membrane proximal region of a Notch1 receptor comprises at least a portion of SEQ ID NO:2. In some embodiments, the membrane proximal region of a Notch1 receptor comprises SEQ ID NO:2. In certain embodiments, the binding agent (e.g. antibody) specifically binds a non-ligand binding membrane proximal region of an extracellular domain of at least one additional Notch receptor.

In some embodiments, the invention provides an antibody that specifically binds the same or an over-lapping Notch1 epitope as the epitope to which antibody 52M51 binds.

In another aspect, the invention provides methods of treating a hematologic cancer in a subject comprising administering to the subject a therapeutically effective amount of a binding agent (e.g., an antibody) that specifically binds a non-ligand binding membrane proximal region of an extracellular domain of human Notch1, wherein the binding agent binds the same epitope within the membrane proximal region as the epitope to which antibody 52M51 produced by the hybridoma cell line deposited as ATCC Patent Deposit PTA-9405 binds. In some embodiments, the binding agent competes with antibody 52M51 for specific binding to the membrane proximal region of Notch1. In some embodiments, the binding agent competes with antibody 52M51 for specific binding to the non-ligand binding membrane proximal region of Notch1 comprising at least a portion of SEQ ID NO:2. In some embodiments, the binding agent competes with antibody 52M51 for specific binding to an epitope within the non-ligand binding membrane proximal region of Notch1 comprising SEQ ID NO:2. In some embodiments the hematologic cancer is acute myelogenous leukemia, Hodgkin lymphoma, multiple myeloma or T-cell acute lymphoblastic leukemia. In some embodiments, the hematologic cancer is T-cell acute lymphoblastic leukemia.

In another aspect, the invention provides methods of inhibiting growth of a hematologic cancer comprising contacting the cancer cells with an effective amount of a binding agent (e.g. an antibody) that specifically binds a non-ligand binding membrane proximal region of an extracellular domain of human Notch1 receptor, and wherein the antibody comprises: (a) a heavy chain CDR1 comprising RGYWIE (SEQ ID NO:15), a heavy chain CDR2 comprising QILPGTGRT-NYNEKFKG (SEQ ID NO:16), and a heavy chain CDR3 comprising FDGNYGYYAMDY (SEQ ID NO:17); and/or (b) a light chain CDR1 comprising RSSTGAVTTSNYAN (SEQ ID NO:18), a light chain CDR2 comprising GTNNRAP (SEQ ID NO:19), and a light chain CDR3 comprising ALW-YSNHWVFGGGTKL (SEQ ID NO:20). In some embodiments the hematologic cancer is acute myelogenous leukemia, Hodgkin lymphoma, multiple myeloma or T-cell acute lymphoblastic leukemia. In some embodiments, the hematologic cancer is T-cell acute lymphoblastic leukemia.

In certain embodiments of each of the aforementioned aspects or embodiments, as well as other aspects and/or embodiments described elsewhere herein, the binding agent is antibody. In some embodiments the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an antibody fragment. In certain embodiments, the antibody or antibody fragment is monovalent, monospecific, bivalent, bispecific, or multispecific. In certain embodiments, the antibody is conjugated to a cytotoxic moiety. In certain embodiments, the antibody is isolated. In still further embodiments, the antibody is substantially pure.

Also provided are pharmaceutical compositions comprising binding agents (e.g., antibodies) that specifically bind to a non-ligand binding membrane proximal region of an extracellular domain of human Notch1 receptor for use in the methods of treating hematologic cancers described herein. In certain embodiments, the pharmaceutical compositions further comprise a pharmaceutically acceptable carrier.

In certain embodiments of each of the aforementioned aspects or embodiments, as well as other aspects and/or embodiments described elsewhere herein, the binding agent (e.g., antibody) is an antagonist of Notch1. In some embodiments, the binding agent inhibits Notch1 signaling. In some embodiments, the binding agent inhibits Notch1 activation. In some embodiments, the binding agent inhibits Notch1 activity. In some embodiments, the binding agent inhibits activity of a constitutively activated Notch1. In some embodiments, the binding agent inhibits cleavage within the membrane proximal region. In certain embodiments, the binding agent inhibits cleavage of Notch1 (e.g., cleavage at the S2 site by a metalloprotease) and/or inhibits activation of Notch1 by ligand binding. In some embodiments, the binding agent inhibits release or formation of the intracellular domain (ICD) of Notch1. In certain embodiments, the binding agent inhibits growth of hematologic cancer cells. In some embodiments, the binding agent inhibits growth of T-cell acute lymphoblastic leukemia cells.

In a further aspect, the invention provides a method of inhibiting activity of Notch1 in a hematologic cancer cell, comprising contacting the cancer cell with an effective amount of any of the antibodies or polypeptides described in the aforementioned aspects and embodiments, as well as other aspects/embodiments described elsewhere herein. In certain embodiments, the hematologic cancer cell is a T-cell acute lymphoblastic leukemia cell.

In another aspect, the invention provides a method of inhibiting the growth of a hematologic cancer in a subject, the method comprising administering to the subject a therapeutically effective amount of any of the antibodies or polypeptides described in the aforementioned aspects and embodiments, as well as other aspects/embodiments described elsewhere herein. In some embodiments, the hematologic cancer comprises cancer stem cells. In some embodiments, the hematologic cancer comprises leukemia initiating cells. In some embodiments, the methods comprise targeting the cancer stem cells with the binding agents and antibodies described herein. In certain embodiments, the methods comprise reducing the frequency of cancer stem cells in a hematologic cancer, reducing the number of leukemia initiating cells in a hematologic cancer, reducing the number of cancer stem cells in a hematologic cancer, reducing the tumorigenicity of a hematologic cancer, and/or reducing the tumorigenicity of a hematologic cancer by reducing the number or frequency of cancer stem cells in the hematologic cancer. In some embodiments, the methods comprise inhibiting the activity of Notch1 and/or inhibiting growth of a hematologic cancer. In certain embodiments, the hematologic cancer is acute myelogenous leukemia, Hodgkin lymphoma, multiple myeloma or T-cell acute lymphoblastic leukemia. In certain embodiments, the hematologic cancer cell is a T-cell acute lymphoblastic leukemia cell.

In an additional aspect, the invention provides a method of inhibiting growth of a hematologic cancer in a subject, the method comprising administering to the subject a therapeutically effective amount of an antibody that specifically binds a non-ligand binding membrane proximal region of an extracellular domain of human Notch1, wherein binding inhibits activity of Notch1. In some embodiments, the methods comprise inhibiting the activity of a constitutively activated Notch1.

In a further aspect, the invention provides a method of reducing the tumorigenicity of a hematologic cancer that comprises cancer stem cells by reducing the frequency or number of cancer stem cells in the cancer, the method comprising contacting the cancer cells with an effective amount of a binding agent or an antibody as described herein that inhibits the activity of Notch1.

In certain embodiments of each of the aforementioned aspects and/or embodiments, as well as other aspects or embodiments described herein, the methods further comprise administering to the subject at least one additional therapeutic agent. In certain embodiments of each of the aforementioned aspects or embodiments, as well as other aspects and/or embodiments described elsewhere herein, the antibody or polypeptide is administered to a subject in combination with an additional treatment for a hematologic cancer. In certain embodiments, the additional treatment for a hematologic cancer comprises radiation therapy, chemotherapy, and/or an additional antibody therapeutic.

The invention further provides a method of treating a hematologic cancer in a human, wherein the hematologic cancer comprising cancer stem cells is not characterized by over-expression of one or more Notch receptors by the cancer stem cell, comprising administering to the human a therapeutically effective amount of a binding agent or an antibody which binds a membrane proximal region of the extracellular domain of Notch1 and blocks ligand activation of Notch1. In some embodiments, the binding agents or antibodies as described herein are administered to treat a hematologic cancer, wherein the hematologic cancer is characterized by a constitutively activated Notch1.

The invention further provides a method of treating a hematologic cancer in a human comprising administering to the human therapeutically effective amounts of (a) a first antibody which binds Notch1 and inhibits growth of cancer stem cells which over-express Notch1; and (b) a second antibody which binds a Notch receptor and blocks ligand activation of a Notch receptor. In some embodiments, the method comprises administering to the human therapeutically effective amounts of (a) a first antibody which binds Notch1 and inhibits growth of cancer stem cells which over-express Notch1; and (b) a second antibody which binds VEGF.

In further embodiments, the invention provides articles of manufacture for use (among other things) in the above methods. For example, the invention provides an article of manufacture comprising a container and a composition contained therein, wherein the composition comprises an antibody that binds Notch, and further comprises a package insert indicating that the composition can be used to treat a cancer comprising cancer stem cells. In some embodiments, the invention provides an article of manufacture comprising a container and a composition contained therein, wherein the composition comprises an antibody that binds Notch, and further comprises a package insert indicating that the composition can be used to treat cancer comprising cancer stem cells that express one or more Notch receptors.

In certain embodiments, the invention additionally pertains to an article of manufacture comprising a container and a composition contained therein, wherein the composition comprises an antibody which binds a Notch receptor and blocks ligand activation of a Notch receptor, and further comprises a package insert indicating that the composition can be used to treat cancer, wherein the cancer comprises cancer stem cells that are not characterized by overexpression of the Notch receptor.

In certain embodiments, an article of manufacture is provided which comprises (a) a first container with a composition contained therein, wherein the composition comprises a first antibody that binds a Notch receptor and inhibits growth of cancer cells comprising cancer stem cells overexpressing Notch; and (b) a second container with a composition contained therein, wherein the composition comprises a second antibody which binds Notch and blocks ligand activation of a Notch receptor.

In some embodiments, a further article of manufacture is provided which comprises a container and a composition contained therein, wherein the composition comprises an antibody which binds Notch and blocks ligand activation of a Notch receptor, and further comprises a package insert indicating that the composition can be used to treat a cancer selected from the group consisting of acute myelogenous leukemia, Hodgkin lymphoma, multiple myeloma and T-cell acute lymphoblastic leukemia.

The invention additionally provides: an antibody (e.g., a human antibody or a humanized antibody) which binds Notch and blocks ligand activation of a Notch receptor; a composition comprising the antibody and a pharmaceutically acceptable carrier; and an immunoconjugate comprising the antibody conjugated with a cytotoxic agent.

In one aspect, the invention provides an isolated polynucleotide encoding any of the antibodies or polypeptides of the aforementioned aspects or embodiments, as well as other aspects and/or embodiments described elsewhere herein. In some embodiments, the invention provides a vector comprising the polynucleotide. In some embodiments, a host cell comprises the polynucleotide or the vector. In other embodiments, a process of producing the antibody comprises culturing a host cell comprising the polynucleotide so that the polynucleotide is expressed and, optionally, further comprises recovering the antibody from the host cell culture (e.g., from the host cell culture medium).

Moreover, the invention provides an isolated polynucleotide encoding a humanized or human antibody as described in the aforementioned embodiments or aspects, as well as described elsewhere herein; a vector comprising the polynucleotide; a host cell comprising the polynucleotide or the vector; as well as a process of producing the antibody comprising culturing a host cell comprising the polynucleotide so that the polynucleotide is expressed and, optionally, further comprising recovering the antibody from the host cell culture (e.g., from the host cell culture medium).

The invention further pertains to an immunoconjugate comprising an antibody that binds Notch conjugated to one or more calicheamicin molecules, and the use of such conjugates for treating a Notch expressing cancer, e.g., a cancer in which cancer stem cells over-express Notch.

Where aspects or embodiments of the invention are described in terms of a Markush group or other grouping of alternatives, including, but not limited to, groups of alternatives separated by "and/or" or "or," the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention. For example, language such as "X and/or Y" encompasses "X" individually, "Y" individually, as well as "X" and "Y" together.

derived from Notch1-HeLa cells cultured in the presence of a soluble Notch ligand (hDLL4-Fc) and Notch1 receptor antibodies. Results from non-transfected (NT) cells with and without hDLL4-Fc are shown on the far left of the x-axis. 52M51 murine hybridoma-derived antibody and humanized variant 52M51H4L3 are shown along the x-axis in various concentrations as indicated. Both the parental murine antibody 52M51 and the humanized variant significantly inhibited Notch signaling as indicated by a decrease in luciferase activity. (D) Western blot analysis of ICD formation after ligand-mediated stimulation of Notch1-expressing HeLa cells. Minimal ICD is produced in the absence of DLL4 ligand (-DLL4), but formation is stimulated by the presence of DLL4. Antibodies 52M51, 52M63, 52M74, and 52M80 reduced ICD formation to background levels despite the presence of DLL4.

Figure 2:
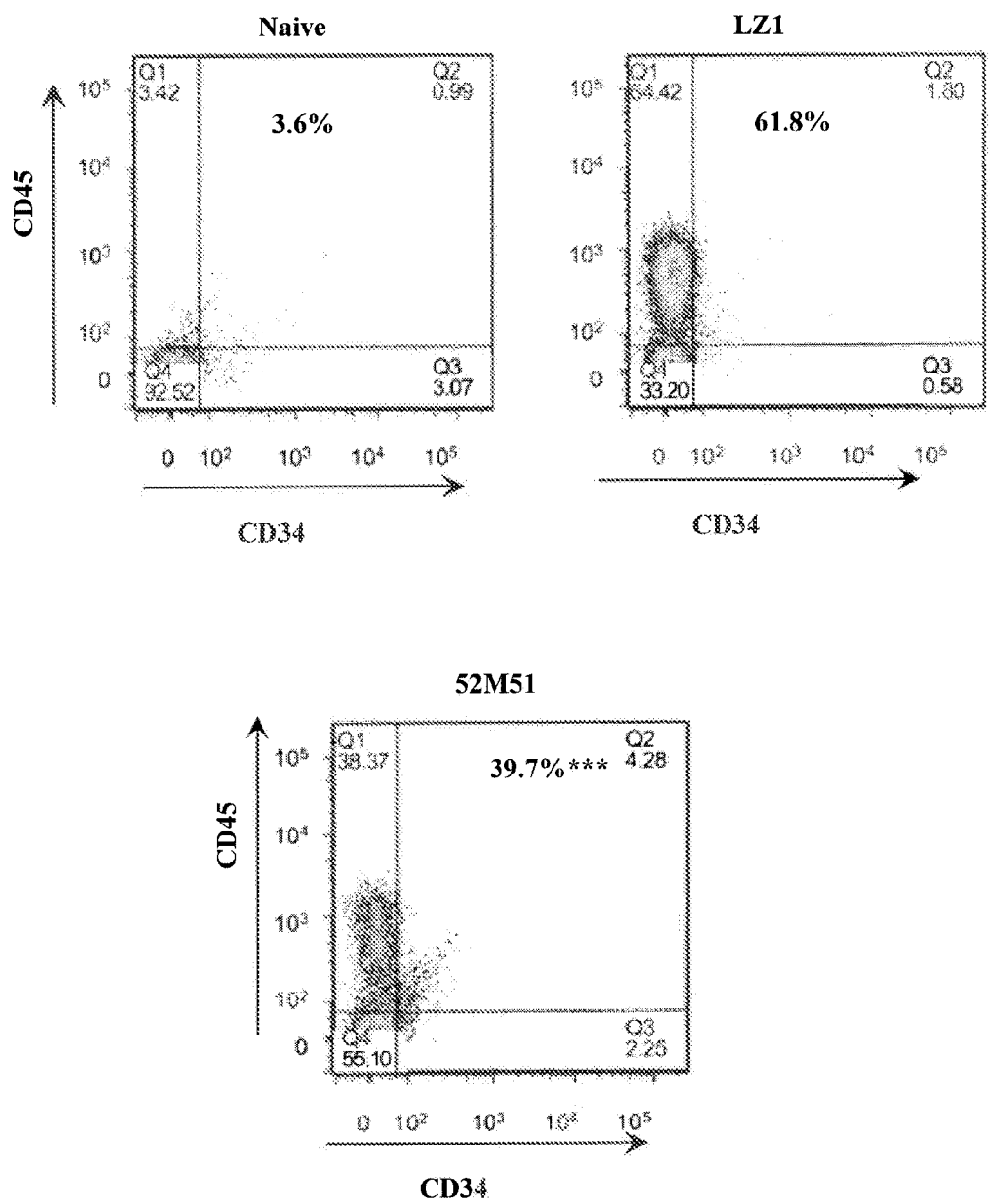

FIG. 2: Evaluation of anti-Notch1 antibodies in a leukemia xenograft model. NOD/SCID mice were preconditioned with $10 \times 10^6$ bone marrow mononuclear cells after irradiation. Seven days later, the mice were injected with $5 \times 10^6$ primary T-cell acute lymphoblastic leukemia cells. Five weeks after the T-cell acute lymphoblastic leukemia cells were injected, the mice were sacrificed and cells isolated from the spleens were analyzed for T-ALL engraftment by flow cytometry. Flow cytometric analysis was carried out using specific monoclonal antibodies against human CD45 and CD34. The fraction of cells staining positive for the antibodies was determined using Tree Star FlowJo software. The significance was calculated by Student t-Test using GraphPad Prism software. The percentage of human CD45+ and CD34+ cells in mouse spleens is indicated. *** represents a significance of $p<0.001$ compared to control antibody LZ-1.

Figure 3:
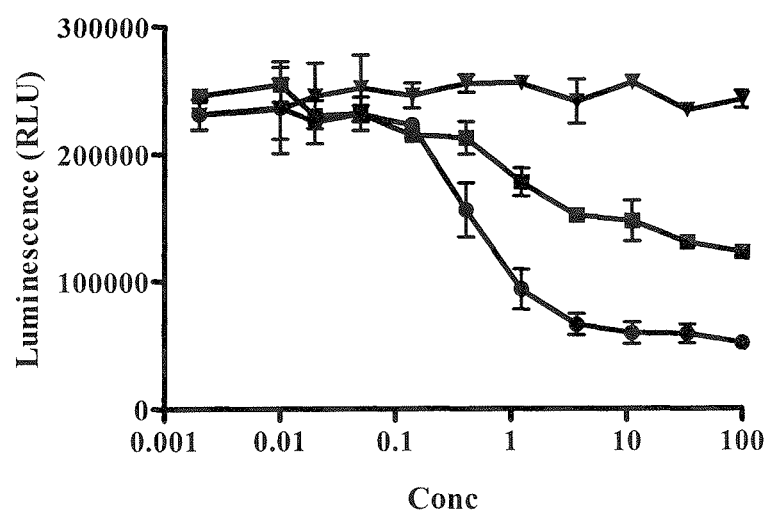

FIG. 3: In vitro evaluation of Notch1 inhibition in HPB-ALL cells. HPB-ALL cells plated in 96 well plates and treated with anti-Notch1 antibody 52M51 (-■-), a control antibody (-▼-) or dibenzazepine (DBZ) (-●-). Data is shown as relative light units (RLU).

Figure 4:
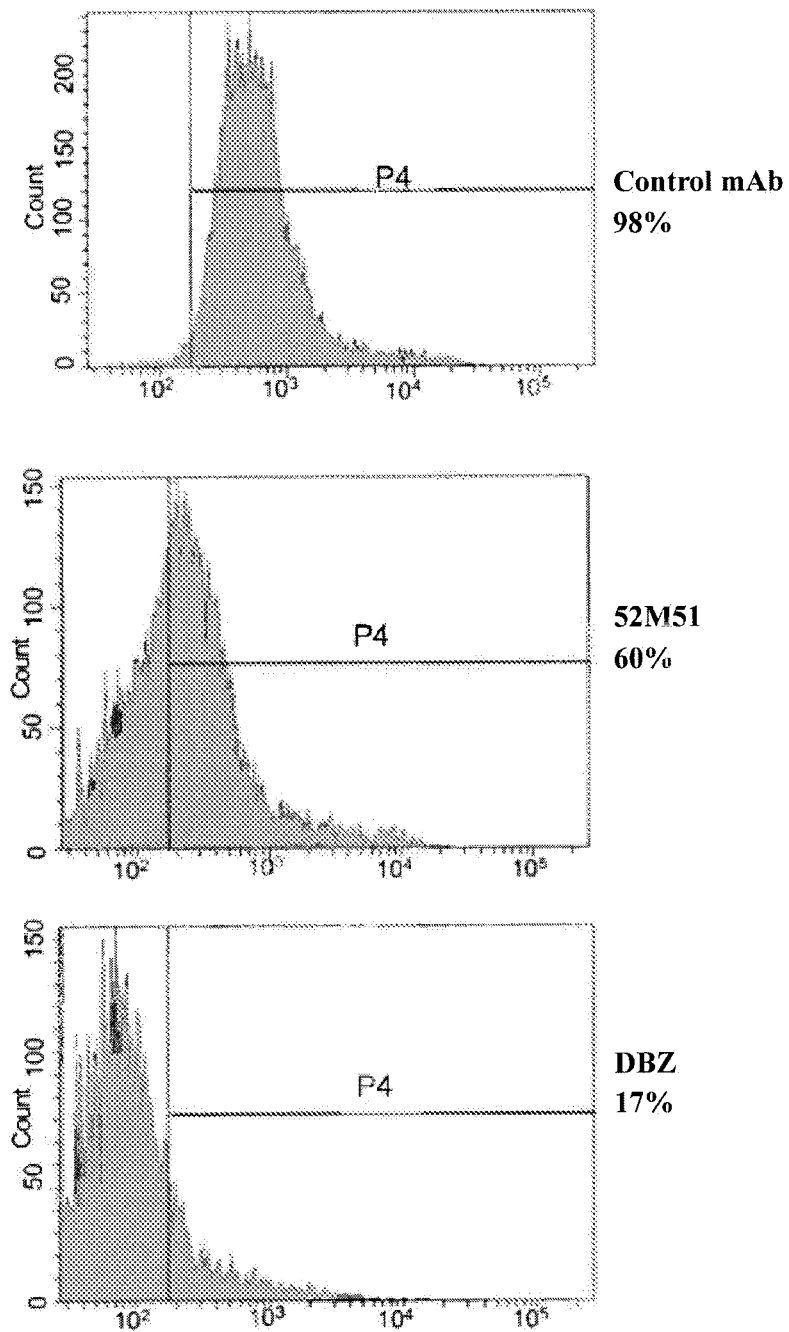

FIG. 4: In vitro evaluation of Notch1 inhibition on proliferation of HPB-ALL cells. HPB-ALL cells were incubated in the presence of 12 μM DBZ, 100 μg·ml of anti-Notch1 antibody 52M51 or 100 μg/ml of control antibody. Cells were analyzed for K167 protein by flow cytometry.

Figure 5:
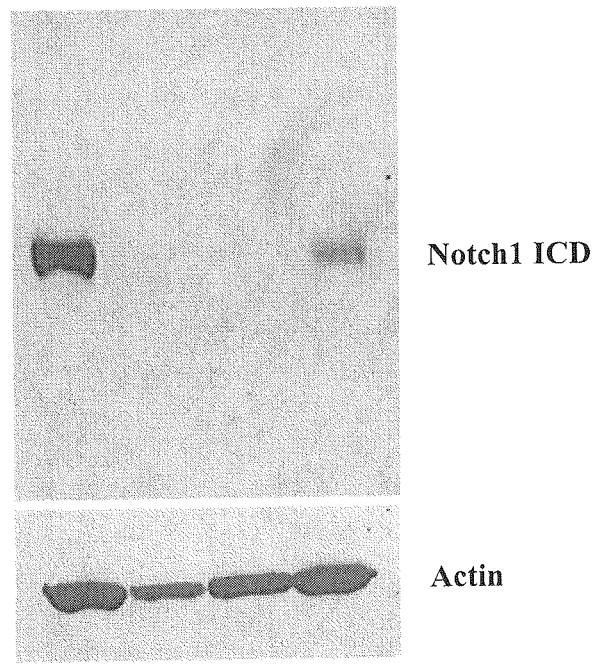

FIG. 5: In vitro evaluation of Notch1 inhibition on ICD formation. HPB-ALL cells were incubated in the presence of 12 μM DBZ, 100 μg·ml of anti-Notch1 antibody 52M51 or 100 μg/ml of control antibody. Whole cell protein extracts were separated by SDS-PAGE and evaluated by Western Blot analysis using an antibody specific for Notch1 ICD.

Figure 6:
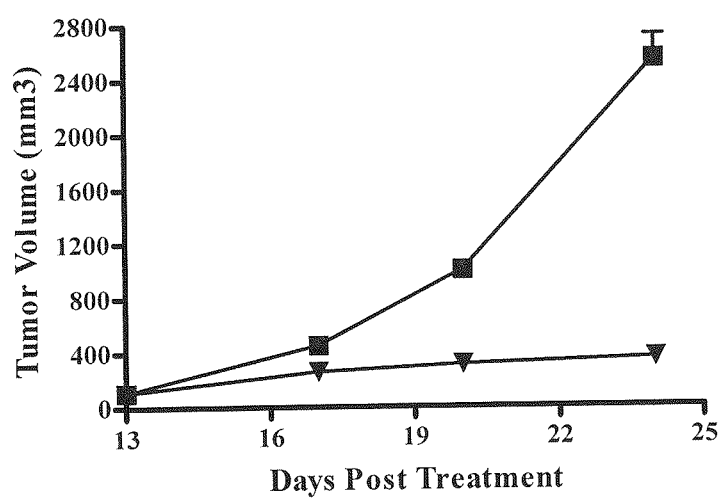

FIG. 6: Inhibition of HPB-ALL tumor growth in vivo by anti-Notch1 antibody. HPB-ALL cells were injected subcutaneously into NOD/SCID mice. Mice were treated with control antibody (-■-) or anti-Notch1 antibody 52M51 (-▼-). Data is shown as tumor volume (mm$^3$) over days post-treatment. Antibodies were administered at 15 mg/kg once a week.

Figure 7:
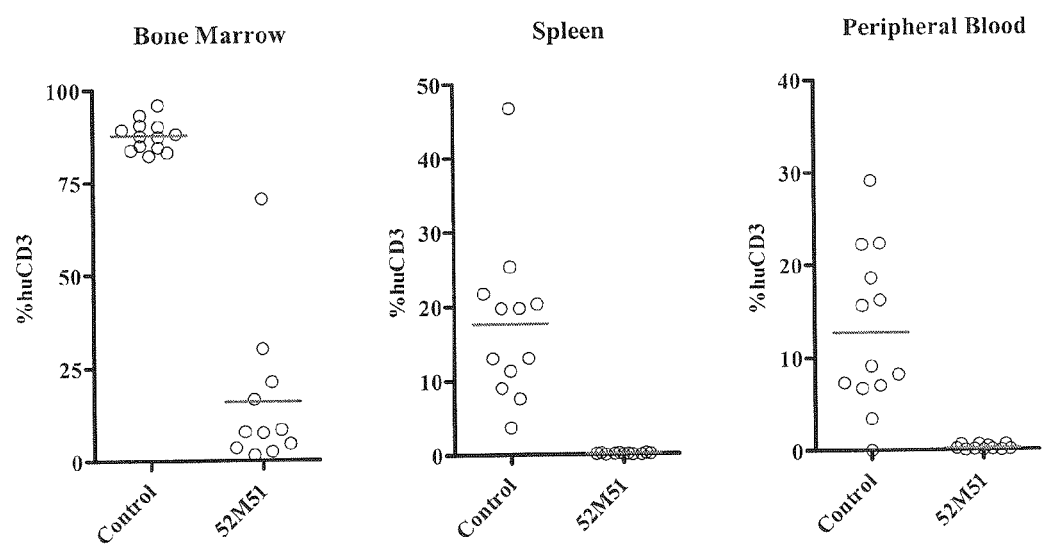

FIG. 7: Evaluation of anti-Notch1 antibodies in a disseminated leukemia xenograft model. HPB-ALL cells were injected into the tail vein of NOD/SCID mice. One day after injection, animals were treated with a control antibody or anti-Notch1 antibody 52M51. Approximately 5 weeks later, mice were euthanized and spleen, peripheral blood and bone marrow were analyzed for the presence of HPB-ALL cells.

DETAILED DESCRIPTION OF THE INVENTION

The present invention provides novel agents, including, but not limited to polypeptides such as antibodies, that bind one or more human Notch receptors, particularly Notch1. The Notch binding agents include antagonists of human Notch1. Related polypeptides and polynucleotides, compositions comprising the Notch binding agents, and methods of making the Notch binding agents are also provided. Methods of using the novel Notch binding agents, such as methods of inhibiting growth of hematologic cancers and/or treating hematologic cancers, are further provided.

The present invention further identifies molecules (e.g., antibodies) that specifically bind to a non-ligand binding membrane proximal region of the extracellular domain of human Notch1 and inhibit tumor growth in vivo. The ligand binding region of Notch, which is necessary and sufficient for ligand binding, has been identified as EGF repeats 11 and 12, suggesting this region of the Notch receptor is important in Notch signaling and tumorigenesis (Rebay et al., 1991, *Cell*, 67:687; Lei et al., 2003, *Dev.*, 130:6411; Hambleton et al., 2004, *Structure*, 12:2173). Unexpectedly, antibodies that bind outside the ligand binding domain of the extracellular domain of human Notch receptor have been found to inhibit tumor cell growth in vivo (see U.S. Patent Pub. No. 2008/0131434 and International Pub. No. WO 2010/005567, each of which is incorporated by reference herein in its entirety). Thus, antibodies that bind outside the ligand binding domain of the extracellular domain of one or more of the human Notch receptors—Notch1, Notch2, Notch3, and Notch4— have value as potential cancer therapeutics.

Figure 1:
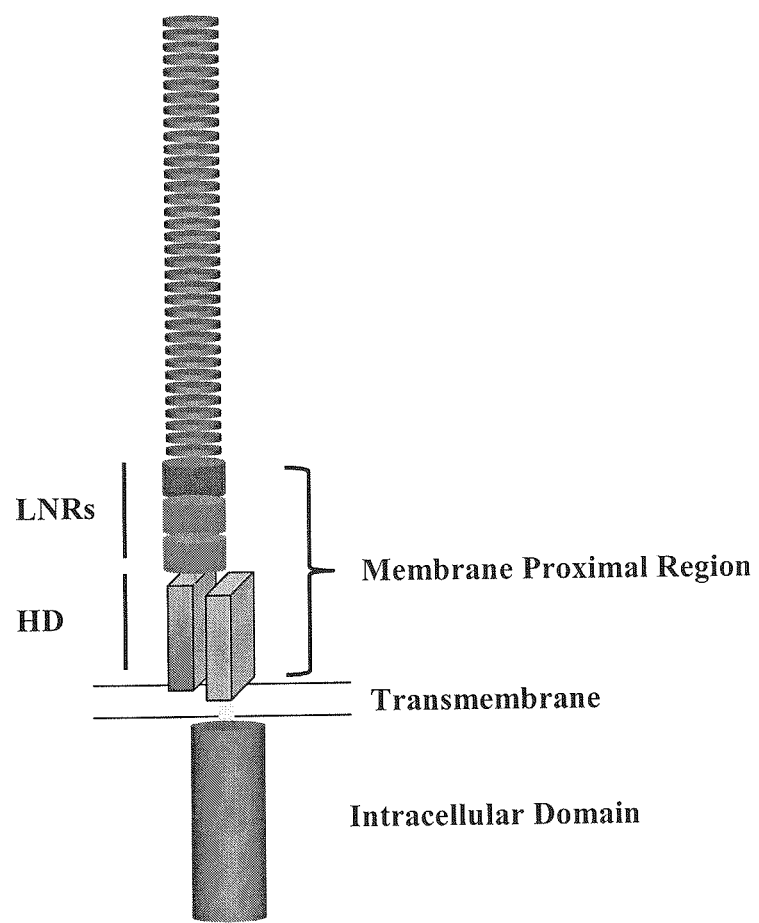
FIG. 1: Identification of Antibodies Targeting the Membrane Proximal Region of Notch that Inhibit Notch Signaling. (A) Schematic of the Notch receptor and 52M antigen region. The 52M antigen includes the area of the Notch1 receptor subject to cleavage by furin during maturation of the receptor and cleavage by ADAM (A Disintegrin and Metalloprotease) proteases following ligand binding. Subsequent processing by gamma-secretase causes the release of the intracellular domain (ICD) of Notch that activates gene transcription in the nucleus. (B) Luciferase levels (y-axis) derived from Notch1-HeLa cells cultured in the presence of a soluble Notch ligand (hDLL4-Fc) and Notch1 receptor antibodies. Results from non-transfected (NT) cells with and without hDLL4-Fc are shown on the far left of the x-axis. 52M Notch1 antibodies are shown along the x-axis and compared to DBZ, a Notch gamma-secretase inhibitor, and 21M18, an anti-DLL4 antibody. Notch1 antibodies 52M51, 52M63, 52M74 and 52M80 all significantly inhibited Notch signaling as indicated by a decrease in luciferase activity. (C) Luciferase levels (y-axis)
Figure 1:
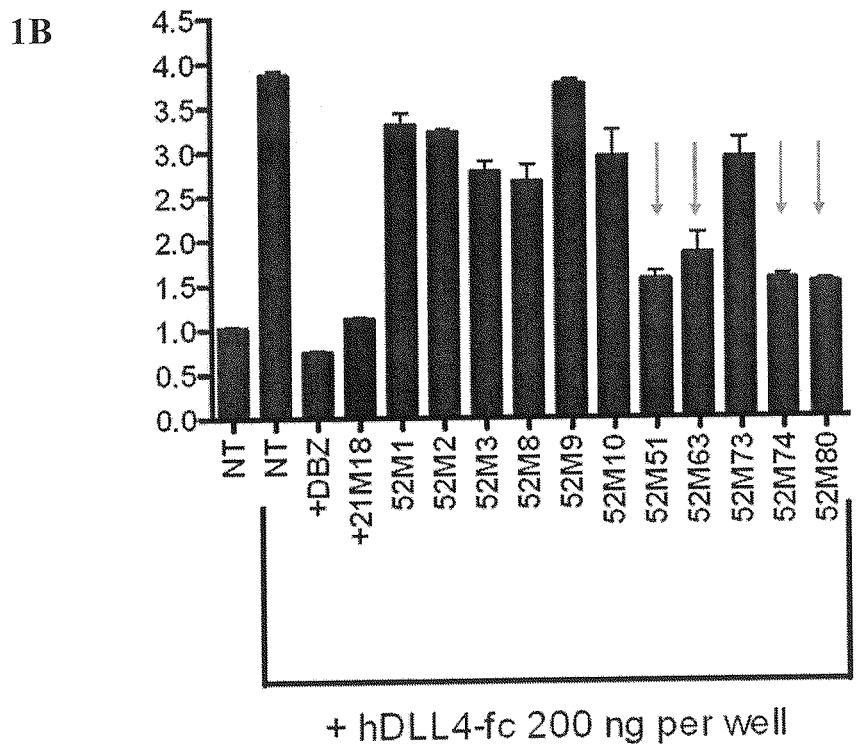
Figure 1:
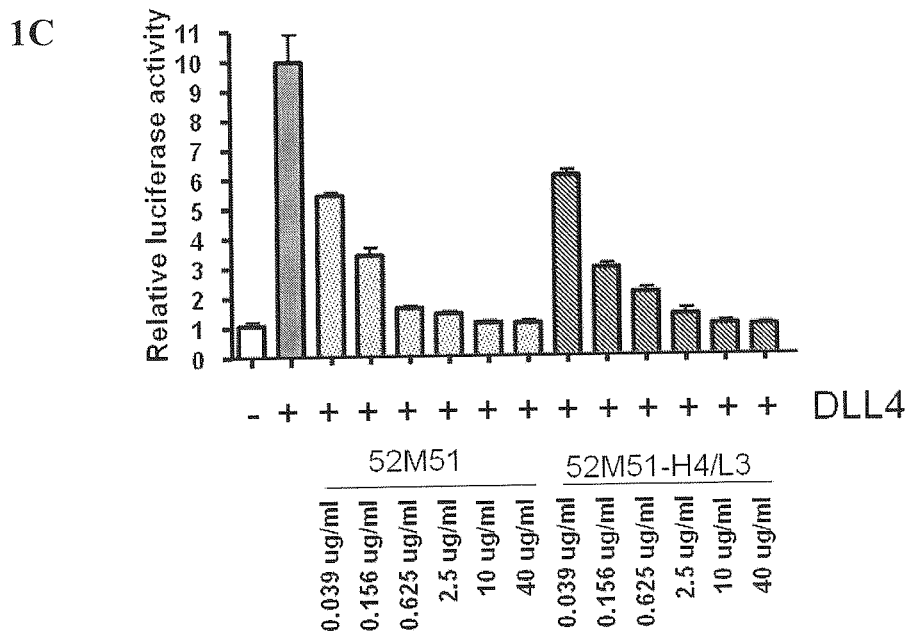
Figure 1:
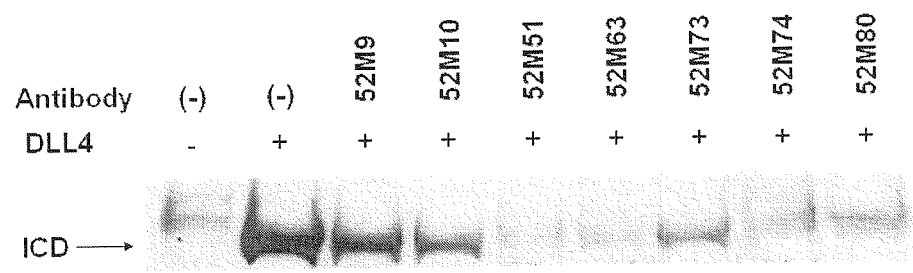

Monoclonal antibodies that specifically bind to the membrane proximal region of the extracellular domain of Notch1, including the monoclonal antibody 52M51, have been identified (Example 1). Humanized 52M51 antibodies have been generated (Example 2). Several of the antibodies, including 52M51 and a humanized variant of 52M51, inhibit ligand-induced Notch1 signaling (Example 3 and FIGS. 1B and C), despite binding to Notch1 in a region outside of the ligand-binding region. The ability of several of the antibodies to inhibit formation of the Notch intracellular domain (ICD) has been demonstrated (Examples 3 and 7; FIGS. 1D and 5). 52M51 was shown to inhibit solid tumor growth of HPB-ALL cells (Example 8 and FIG. 6). 52M51 was shown to reduce cell viability and proliferation of human leukemia cells in vitro (Examples 5 and 6; FIGS. 3 and 4). 52M51 has been found to inhibit leukemic cell engraftment in vivo in two xenograft models (Example 4 and 9; FIGS. 2 and 7).

I. Definitions

To facilitate an understanding of the present invention, a number of terms and phrases are defined below.

The term "antagonist" as used herein refers to any molecule that partially or fully blocks, inhibits, or neutralizes a biological activity of the Notch pathway. The term "antagonist" is used herein to include any molecule that partially or fully blocks, inhibits, or neutralizes the expression of a Notch receptor. Suitable antagonist molecules specifically include antagonist antibodies or antibody fragments.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies such as bispecific antibodies generated from at least two intact antibodies, monospecific antibodies, monovalent antibodies, chimeric antibodies, humanized antibodies, human antibodies, fusion proteins comprising an antigen determination portion of an antibody, and any other modified immunoglobulin molecule comprising an antigen recognition site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments.

The term "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding site of antibodies. There are at least two techniques for determining CDRs: (1) an approach based on cross-species sequence variability (i.e., Kabat et al., 1991, Sequences of Proteins of Immunological Interest, 5$^{th}$ ed., National Institutes of Health, Bethesda Md.), and (2) an approach based on crystallographic studies of antigen-antibody complexes (Al-Lazikani et al., 1997, *J. Molec. Biol.*, 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen recognition site. Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences.

The term "human antibody" as used herein refers to an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or capability, while the constant regions are homologous to the sequences in antibodies derived from another species (usually human) to avoid eliciting an immune response in that species.

The teems "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "selectively binds" or "specifically binds" mean that a binding agent or an antibody reacts or associates more frequently, more rapidly, with greater duration, with greater affinity, or with some combination of the above to the epitope, protein or target molecule than with alternative substances, including unrelated proteins. In certain embodiments "specifically binds" means, for instance, that an antibody binds a protein with a $K_D$ of about 0.1 mM or less, but more usually less than about 1 uM. In certain embodiments, "specifically binds" means that an antibody binds a target at times with a $K_D$ of at least about 0.1 µM or less and at other times at least about 0.01 µM or less. Because of the sequence identity between homologous proteins in different species, specific binding can include an antibody that recognizes a protein (e.g., a Notch receptor) in more than one species. Likewise, because of homology within certain regions of polypeptide sequences of different proteins, specific binding can include an antibody (or other polypeptide or binding agent) that recognizes more than one protein (e.g., human Notch1 and human Notch2). It is understood that, in certain embodiments, an antibody or binding moiety that specifically binds a first target may or may not specifically bind to a second target. As such, "specific binding" does not necessarily require (although it can include) exclusive binding, i.e. binding to a single target. Thus, an antibody may, in certain embodiments, specifically bind to more than one target (e.g., human Notch1, human Notch2, human Notch3, and/or mouse Notch). In certain embodiments, the multiple targets may be bound by the same antigen-binding site on the antibody. For example, an antibody may, in certain instances, comprise two identical antigen-binding sites, each of which specifically binds the same epitope on two or more proteins (e.g., Notch1 and Notch2). In certain alternative embodiments, an antibody may be bispecific and comprise at least two antigen-binding sites with differing specificities. By way of non-limiting example, a bispecific antibody may comprise one antigen-binding site that recognizes an epitope on one protein (e.g., human Notch1) and further comprises a second, different antigen-binding site that recognizes a different epitope on a second protein (e.g., human Notch2). Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention are based upon antibodies, in certain embodiments, the polypeptides can occur as single chains or associated chains.

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (1) employ low ionic strength and high temperature for washing, for example 0.015M sodium chloride/0.0015M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include but are not limited to, BLAST, ALIGN, Megalign, BestFit, GCG Wisconsin Package, etc. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues in length or any integral value therebetween. In some embodiments, identity exists over a longer region than 60-80 residues, such as at least about 90-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s), i.e., the one or more Notch proteins to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions.

The terms "proliferative disorder" and "proliferative disease" refer to disorders associated with abnormal cell proliferation such as cancer.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" are used interchangeably herein and refer to cells from a cancer that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur. "Cancer stem cell" as used herein may comprise leukemia-initiating cells.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein of a tumor refers to the ability of a random sample of cells from the tumor to form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to approved or approvable by a regulatory agency of the Federal or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the pharmacological activity thereof and is nontoxic when administered in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an", and "the" include plural forms unless the context clearly dictates otherwise.

It is understood that wherever embodiments are described herein with the language "comprising" otherwise analogous embodiments described in terms of "consisting of" and/or "consisting essentially of" are also provided.

The term "and/or" as used in a phrase such as "A and/or B" herein is intended to include: both A and B; A or B; A (alone); and B alone. Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Notch1 Binding Agents

The present invention provides agents that specifically bind to a non-ligand binding membrane proximal region of the extracellular domain of human Notch1, compositions comprising those binding agents and methods for using those binding agent to treat hematologic cancers. In particular, in certain embodiments, the present invention provides agents, including antagonists, that bind Notch1 and methods of using the agents or antagonists to inhibit cancer growth and treat cancer or other diseases in human patients. In certain embodiments, the antagonists are antibodies that specifically bind to a non-ligand binding region of the extracellular domain of human Notch1.

In one aspect, the present invention provides a binding agent that specifically binds a non-ligand binding membrane proximal region of the extracellular domain of human Notch1. In some embodiments, the binding agent is an antibody. In some embodiments, the binding agent or antibody binds a region of human Notch1 comprising about amino acid 1427 to about amino acid 1732. In some embodiments, the binding agent or antibody binds a region comprising SEQ ID NO:2. In some embodiments, the binding agent or antibody specifically binds a region within SEQ ID NO:2. In some embodiments, the binding agent or antibody specifically binds an epitope within a region comprising SEQ ID NO:2. In certain embodiments, the binding agent or antibody that binds Notch1 also specifically binds a non-ligand binding membrane proximal region of the extracellular domain of at least one additional Notch receptor. In some embodiments, the at least one additional Notch receptor is Notch2. In some embodiments, the at least one additional Notch receptor is Notch3. In some embodiments, the at least one additional Notch receptor is Notch4.

In certain embodiments, the Notch1 binding agent is a polypeptide. In certain embodiments, the Notch1 binding agent or polypeptide is an antibody. In certain embodiments, the antibody is an IgG antibody. In some embodiments, the antibody is an IgG1 antibody. In some embodiments, the antibody is an IgG2 antibody. In certain embodiments, the antibody is a monoclonal antibody. In certain embodiments, the antibody is a humanized antibody. In certain embodiments, the antibody is a human antibody. In certain embodiments, the antibody is an antibody fragment.

In certain embodiments, the Notch1 binding agent (e.g., an antibody) binds a non-ligand binding membrane proximal region of the extracellular domain of human Notch1 with a dissociation constant ($K_D$) of about 1 μM or less, about 100 nM or less, about 40 nM or less, about 20 nM or less, about 10 nM or less or about 1 nM or less. In certain embodiments, the Notch1 binding agent or antibody binds human Notch1 with a $K_D$ of about 40 nM or less, about 20 nM or less, about 10 nM or less, or about 1 nM or less. In some embodiments, the dissociation constant of the agent or antibody to Notch1 is a dissociation constant determined using a Notch1 fusion protein comprising a proximal region of the Notch1 extracellular domain immobilized on a Biacore chip.

The Notch1 binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well-known in the art (see, e.g., Ausubel et al., Eds., 1994, Current Protocols in Molecular Biology, Vol. 1, John Wiley & Sons, Inc., New York).

In some embodiments, the specific binding of a Notch1 binding agent (e.g., an antibody) to a human Notch1 may be determined using ELISA. In some embodiments, an ELISA assay comprises preparing Notch1 antigen, coating wells of a 96-well microtiter plate with antigen, adding to the wells the Notch1 binding agent or antibody conjugated to a detectable compound such as an enzymatic substrate (e.g., horseradish peroxidase or alkaline phosphatase), incubating for a period of time and detecting the presence of the binding agent or antibody. In some embodiments, the Notch1 binding agent or antibody is not conjugated to a detectable compound, but instead a second conjugated antibody that recognizes the Notch1 binding agent or antibody is added to the well. In some embodiments, instead of coating the well with the Notch1 antigen, the Notch1 binding agent or antibody can be coated to the well, antigen is added to the coated well and then a second antibody conjugated to a detectable compound is added. One of skill in the art would be knowledgeable as to the parameters that can be modified and/or optimized to increase the signal detected, as well as other variations of ELISAs that can be used (see e.g., Ausubel et al., Eds., 1994, Current Protocols in Molecular Biology, Vol. 1, John Wiley & Sons, Inc., New York at 11.2.1).

The binding affinity of an antibody or other binding agent to Notch1 and the on-off rate of an antibody-antigen interaction can be determined by competitive binding assays. In some embodiments, a competitive binding assay is a radioimmunoassay comprising the incubation of labeled antigen (e.g., $^3$H— or $^{125}$I-labeled antigen), or fragment or variant thereof, with the antibody of interest in the presence of increasing amounts of unlabeled antigen followed by the detection of the antibody bound to the labeled antigen. The affinity of the antibody for the antigen and the on-off rates can be determined from the data by Scatchard plot analysis. In some embodiments, Biacore kinetic analysis is used to determine the binding affinities and on-off rates of antibodies or agents that bind Notch (e.g., human Notch1, human Notch2, human Notch3, human Notch 4 or mouse Notch). Biacore kinetic analysis comprises analyzing the binding and dissociation of antibodies from antigens (e.g., Notch1 proteins) that have been immobilized on the surface of a Biacore chip. In some embodiments, Biacore kinetic analyses can be used to study binding of different antibodies in qualitative epitope competition binding assays.

In certain embodiments, the invention provides an antibody that specifically binds a non-ligand binding membrane proximal region of the extracellular domain of human Notch1, wherein the antibody comprises one, two, three, four, five and/or six of the CDRs of antibody 52M51 (see Table 1). In some embodiments, the antibody comprises one or more of the CDRs of 52M51, two or more of the CDRs of 52M51, three or more of the CDRs of 52M51, four or more of the CDRs of 52M51, five or more of the CDRs of 52M51, or all six of the CDRs or 52M51. In some embodiments, the antibody comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

TABLE 1

| | 52M51 |
|---|---|
| HC CDR1 | RGYWIE, (SEQ ID NO: 15) |
| HC CDR2 | QILPGTGRTNYNEKFKG (SEQ ID NO: 16) |
| HC CDR3 | FDGNYGYYAMDY (SEQ ID NO: 17) |
| LC CDR1 | RSSTGAVTTSNYAN (SEQ ID NO: 18) |
| LC CDR2 | GTNNRAP (SEQ ID NO: 19) |
| LC CDR3 | ALWYSNHWVFGGGTKL (SEQ ID NO: 20) |

In certain embodiments, the binding agent is an antibody comprising (a) a heavy chain CDR1 comprising RGYWIE (SEQ ID NO:15), a heavy chain CDR2 comprising QILPGT-GRTNYNEKFKG (SEQ ID NO:16), and/or a heavy chain CDR3 comprising FDGNYGYYAMDY (SEQ ID NO:17); and/or (b) a light chain CDR1 comprising RSSTGAVTTSN-YAN (SEQ ID NO:18), a light chain CDR2 comprising GTNNRAP (SEQ ID NO:19), and/or a light chain CDR3 comprising ALWYSNHWVFGGGTKL (SEQ ID NO:20). In some embodiments, the antibody comprises a heavy chain variable region comprising: (a) a heavy chain CDR1 comprising RGYWIE (SEQ ID NO:15), or a variant thereof comprising 1, 2, 3, or 4 amino acid substitutions; (b) a heavy chain CDR2 comprising QILPGTGRTNYNEKFKG (SEQ ID NO:16), or a variant thereof comprising 1, 2, 3, or 4 amino acid substitutions; and/or (c) a heavy chain CDR3 comprising FDGNYGYYAMDY (SEQ ID NO:17), or a variant thereof comprising 1, 2, 3, or 4 amino acid substitutions. In other embodiments, the antibody comprises (or further comprises) a light chain variable region comprising: (a) a light chain CDR1 comprising RSSTGAVTTSNYAN (SEQ ID NO:18), or a variant thereof comprising 1, 2, 3, or 4 amino acid substitutions; (b) a light chain CDR2 comprising GTNNRAP (SEQ ID NO:19), or a variant thereof comprising 1, 2, 3, or 4 amino acid substitutions; and/or (c) a light chain CDR3 comprising ALWYSNHWVFGGGTKL (SEQ ID NO:20), or a variant thereof comprising 1, 2, 3, or 4 amino acid substitutions. In some embodiments, the amino acid substitutions are conservative amino acid substitutions.

In some embodiments, the Notch1 binding agent is an antibody that specifically binds a non-ligand binding membrane proximal region of the extracellular domain of human Notch1. In some embodiments, the antibody comprises a heavy chain variable region having at least about 90% sequence identity to SEQ ID NO:14, and/or a light chain variable region having at least about 90% sequence identity to SEQ ID NO:8. In some embodiments, the antibody comprises a heavy chain variable region having at least about 95%, at least about 97%, or at least about 99% sequence identity to SEQ ID NO:14, and/or a light chain variable region having at least about 95%, at least about 97%, or at least about 99% sequence identity to SEQ ID NO:8. In some embodiments, the antibody comprises a heavy chain variable region having at least about 95% sequence identity to SEQ ID NO:14, and/or a light chain variable region having at least about 95% sequence identity to SEQ ID NO:8. In some embodiments, the antibody comprises a heavy chain variable region comprising SEQ ID NO:14, and/or a light chain variable region comprising SEQ ID NO:8. In some embodiments, the antibody comprises a heavy chain variable region comprising SEQ ID NO:14, and a light chain variable region comprising SEQ ID NO:8. In some embodiments, the antibody is a monoclonal antibody or antibody fragment.

In some embodiments, the Notch1 binding agent is an antibody that specifically binds a non-ligand binding membrane proximal region of the extracellular domain of human Notch1. In some embodiments, the antibody comprises a heavy chain variable region having at least about 90% sequence identity to SEQ ID NO:24, and/or a light chain variable region having at least about 90% sequence identity to SEQ ID NO:28. In some embodiments, the antibody comprises a heavy chain variable region having at least about 95%, at least about 97%, or at least about 99% sequence identity to SEQ ID NO:24, and/or a light chain variable region having at least about 95%, at least about 97%, or at least about 99% sequence identity to SEQ ID NO:28. In some embodiments, the antibody comprises a heavy chain variable region having at least about 95% sequence identity to SEQ ID NO:24, and/or a light chain variable region having at least about 95% sequence identity to SEQ ID NO:28. In some embodiments, the antibody comprises a heavy chain variable region comprising SEQ ID NO:24, and/or a light chain variable region comprising SEQ ID NO:28. In some embodiments, the antibody comprises a heavy chain variable region comprising SEQ ID NO:24, and a light chain variable region comprising SEQ ID NO:28. In some embodiments, the antibody is a monoclonal antibody or antibody fragment.

In some embodiments, the Notch1 binding agent is an antibody that specifically binds a non-ligand binding membrane proximal region of the extracellular domain of human Notch1. In some embodiments, the antibody comprises a heavy chain variable region having at least about 90% sequence identity to SEQ ID NO:24, and/or a light chain variable region having at least about 90% sequence identity to SEQ ID NO:32. In some embodiments, the antibody comprises a heavy chain variable region having at least about 95%, at least about 97%, or at least about 99% sequence identity to SEQ ID NO:24, and/or a light chain variable region having at least about 95%, at least about 97%, or at least about 99% sequence identity to SEQ ID NO:32. In some embodiments, the antibody comprises a heavy chain variable region having at least about 95% sequence identity to SEQ ID NO:24, and/or a light chain variable region having at least about 95% sequence identity to SEQ ID NO:32. In some embodiments, the antibody comprises a heavy chain variable region comprising SEQ ID NO:24, and/or a light chain variable region comprising SEQ ID NO:32. In some embodiments, the antibody comprises a heavy chain variable region comprising SEQ ID NO:24, and a light chain variable region comprising SEQ ID NO:32. In some embodiments, the antibody is a monoclonal antibody or antibody fragment.

In some embodiments, the Notch1 binding agent is an antibody, 52M51, produced by the hybridoma cell line deposited with the ATCC under the conditions of the Budapest Treaty on Aug. 7, 2008 and assigned number PTA-9405. In some embodiments, the antibody is a humanized version of 52M51. In some embodiments, the antibody is a humanized version of 52M51, "52M51H4L3", as encoded by the DNA deposited with the ATCC under the conditions of the Budapest Treaty on Oct. 15, 2008 and assigned number PTA-9549. In some embodiments, the antibody is a humanized version of 52M51, "52M51H4L4". In some embodiments, the invention provides an antibody that binds the same epitope as the epitope to which antibody 52M51 binds. In other embodiments, the invention provides an antibody that competes with any of the antibodies as described in the aforementioned embodiments and/or aspects, as well as other aspects/embodiments described elsewhere herein, for specific binding to a non-ligand binding membrane proximal region of the extracellular domain of human Notch1.

The invention provides a variety of polypeptides, including but not limited to, antibodies and fragments of antibodies. In certain embodiments, the polypeptide is isolated. In certain alternative embodiments, the polypeptide is substantially pure.

In certain embodiments, the polypeptides of the present invention can be recombinant polypeptides, natural polypeptides, or synthetic polypeptides comprising the sequence of SEQ ID NO:8, SEQ ID NO:14, SEQ ID NO:24, SEQ ID NO:28, or SEQ ID NO:32 (with or without the signal/leader sequences). In some embodiments, the polypeptides comprise the heavy chain and/or the light chain provided in SEQ ID NO:10 and/or SEQ ID NO:4, respectively (with or without the signal/leader signal sequences). In certain embodiments, the polypeptide is an antibody. In certain embodiments, the polypeptide specifically binds a non-ligand binding membrane proximal region of the extracellular domain of human Notch1. In certain embodiments, the polypeptide comprises a variable light chain sequence comprising SEQ ID NO:8 and a variable heavy chain sequence comprising SEQ ID NO:14. In certain embodiments, the polypeptide comprises a variable light chain sequence comprising SEQ ID NO:28 and a variable heavy chain sequence comprising SEQ ID NO:24. In certain embodiments, the polypeptide comprises a variable light chain sequence comprising SEQ ID NO:32 and a variable heavy chain sequence comprising SEQ ID NO:24. In certain embodiments, the polypeptide is an antibody. In certain embodiments, the polypeptide specifically binds a non-ligand binding membrane proximal region of the extracellular domain of human Notch1.

The polypeptides of the present invention include the polypeptides of SEQ ID NO:14 as well as polypeptides which have at least 90% sequence identity to the polypeptides of SEQ ID NO:14 and at least 95% sequence identity to the polypeptides of SEQ ID NO:14, and in still other embodiments, polypeptide which have at least 96%, 97%, 98%, or 99% sequence identity to the polypeptides of SEQ ID NO:14. The polypeptides of the present invention include the polypeptides of SEQ ID NO:8 as well as polypeptides which have at least 90% sequence identity to the polypeptides of SEQ ID NO:8 and at least 95% sequence identity to the polypeptides of SEQ ID NO:8, and in still other embodiments, polypeptide which have at least 96%, 97%, 98%, or 99% sequence identity to the polypeptides of SEQ ID NO:8. The polypeptides of the present invention include the polypeptides of SEQ ID NO:24 as well as polypeptides which have at least 90% sequence identity to the polypeptides of SEQ ID NO:24 and at least 95% sequence identity to the polypeptides of SEQ ID NO:24, and in still other embodiments, polypeptide which have at least 96%, 97%, 98%, or 99% sequence identity to the polypeptides of SEQ ID NO:24. The polypeptides of the present invention include the polypeptides of SEQ ID NO:28 as well as polypeptides which have at least 90% sequence identity to the polypeptides of SEQ ID NO:28 and at least 95% sequence identity to the polypeptides of SEQ ID NO:28, and in still other embodiments, polypeptide which have at least 96%, 97%, 98%, or 99% sequence identity to the polypeptides of SEQ ID NO:28. The polypeptides of the present invention include the polypeptides of SEQ ID NO:32 as well as polypeptides which have at least 90% sequence identity to the polypeptides of SEQ ID NO:32 and at least 95% sequence identity to the polypeptides of SEQ ID NO:32, and in still other embodiments, polypeptide which have at least 96%, 97%, 98%, or 99% sequence identity to the polypeptides of SEQ ID NO:32.

In certain embodiments, the Notch1 binding agent (e.g., an antibody) binds Notch1 and modulates Notch1 activity. In some embodiments, the Notch1 binding agent is an antagonist and modulates Notch1 activity.

In certain embodiments, the Notch1 binding agent (e.g., an antibody) is an antagonist of Notch1 and inhibits Notch1 activity. In certain embodiments, the Notch1 binding agent inhibits at least about 10%, at least about 20%, at least about 30%, at least about 50%, at least about 75%, at least about 90%, or about 100% of the activity of the bound human Notch1. In some embodiments, the Notch1 binding agent inhibits activity of a constitutively activated Notch1. In some embodiments, the constitutively activated Notch1 is expressed in a hematologic cancer. In certain embodiments, the constitutively activated Notch1 is expressed in a T-cell acute lymphoblastic leukemia.

In certain embodiments, the Notch1 binding agent (e.g., an antibody) inhibits Notch signaling. It is understood that a Notch1 binding agent that inhibits Notch signaling may, in certain embodiments, inhibit signaling by one or more Notchs, but not necessarily inhibit signaling by all Notchs. In certain alternative embodiments, signaling by all human Notchs may be inhibited. In certain embodiments, signaling by one or more Notchs selected from the group consisting of Notch1, Notch2, Notch3 and Notch4 is inhibited. In certain embodiments, the inhibition of Notch signaling by a Notch1 binding agent is a reduction in the level of Notch1 signaling of at least about 10%, at least about 25%, at least about 50%, at least about 75%, at least about 90%, or at least about 95%.

In certain embodiments, the Notch1 binding agent (e.g., an antibody) inhibits Notch activation. It is understood that a Notch1 binding agent that inhibits Notch activation may, in certain embodiments, inhibit activation of one or more Notchs, but not necessarily inhibit activation of all Notchs. In certain alternative embodiments, activation of all human Notchs may be inhibited. In certain embodiments, activation of one or more Notchs selected from the group consisting of Notch1, Notch2, Notch3 and Notch4 is inhibited. In certain embodiments, the inhibition of Notch activation by a Notch1 binding agent is a reduction in the level of Notch1 activation of at least about 10%, at least about 25%, at least about 50%, at least about 75%, at least about 90%, or at least about 95%.

In vivo and in vitro assays for determining whether a Notch1 binding agent (or candidate Notch1 binding agent) inhibits Notch activation are known in the art. In some embodiments, a cell-based, luciferase reporter assay utilizing a TCF/Luc reporter vector containing multiple copies of the TCF-binding domain upstream of a firefly luciferase reporter gene may be used to measure Notch signaling levels in vitro. In other embodiments, a cell-based, luciferase reporter assay utilizing a CBF/Luc reporter vector containing multiple copies of the CBF-binding domain upstream of a firefly luciferase reporter gene may be used. The level of Notch activation induced by a Notch ligand in the presence of a Notch1 binding agent is compared to the level of Notch activation induced by a Notch ligand in the absence of a Notch1 binding agent. Non-limiting, specific examples of the use of such luciferase reporter assays to assess inhibition of Notch activation are provided in Example 3 and FIGS. 1B and 1C.

In certain embodiments, the Notch1 binding agents (e.g., antibodies) have one or more of the following effects: inhibit proliferation of cancer cells, inhibit cancer cell growth, prevent or reduce metastasis of cancer cells, reduce the frequency of cancer stem cells in a tumor or cancer, trigger cell death of cancer cells (e.g., by apoptosis), reduce the tumorigenicity of cancer cells by reducing the frequency of cancer stem cells in the cancer cell population, differentiate tumorigenic cells to a non-tumorigenic state, or increase survival of a patient.

In certain embodiments, the Notch1 binding agents (e.g., antibodies) are capable of inhibiting cancer cell growth. In certain embodiments, the Notch1 binding agents are capable of inhibiting growth of cancer cells in vitro (e.g., contacting cancer cells with an antibody in vitro). In certain embodiments, the Notch1 binding agents are capable of inhibiting cancer growth in vivo (e.g., in a xenograft mouse model and/or in a human having cancer).

In certain embodiments, the Notch1 binding agents (e.g., antibodies) are capable of reducing the tumorigenicity of a hematologic cancer. In certain embodiments, the Notch1 binding agent or antibody is capable of reducing the tumorigenicity of a hematologic cancer comprising cancer stem cells in an animal model, such as a mouse xenograft model. In certain embodiments, the Notch1 binding agent or antibody is capable of reducing the tumorigenicity of a hematologic cancer comprising leukemia initiating cells in an animal model, such as a mouse xenograft model. In some embodiments, the Notch1 binding agent is capable of reducing the tumorigenicity of a hematologic cancer by reducing the frequency of cancer stem cells in the cancer. In certain embodiments, the number or frequency of cancer stem cells in a cancer is reduced by at least about two-fold, about three-fold, about five-fold, about ten-fold, about 50-fold, about 100-fold, or about 1000-fold. In certain embodiments, the reduction in the frequency of cancer stem cells is determined by a limiting dilution assay (LDA) using an animal model. Examples and guidance regarding the use of limiting dilution assays to determine a reduction in the number or frequency of cancer stem cells in a tumor can be found, e.g., in International Pub. No. WO 2008/042236 and U.S. Patent Pub. Nos. 2008/0064049 and 2008/0178305.

In certain embodiments, Notch1 binding agents or antibodies mediate cell death of a cell expressing Notch1 via antibody-dependent cellular cytotoxicity (ADCC). ADCC involves cell lysis by effector cells that recognize the Fc portion of an antibody. Many lymphocytes, monocytes, tissue macrophages, granulocytes and eosinophils, for example, have Fc receptors and can mediate cytolysis (Dillman, 1994, J. Clin. Oncol., 12:1497).

In some embodiments, Notch1 binding agents or antibodies trigger cell death of cell expressing a Notch1 receptor by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, 1984, Textbook of Immunology, 2nd Edition, Williams & Wilkins, p. 218). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, J. Clin. Oncol. 12:1497; Jefferis et al., 1998, Immunol. Rev. 163:59-76). According to the present invention, antibodies of those classes having the desired biological activity can be prepared.

The ability of any particular Notch1 binding agent or antibody to mediate lysis of the target cell by CDC and/or ADCC can be assayed. In some embodiments, the cells of interest are grown and labeled in vitro (target cells) and the antibody is added to the cell culture in combination with either serum complement or immune cells which can be activated by the antigen antibody complexes. Cytolysis of the target cells is detected, for example, by the release of label from the lysed cells. In some embodiments, antibodies can be screened using a patient's own serum as a source of complement and/or immune cells. The antibody that is capable of activating complement or mediating ADCC in the in vitro test can then be used therapeutically in that particular patient.

In certain embodiments, the Notch1 binding agent (e.g., an antibody) has a circulating half-life in a subject or mammal (e.g., mice, rats, cynomolgus monkeys, or humans) of at least about 5 hours, at least about 10 hours, at least about 24 hours, at least about 3 days, at least about 1 week, or at least about 2 weeks. In certain embodiments, the Notch1 binding agent is an IgG (e.g., IgG1 or IgG2) antibody that has a circulating half-life in a subject or mammal (e.g., mice, rats, cynomolgus monkeys, or humans) of at least about 5 hours, at least about 10 hours, at least about 24 hours, at least about 3 days, at least about 1 week, or at least about 2 weeks. Methods of increasing the half-life of agents such as polypeptides and antibodies are known in the art. In some embodiments, known methods of increasing the circulating half-life of IgG antibodies include the introduction of mutations in the Fc region which increase the pH-dependent binding of the antibody to the neonatal Fc receptor (FcRn) at pH 6.0 (see e.g., U.S. Patent Pub. Nos. 2005/0276799; 2007/0148164; and 2007/0122403). Known methods of increasing the circulating half-life of antibody fragments lacking the Fc region include, but are not limited to, techniques such as PEGylation.

In some embodiments, the Notch1 binding agents are polyclonal antibodies. Polyclonal antibodies can be prepared by any known method. In some embodiments, polyclonal antibodies are raised by immunizing an animal (e.g. a rabbit, rat, mouse, goat, donkey) by multiple subcutaneous or intraperitoneal injections of the relevant antigen (e.g., a purified peptide fragment, full-length recombinant protein, or fusion protein). The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from blood, ascites and the like, of the immunized animal. The polyclonal antibodies can be purified from serum or ascites according to standard methods in the art including, but not limited to, affinity chromatography, ion-exchange chromatography, gel electrophoresis, and dialysis.

In some embodiments, the Notch1 binding agents are monoclonal antibodies. Monoclonal antibodies can be prepared using hybridoma methods known to one of skill in the art (see e.g., Kohler and Milstein, 1975, Nature 256:495-497). In some embodiments, using the hybridoma method, a mouse, hamster, or other appropriate host animal, is immunized as described above to elicit from lymphocytes the production of antibodies that will specifically bind to the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol, to fowl hybridoma cells that can then be selected away from unfused lymphocytes and myeloma cells. Hybridomas that produce monoclonal antibodies directed specifically against a chosen antigen may be identified by a variety of methods including, but not limited to, immunoprecipitation, immunoblotting, and in vitro binding assay (e.g., flow cytometry, enzyme-linked immunosorbent assay (ELISA), and radioimmunoassay (RIA)). The hybridomas can be propagated either in in vitro culture using standard methods (Goding, Monoclonal Antibodies: Principles and Practice, Academic Press, 1986) or in in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art (see e.g., U.S. Pat. No. 4,816,567). The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin protein. In other embodiments, recombinant monoclonal antibodies, or fragments thereof, can be isolated from phage display libraries expressing CDRs of the desired species (see e.g., McCafferty et al., 1990, *Nature*, 348:552-554; Clackson et al., 1991, *Nature*, 352:624-628; and Marks et al., 1991, *J. Mol. Biol.*, 222:581-597).

The polynucleotide(s) encoding a monoclonal antibody can further be modified using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Site-directed or high-density mutagenesis of the variable region can be used to optimize specificity, affinity, and/or other biological characteristics of a monoclonal antibody. In some embodiments, site-directed mutagenesis of the CDRs can be used to optimize specificity, affinity, and/or other biological characteristics of a monoclonal antibody.

In some embodiments, the Notch1 binding agent is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or capability using methods known to one skilled in the art. In some embodiments, the Fv framework region residues of a human immunoglobulin are replaced with the corresponding residues in an antibody from a non-human species that has the desired specificity, affinity, and/or capability. In some embodiments, the humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all, or substantially all, of the CDR regions that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see e.g., U.S. Pat. Nos. 5,225,539; 5,585,089; 5,693,761; and 5,693,762).

In certain embodiments, the Notch1 binding agent is a human antibody. Human antibodies can be directly prepared using various techniques known in the art. In some embodiments, immortalized human B lymphocytes immunized in vitro or isolated from an immunized individual that produces an antibody directed against a target antigen can be generated (see, e.g., Cole et al., *Monoclonal Antibodies and Cancer Therapy*, Alan R. Liss, p. 77 (1985); Boerner et al., 1991, *J. Immunol.*, 147 (1):86-95; and U.S. Pat. Nos. 5,750,373; 5,567,610 and 5,229,275). In some embodiments, the human antibody can be selected from a phage library, where that phage library expresses human antibodies (Vaughan et al., 1996, *Nature Biotechnology*, 14:309-314; Sheets et al., 1998, *PNAS*, 95:6157-6162; Hoogenboom and Winter, 1991, *J. Mol. Biol.*, 227:381; Marks et al., 1991, *J. Mol. Biol.*, 222:581). Alternatively, phage display technology can be used to produce human antibodies and antibody fragments in vitro, from immunoglobulin variable (V) domain gene repertoires from unimmunized donors. Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200. Affinity maturation strategies, such as chain shuffling (Marks et al., 1992, *Bio/Technology*, 10:779-783), are known in the art and may be employed to generate high affinity human antibodies.

In some embodiments, human antibodies can be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In some embodiments, the Notch1 binding agent is a bispecific antibody. Bispecific antibodies are capable of specifically recognizing and binding at least two different epitopes. The different epitopes can either be within the same molecule or on different molecules. In some embodiments, the bispecific antibodies are monoclonal human or humanized antibodies. In some embodiments, the antibodies can specifically recognize and bind a first antigen target, (e.g., Notch1) as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen, such as Notch1. These antibodies possess an antigen-binding aim and an aim which binds a cytotoxic agent or a radionuclide chelator, such as EOTUBE, DPTA, DOTA, or TETA. In certain embodiments, the bispecific antibody specifically binds Notch1, as well as at least one additional Notch receptor selected from the group consisting of Notch2, Notch3, and Notch4 or a Notch ligand selected from the group consisting of Jagged1, Jagged2, DLL1, DLL3 and DLL4.

Techniques for making bispecific antibodies are known by those skilled in the art, see for example, Millstein et al., 1983, *Nature*, 305:537-539; Brennan et al., 1985, *Science*, 229:81; Suresh et al., 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.*, 148:1547-1553; Gruber et al., 1994, *J. Immunol.*, 152:5368; and U.S. Pat. No. 5,731,168). Bispecific antibodies can be intact antibodies or antibody fragments. Antibodies with more than two valencies are also contemplated. For example, trispecific antibodies can be prepared (Tutt et al., 1991, *J. Immunol.*, 147:60). Thus, in certain embodiments the antibodies to Notch1 are multispecific.

In certain embodiments, the Notch1 binding agent or antibody described herein may be monospecific. For example, in certain embodiments, each of the one or more antigen-binding sites that an antibody contains is capable of binding (or binds) a homologous epitope on Notch1. In certain embodiments, an antigen-binding site of a monospecific antibody described herein is capable of binding (or binds) Notch1 and a second Notch such as Notch2, Notch3 or Notch4 (i.e., the same epitope is found on Notch1 and, for example, on Notch2).

In certain embodiments, the Notch1 binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from E. coli or other host cells, allowing for the production of large amounts of these fragments. In some embodiments, antibody fragments are isolated from antibody phage libraries as discussed herein. For example, methods can be used for the construction of Fab expression libraries (Huse et al., 1989, Science, 246:1275-1281) to allow rapid and effective identification of monoclonal Fab fragments with the desired specificity for a Notch1 protein or derivatives, fragments, analogs or homologs thereof. In some embodiments, antibody fragments are linear antibody fragments as described in U.S. Pat. No. 5,641,870. In certain embodiments, antibody fragments are monospecific or bispecific. In certain embodiments, the Notch1 binding agent is a scFv. Various techniques can be used for the production of single-chain antibodies specific to Notch1 (see, e.g., U.S. Pat. No. 4,946,778).

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

For the purposes of the present invention, it should be appreciated that modified antibodies, or fragments thereof, can comprise any type of variable region that provides for the association of the antibody with a membrane proximal region of the extracellular domain of Notch1. In this regard, the variable region may be derived from any type of mammal that can be induced to mount a humoral response and generate immunoglobulins against a desired antigen (e.g., Notch1). As such, the variable region of the modified antibodies can be, for example, of human, murine, non-human primate (e.g. cynomolgus monkeys, macaques, etc.) or lupine origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In some embodiments, the variable domains in both the heavy and light chains are altered by at least partial replacement of one or more CDRs and, if necessary, by partial framework region replacement and sequence modification. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen binding site.

Alterations to the variable region notwithstanding, those skilled in the art will appreciate that the modified antibodies of this invention may comprise antibodies (e.g., full-length antibodies or antigen-binding fragments thereof) in which at least a fraction of one or more of the constant region domains has been deleted or otherwise altered so as to provide desired biochemical characteristics, such as increased cancer cell localization, increased tumor penetration, reduced serum half-life or increased serum half-life, when compared with an antibody of approximately the same immunogenicity comprising a native or unaltered constant region. In some embodiments, the constant region of the modified antibodies comprises a human constant region. Modifications to the constant region include additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In other embodiments, the entire CH2 domain is removed (ΔCH2 constructs). In some embodiments, the omitted constant region domain is replaced by a short amino acid spacer (e.g., 10 aa residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete that part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (ADCC), release of inflammatory mediators, placental transfer and control of immunoglobulin production.

In some embodiments, the Notch1 binding agents or antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody (e.g., Notch1 antibody) thereby increasing cancer cell localization and/or tumor penetration. In other embodiments, the constant region modifications increase or reduce the serum half-life of the antibody. In some embodiments, the constant region is modified to eliminate disulfide linkages or oligosaccharide moieties allowing for enhanced cancer cell localization.

In certain embodiments, a Notch1 binding agent or antibody does not have one or more effector functions. In some embodiments, the antibody has no ADCC activity, and/or no CDC activity. In certain embodiments, the antibody does not bind to the Fc receptor and/or complement factors. In certain embodiments, the antibody has no effector function.

The present invention further embraces variants and equivalents which are substantially homologous to the chimeric, humanized and/or human antibodies, or antibody fragments thereof, set forth herein. These can contain, for example, conservative substitution mutations, i.e. the substitution of one or more amino acids by similar amino acids.

Thus, the present invention provides methods for generating an antibody that binds Notch1. In some embodiments, the method for generating an antibody that binds Notch1 comprises using hybridoma techniques. In some embodiments, the method comprises using an extracellular domain of human or mouse Notch1 as an immunizing antigen. In some embodiments, the method of generating an antibody that binds Notch1 comprises screening a human phage library. The present invention further provides methods of identifying an antibody that binds Notch1. In some embodiments, the antibody is identified by screening for binding to Notch1 with flow cytometry (FACS). In some embodiments, the antibody is identified by screening for inhibition or blocking of Notch1 activation. In some embodiments, the antibody is identified by screening for inhibition or blocking of Notch1 signaling.

In certain embodiments, the antibodies as described herein are isolated. In certain embodiments, the antibodies as described herein are substantially pure.

In some embodiments of the present invention, the Notch1 binding agents are polypeptides. The polypeptides can be recombinant polypeptides, natural polypeptides, or synthetic polypeptides that bind a non-ligand binding membrane proximal region of the extracellular domain of human Notch1. In some embodiments, the polypeptides comprise an antibody or fragment thereof that binds a non-ligand binding membrane proximal region of the extracellular domain of human Notch1. It will be recognized by those of skill in the art that some amino acid sequences of a polypeptide can be varied without significant effect of the structure or function of the protein. Thus, the Notch1 binding polypeptides further include variations of the polypeptides which show substantial binding activity to a membrane proximal region of the extracellular domain of human Notch1. In some embodiments, amino acid sequence variations of Notch1 binding polypeptides include deletions, insertions, inversions, repeats, and/or type substitutions.

The polypeptides and variants thereof, can be further modified to contain additional chemical moieties not not many part of the polypeptide. The derivatized moieties can improve the solubility, the biological half life and/or absorption of the polypeptide. The moieties can also reduce or eliminate any undesirable side effects of the polypeptides and variants. An overview for chemical moieties can be found in *Remington: The Science and Practice of Pharmacy*, $21^{st}$ Edition, University of the Sciences Philadelphia 2005.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. (See, e.g., Zoeller et al., 1984, *PNAS*, 81:5662-5066 and U.S. Pat. No. 4,588,585.)

In some embodiments, a DNA sequence encoding polypeptide of interest may be constructed by chemical synthesis using an oligonucleotide synthesizer. Oligonucleotides can be designed based on the amino acid sequence of the desired polypeptide and by selecting those codons that are favored in the host cell in which the recombinant polypeptide of interest will be produced. Standard methods can be applied to synthesize a polynucleotide sequence encoding a polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, recombinant DNA techniques, site-directed mutagenesis or another method), the polynucleotide sequences encoding a particular polypeptide of interest can be inserted into an expression vector and operatively linked to an expression control sequence appropriate for expression of the polypeptide in a desired host.

Proper assembly can be confirmed by nucleotide sequencing, restriction mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding Notch1 binding agents such as polypeptides or antibodies or fragments thereof. For example, recombinant expression vectors can be replicable DNA constructs which have synthetic or cDNA-derived DNA fragments encoding a polypeptide chain of a Notch1 binding agent or antibody or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of expression control sequence and expression vector depends upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a Notch1 binding agent or antibody (or a Notch1 polypeptide to use as an antigen) include prokaryotes, yeast, insect or higher eukaryotic cells under the control of appropriate promoters. Prokaryotes include gram-negative or gram-positive organisms, for example, *E. coli* or *Bacillus*. Higher eukaryotic cells include established cell lines of mammalian origin as described below. Cell-free translation systems could also be employed.

Various mammalian or insect cell culture systems are used to express recombinant polypeptides. Expression of recombinant proteins in mammalian cells can be preferred because such proteins are generally correctly folded, appropriately modified and completely functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived) and BHK (hamster kidney fibroblast-derived) cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are well-known to those of skill in the art (see, e.g., Luckow and Summers, 1988, *Bio/Technology*, 6:47).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, high performance liquid chromatography (HPLC), nuclear magnetic resonance and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In other embodiments, an anion exchange resin can be employed, for example, a matrix or substrate having pendant diethylaminoethyl (DEAE) groups. The matrices can be acrylamide, agarose, dextran, cellulose or other types commonly employed in protein purification. In some embodiments, a cation exchange step can be employed. Suitable cation exchangers include various insoluble matrices comprising sulfopropyl or carboxymethyl groups. In some embodiments, a hydroxyapatite (CHT) media can be employed, including but not limited to, ceramic hydroxyapatite. In some embodiments, one or more reversed-phase HPLC steps employing hydrophobic RP-HPLC media, e.g., silica gel having pendant methyl or other aliphatic groups, can be employed to further purify a recombinant protein. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Pub. Nos. 2008/0312425; 2008/0177048; and 2009/0187005.

In certain embodiments, the Notch1 binding agent is a polypeptide that is not an antibody. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-658; Nygren, 2008, *FEBS J.*, 275:2668-76; and Skerra, 2008, *FEBS J.*, 275:2677-83. In certain embodiments, phage display technology may be used to produce and/or identify a Notch1 binding polypeptide. In certain embodiments, the Notch1 binding polypeptide comprises a protein scaffold of a type selected from the group consisting of protein A, protein G, a lipocalin, a fibronectin domain, an ankyrin consensus repeat domain, and thioredoxin.

In certain embodiments, the Notch1 binding agents or antibodies can be used in any one of a number of conjugated (i.e. an immunoconjugate or radioconjugate) or non-conjugated fauns. In certain embodiments, the antibodies can be used in a non-conjugated form to harness the subject's natural defense mechanisms including complement-dependent cytotoxicity and antibody dependent cellular toxicity to eliminate the malignant or cancer cells.

In some embodiments, the Notch1 binding agent (e.g., an antibody or polypeptide) is conjugated to a cytotoxic agent. In some embodiments, the cytotoxic agent is a chemotherapeutic agent including, but not limited to, methotrexate, adriamycin, doxorubicin, melphalan, mitomycin C, chlorambucil, daunorubicin or other intercalating agents. In some embodiments, the cytotoxic agent is an enzymatically active toxin of bacterial, fungal, plant or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re and $^{212}$Bi. Conjugates of an antibody and one or more small molecule toxins, such as a calicheamicin, maytansinoids, a trichothene, and CC1065, and the derivatives of these toxins that have toxin activity, can also be used. Conjugates of an antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents.

In certain embodiments, the invention encompasses polynucleotides comprising polynucleotides that encode a polypeptide that specifically binds Notch1 or a fragment of such a polypeptide. The term "polynucleotides that encode a polypeptide" encompasses a polynucleotide which includes only coding sequences for the polypeptide as well as a polynucleotide which includes additional coding and/or non-coding sequences. For example, the invention provides a polynucleotide comprising a nucleic acid sequence that encodes an antibody to a human Notch1 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, a polynucleotide comprising a polynucleotide encoding a polypeptide comprising a sequence selected from the group consisting of SEQ ID NO:8, SEQ ID NO:14, SEQ ID NO:24, SEQ ID NO:28, and SEQ ID NO:32 is provided. In some embodiments, a polynucleotide sequence encoding a polypeptide (with or without the signal sequence) comprising a sequence selected from the group consisting of SEQ ID NO:4, SEQ ID NO:10, SEQ ID NO:22, SEQ ID NO:26, and SEQ ID NO:30 is provided.

In some embodiments, a polynucleotide comprising a nucleotide sequence (with or without the signal sequence) selected from the group consisting of SEQ ID NO:3, SEQ ID NO:5, SEQ ID NO:7, SEQ ID NO:9, SEQ ID NO:11, SEQ ID NO:13, SEQ ID NO:21, SEQ ID NO:25, and SEQ ID NO:29 is provided.

In certain embodiments, a polynucleotide comprising a polynucleotide (with or without the signal sequence) having a nucleotide sequence at least 80% identical, at least 85% identical, at least 90% identical, at least 95% identical, and in some embodiments, at least 96%, 97%, 98% or 99% identical to a polynucleotide comprising a sequence selected from the group consisting of SEQ ID NO:7, SEQ ID NO:13, SEQ ID NO:21, SEQ ID NO:25, and SEQ ID NO:29 is provided. In some embodiments, the polynucleotides have a nucleotide sequence at least 90% identical to SEQ ID NO:7 or SEQ ID NO:13.

Also provided is a polynucleotide that comprises a polynucleotide that hybridizes to SEQ ID NO:3, SEQ ID NO:5, SEQ ID NO:7, SEQ ID NO:9, SEQ ID NO:11, SEQ ID NO:13, SEQ ID NO:21, SEQ ID NO:25, or SEQ ID NO:29, and/or to a polynucleotide encoding a polypeptide having the sequence of SEQ ID NO:4, SEQ ID NO:6, SEQ ID NO:8, SEQ ID NO:10, SEQ ID NO:12, SEQ ID NO:14, SEQ ID NO:22, SEQ ID NO:23, SEQ ID NO:24, SEQ ID NO:26, SEQ ID NO:27, SEQ ID NO:28, SEQ ID NO:30, SEQ ID NO:31, or SEQ ID NO:32. In certain embodiments, the hybridization is under conditions of high stringency.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to produce the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows, for example, for purification and/or identification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDK (SEQ ID NO:33) which can be used in conjunction with other affinity tags.

The present invention further relates to variants of the hereinabove described polynucleotides encoding, for example, fragments, analogs, and/or derivatives.

In certain embodiments, the present invention provides polynucleotides comprising polynucleotides having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, to human Notch1 described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, polynucleotide variants contain "silent" substitutions due to the degeneracy of the genetic code. Polynucleotide variants can be produced for a variety of reasons, for example, to optimize codon expression for a particular host (e.g., change codons in the human mRNA to those preferred by a bacterial host such as *E. coli*).

In some embodiments, polynucleotides may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps"; substitution of one or more of the naturally occurring nucleotides with an analog; internucleotide modifications such as uncharged linkages (e.g., methyl phosphonates, phosphotriesters, phosphoamidates, and carbamates) and charged linkages (e.g., phosphorothioates and phosphorodithioates); pendant moieties, such as proteins (e.g., nucleases, toxins, antibodies, signal peptides, and poly-L-lysine); intercalators (e.g., acridine and psoralen); chelators (e.g., metals, radioactive metals, boron, and oxidative metals); alkylators; modified linkages (e.g., alpha anomeric nucleic acids); as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, heptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR, ("amidate"), P(O)R, P(O)OR', CO or $CH_2$ ("formacetal"), in which each R or R' is independently H or a substituted or unsubstituted alkyl (1-20 C) optionally containing an ether (—O—) linkage, aryl, alkenyl, cycloalkyl, cycloalkenyl or araldyl. Not all linkages in a polynucleotide need be identical.

In certain embodiments, the polynucleotides as described herein are isolated. In certain embodiments, the polynucleotides as described herein are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

III. Methods of Use and Pharmaceutical Compositions

The Notch1 binding agents (e.g., polypeptides and/or antibodies) of the invention are useful in a variety of applications including, but not limited to, therapeutic treatment methods, such as the treatment of a hematologic cancer. In certain embodiments, the agents are useful for modulating Notch1 activity, inhibiting Notch1 activity, inhibiting or blocking Notch1/Notch ligand interactions, inhibiting Notch1 signaling, and/or inhibiting Notch1 activation. In some embodiments, the Notch1 binding agents are useful for blocking cleavage of Notch1, for inhibiting cleavage with the membrane proximal region, for inhibiting cleavage at the S2 site within the membrane proximal region, for inhibiting release of the intracellular domain of Notch1. In some embodiments, the Notch1 binding agents are useful in inhibiting cancer cell growth, reducing cancer cell volume, reducing the cancer cell population, reducing the tumorigenicity of a hematologic cancer, reducing the frequency of cancer stem cells in a hematologic cancer, reducing the frequency of leukemia initiating cells in a hematologic cancer, inducing death of cancer cells, and/or inducing differentiation. The methods of use may be in vitro, ex vivo, or in vivo methods. In certain embodiments, the Notch1 binding agent (e.g., polypeptide and/or antibody) is an antagonist of Notch1. In certain embodiments, the Notch1 binding agent is an antagonist of a Notch signaling pathway. In some embodiments, the Notch1 binding agent is an antagonist of Notch1 activation.

In certain embodiments, the Notch1 binding agents as described herein are used in the treatment of a disease associated with Notch signaling and activation. In particular embodiments, the disease is a disease associated with a Notch signaling pathway. In particular embodiments, the disease is a disease associated with a constitutively activated Notch1. In some embodiments, cancer cell growth is associated with a Notch signaling pathway. In some embodiments, cancer cell growth is associated with Notch1 activation. In some embodiments, the disease is a hematologic cancer. In certain embodiments, the hematologic cancer is acute myelogenous leukemia, Hodgkin lymphoma, multiple myeloma or T-cell acute lymphoblastic leukemia. In some embodiments, the disease is T-cell acute lymphoblastic leukemia.

The present invention further provides methods for inhibiting growth of a hematologic cancer using the Notch1 binding agents described herein. In certain embodiments, the method of inhibiting growth of a hematologic cancer comprises contacting tumor cells with a Notch1 binding agent (e.g., an antibody) in vitro. For example, an immortalized cell line or a cancer cell line that expresses Notch1 on the cell surface is cultured in medium to which is added the antibody or other agent to inhibit cancer cell growth. In some embodiments, cancer cells are isolated from a patient sample such as, for example, a tissue biopsy, pleural effusion, or blood sample and cultured in medium to which is added a Notch1 binding agent to inhibit cancer cell growth.

In some embodiments, the method of inhibiting growth of a hematologic cancer comprises contacting the cancer cells with a Notch1 binding agent (e.g., an antibody) in vivo. In certain embodiments, contacting cancer cells with a Notch1 binding agent is undertaken in an animal model. For example, in one animal model for leukemia, immunocompromised mice (e.g., NOD/SCID mice) are sub-lethally irradiated and then within 24 hours are injected intravenously with primary human leukemia cells. It has been shown that human leukemia cells can engraft in the hematopoietic tissues of the mice. In an alternative model, immunocompromised mice (e.g., NOD/SCID mice) are injected intravenously with primary human leukemia cells without prior irradiation. In a different animal model for leukemia, immunocompromised mice (e.g., NOD/SCID mice) are sub-lethally irradiated and then "preconditioned" with human cord blood or bone marrow mononuclear cells. After a period of time (e.g., 5-7 days), these mice are injected with cells from a patient suffering from a hematologic cancer such as T-cell acute lymphoblastic leukemia. The leukemia cells have been shown to engraft in these pre-conditioned mice. (See, e.g., Dialynas et al., 2001, *Stem Cells* 19:443-452, Dialynas et al., 2001, *Blood* 97:3218-3225 and U.S. Pat. Nos. 6,930,222 and 7,186,880).

In some embodiments, Notch1 binding agents (e.g., antibodies) are administered soon after the injection of the hematologic cancer cells to study the effect of the Notch1 binding agents upon engraftment of the cancer cells. In some embodiments, Notch1 binding agents are administered prior to the injection of the hematologic cancer cells (e.g., leukemia cells). In some embodiments, Notch1 binding agents are administered after the hematologic cancer cells have engrafted into the mice to study the effect of the Notch1 binding agents upon an established hematologic cancer. In some embodiments, Notch1 binding agents are administered after the hematologic cancer cells have engrafted into preconditioned mice to study the effect of the Notch1 binding agents upon an established hematologic cancer. In some embodiments, the Notch1 binding agents are administered to the mice 1 day, 2 days, 3 days, 4 days, 5 days, etc. before the hematologic cancer cells (e.g., leukemia cells) are injected into the mice. In some embodiments, the Notch1 binding agents are administered to the mice 1 week, 2 weeks, 3 weeks, 4 weeks, 5 weeks, 6 weeks, etc. after engraftment of the hematologic cancer cells. After administration of Notch1 binding agents, the mice are observed for inhibition of cancer cell engraftment and/or inhibition of cancer cell growth. In some embodiments, cancer stem cells are isolated from a patient sample such as, for example, a tissue biopsy, pleural effusion, or blood sample and injected into immunocompromised mice that are then administered a Notch1 binding agent to inhibit cancer cell growth. In some embodiments, cancer stem cells are isolated from a patient sample such as, for example, a tissue biopsy, pleural effusion, or blood sample and injected into irradiated, preconditioned immunocompromised mice that are then administered a Notch1 binding agent to inhibit cancer cell growth. In some embodiments, the Notch1 binding agent is administered at the same time or shortly after introduction of cancer cells into the animal to prevent cancer cell growth. In some embodiments, the Notch1 binding agent is administered as a therapeutic after the cancer cells have engrafted and established a hematologic cancer. In some embodiments, the hematologic cancer cells comprise cancer stem cells. In some embodiments, the hematologic cancer cells comprise leukemia initiating cells.

The invention provides methods of inhibiting the growth of a hematologic cancer in a subject, the method comprising administering to the subject a therapeutically effective amount of an antibody that specifically binds a non-ligand binding membrane proximal region of the extracellular domain of human Notch1. In some embodiments, the hematologic cancer comprises cancer stem cells. In some embodiments, the hematologic cancer comprises leukemia initiating cells. In some embodiments, the method comprises targeting the cancer stem cells or leukemia initiating cells with the Notch1 antibodies described herein. In certain embodiments, the method of inhibiting growth of a hematologic cancer comprises administering a therapeutically effective amount of the Notch1 antibodies described herein.

In certain embodiments, the method of inhibiting growth of a hematologic cancer comprises reducing the frequency of cancer stem cells in the cancer, reducing the number of cancer stem cells in the cancer, reducing the tumorigenicity of the cancer, and/or reducing the tumorigenicity of the cancer by reducing the number or frequency of cancer stem cells in the cancer. In some embodiments, the method of inhibiting growth of a hematologic cancer comprises inhibiting the activity of a Notch1 receptor. In certain embodiments, the hematologic cancer includes, but is not limited to, acute myelogenous leukemia, Hodgkin lymphoma, multiple myeloma or T-cell acute lymphoblastic leukemia. In some embodiments, the hematologic cancer is T-cell acute lymphoblastic leukemia.

In certain embodiments, the method of treating a hematologic cancer comprises administering a therapeutically effective amount of an antibody conjugated to a cytotoxic moiety that specifically binds a non-ligand binding membrane proximal region of the extracellular domain of a human Notch1 receptor and inhibits cancer growth. In certain embodiments, the method of treating a hematologic cancer comprises administering a therapeutically effective amount of an antibody of any of the aspects and/or embodiments, as well as other aspects and/or embodiments described herein, in combination with radiation therapy. In certain embodiments, the method of treating a hematologic cancer comprises administering a therapeutically effective amount of an antibody of any of the aspects and/or embodiments, as well as other aspects and/or embodiments described herein, in combination with chemotherapy. In certain embodiments, the method of treating a hematologic cancer comprises administering a therapeutically effective amount of an antibody that specifically binds a non-ligand binding membrane proximal region of the extracellular domain of a human Notch1 receptor and inhibits cancer growth wherein the hematologic cancer includes, but is not limited to, acute myelogenous leukemia, Hodgkin lymphoma, multiple myeloma or T-cell acute lymphoblastic leukemia.

In another aspect, the present invention provides a method of treating a hematologic cancer in a subject in need thereof comprising administering to a subject a therapeutically effective amount of an antibody that specifically binds a non-ligand binding membrane proximal region of the extracellular domain of a human Notch1 receptor protein and inhibits cancer growth in the subject. In certain embodiments, the method of treating a hematologic cancer comprises administering a therapeutically effective amount of a monoclonal antibody. In certain embodiments, the method of treating a hematologic cancer comprises administering a therapeutically effective amount of a chimeric antibody. In certain embodiments, the method of treating a hematologic cancer comprises administering a therapeutically effective amount of a humanized antibody. In certain embodiments, the method of treating a hematologic cancer comprises administering a therapeutically effective amount of a human antibody.

In certain embodiments, the method of inhibiting growth of a hematologic cancer comprises administering to a subject a therapeutically effective amount of a Notch1 binding agent. In certain embodiments, the subject is a human. In certain embodiments, the subject has a hematologic cancer. In certain embodiments, the subject has had cancer cells removed. In some embodiments, the Notch1 binding agent is an antibody. In some embodiments, the Notch1 binding agent is antibody 52M51. In some embodiments, the Notch1 binding agent is a humanized version of 52M51.

In certain embodiments, the hematologic cancer cell expresses Notch1 to which the Notch1 binding agent or antibody binds. In certain embodiments, the tumor over-expresses a human Notch1. In some embodiments, the Notch1 binding agent binds Notch1 and inhibits or reduces growth of the hematologic cancer. In some embodiments, the Notch1 binding agent binds Notch1, interferes with Notch1/Notch ligand interactions and inhibits or reduces growth of the hematologic cancer. In some embodiments, the Notch1 binding agent binds Notch1, inhibits Notch activation and inhibits or reduces growth of the hematologic cancer. In some embodiments, the Notch1 binding agent binds Notch1, and reduces the frequency of cancer stem cells in the hematologic cancer. In some embodiments, the Notch1 binding agent binds a constitutively activated Notch1 and inhibits Notch1 activity.

In certain embodiments, the hematologic cancer is acute myelogenous leukemia, Hodgkin lymphoma, multiple myeloma or T-cell acute lymphoblastic leukemia. In certain embodiments, the hematologic cancer is acute myelogenous leukemia. In certain embodiments, the hematologic cancer is Hodgkin lymphoma. In certain embodiments, the hematologic cancer is multiple myeloma. In certain embodiments, the hematologic cancer is T-cell acute lymphoblastic leukemia. In certain embodiments, the subject is a human.

The present invention further provides methods for treating a hematologic cancer using the Notch1 binding agents described herein. In certain embodiments, the hematologic cancer is characterized by cells expressing Notch1 to which the Notch1 binding agent (e.g., antibody) binds. In certain embodiments, the hematologic cancer over-expresses human Notch1. In certain embodiments, the hematologic cancer is characterized by cells expressing Notch1, wherein the Notch1 agent (e.g., an antibody) interferes with Notch ligand-induced Notch signaling and/or activation. In some embodiments, the Notch1 binding agent binds Notch1 and inhibits or reduces growth of the hematologic cancer. In some embodiments, the Notch1 binding agent binds Notch1, interferes with Notch1/Notch ligand interactions and inhibits or reduces growth of the hematologic cancer. In some embodiments, the Notch1 binding agent binds Notch1, inhibits Notch1 activation and inhibits or reduces growth of the hematologic cancer. In some embodiments, the Notch binding agent binds Notch, and reduces the frequency of cancer stem cells in the hematologic cancer.

The present invention provides for methods of treating a hematologic cancer comprising administering a therapeutically effective amount of a Notch1 binding agent to a subject (e.g., a subject in need of treatment). In certain embodiments, the subject is a human. In certain embodiments, the subject has a hematologic cancer. In certain embodiments, the subject has had cancer cells removed. In some embodiments, the Notch1 binding agent is an antibody. In some embodiments, the Notch1 binding agent is antibody 52M51. In some embodiments, the Notch1 binding agent is a humanized version of 52M51.

In certain embodiments, the hematologic cancer is a cancer selected from the group consisting of acute myelogenous leukemia, Hodgkin lymphoma, multiple myeloma and T-cell acute lymphoblastic leukemia. In certain embodiments, the hematologic cancer is acute myelogenous leukemia. In certain embodiments, the hematologic cancer is Hodgkin lymphoma. In certain embodiments, the hematologic cancer is multiple myeloma. In certain embodiments, the hematologic cancer is T-cell acute lymphoblastic leukemia. In certain embodiments, the subject is a human.

The invention also provides a method of inhibiting Notch signaling or Notch activation in a cell comprising contacting the cell with an effective amount of a Notch1 binding agent. In certain embodiments, the cell is a hematologic cancer cell. In certain embodiments, the method is an in vivo method wherein the step of contacting the cancer cell with the Notch1 binding agent comprises administering a therapeutically effective amount of the Notch1 binding agent to the subject. In some embodiments, the method is an in vitro or ex vivo method. In certain embodiments, the Notch1 binding agent inhibits Notch signaling. In some embodiments, the Notch1 binding agent inhibits Notch activation. In certain embodiments, the Notch1 binding agent interferes with a Notch1/Notch ligand interaction. In certain embodiments, the Notch1 binding agent inhibits Notch activation of at least one additional Notch receptor selected from the group consisting of Notch2, Notch3, and Notch4. In some embodiments, the Notch1 binding agent is an antibody. In some embodiments, the Notch1 binding agent is antibody 52M51. In some embodiments, the Notch1 binding agent is a humanized version of 52M51.

In addition, the invention provides a method of reducing the tumorigenicity of a hematologic cancer in a subject, comprising administering a therapeutically effective amount of a Notch1 binding agent to the subject. In certain embodiments, the hematologic cancer comprises cancer stem cells. In certain embodiments, the hematologic cancer comprises leukemia initiating cells. In certain embodiments, the frequency of cancer stem cells in the hematologic cancer is reduced by administration of the Notch1 binding agent. The invention also provides a method of reducing the frequency of cancer stem cells in a hematologic cancer, comprising contacting the cancer cells with an effective amount of a Notch1 binding agent. In some embodiments, the Notch1 binding agent is antibody 52M51. In some embodiments, the Notch1 binding agent is a humanized version of 52M51.

The invention also provides a method of treating a disease or disorder in a subject, wherein the disease or disorder is characterized by an increased level of cancer stem cells, leukemia initiating cells and/or progenitor cells. In some embodiments, the treatment methods comprise administering a therapeutically effective amount of the Notch1 binding agent, polypeptide, or antibody to the subject.

The present invention further provides pharmaceutical compositions comprising Notch1 binding agents, antibodies, or polypeptides as described herein. These pharmaceutical compositions find use in inhibiting growth of cancer cells, inhibiting growth of a hematologic cancer, and treating a hematologic cancer in human patients.

Formulations are prepared for storage and use by combining a purified antagonist (e.g., antibody) of the present invention with a pharmaceutically acceptable vehicle (e.g., carrier, excipient, etc.) (*Remington: The Science and Practice of Pharmacy*, 21$^{st}$ Edition, University of the Sciences Philadelphia 2005). Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol; low molecular weight polypeptides (less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counterions such as sodium; metal complexes such as Zn-protein complexes; and/or non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary such as by inhalation or insufflation of powders or aerosols (including by nebulizer), intratracheal, intranasal, epidermal and transdermal; oral; parenteral including intravenous, intraarterial, intratumoral, subcutaneous, intraperitoneal or intramuscular injection or infusion; or intracranial such as intrathecal or intraventricular.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g., water) to form a solid preformulation composition containing a homogeneous mixture of a compound of the present invention, or a non-toxic pharmaceutically acceptable salt thereof. The solid preformulation composition is then subdivided into unit dosage forms of the type described herein. The tablets, pills, etc of the novel composition can be coated or otherwise compounded to provide a dosage fat in affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, *PNAS*, 82:3688; Hwang, et al., 1980, *PNAS*, 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, macroemulsions, nano-particles and nanocapsules) or in macroemulsions as described in *Remington: The Science and Practice of Pharmacy*, 21$^{st}$ Edition, University of the Sciences Philadelphia 2005.

In addition sustained-release preparations can be prepared. Suitable examples of sustained-release preparations include semi-permeable matrices of solid hydrophobic polymers containing the antibody, which matrices are in the Ruin of shaped articles (e.g. films, or microcapsules). Examples of sustained-release matrices include polyesters, hydrogels such as poly (2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D(−)-3-hydroxybutyric acid. In some embodiments the antibodies can be used to treat various conditions characterized by expression and/or increased responsiveness of cells to a cancer stem cell marker. Particularly it is envisioned that the antibodies against a cancer stem cell marker, for example Notch1, will be used to treat proliferative disorders including, but not limited to, benign and malignant tumors of the kidney, liver, bladder, breast, stomach, ovary, colon, rectum, prostate, lung, vulva, thyroid, head and neck, brain (e.g., glioblastoma, astrocytoma, medulloblastoma), and hematologic cancers such as leukemias and lymphomas.

In certain embodiments, in addition to administering a Notch1 binding agent, the method or treatment further comprises administering at least one additional therapeutic agent. An additional therapeutic agent can be administered prior to, concurrently with, and/or subsequently to, administration of the Notch1 binding agent. Pharmaceutical compositions comprising the Notch1 binding agent and the additional therapeutic agent(s) are also provided. In some embodiments, the at least one additional therapeutic agent comprises 1, 2, 3, or more additional therapeutic agents.

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects. Combination therapy may decrease the likelihood that resistant cancer cells will develop. Combination therapy may allow for one agent to be targeted to tumorigenic cancer stem cells and a second agent to be targeted to nontumorigenic cancer cells.

It will be appreciated that the combination of a Notch1 binding agent and an additional therapeutic agent may be administered in any order or concurrently. In some embodiments, the Notch1 binding agent will be administered to patients that have previously undergone treatment with a second therapeutic agent. In certain other embodiments, the Notch1 binding agent and a second therapeutic agent will be administered substantially simultaneously or concurrently. For example, a subject may be given the Notch1 binding agent (e.g., an antibody) while undergoing a course of treatment with a second therapeutic agent (e.g., chemotherapy). In certain embodiments, the Notch1 binding agent will be administered within 1 year of the treatment with a second therapeutic agent. In certain alternative embodiments, the Notch1 binding agent will be administered within 10, 8, 6, 4, or 2 months of any treatment with a second therapeutic agent. In certain other embodiments, the Notch1 binding agent will be administered within 4, 3, 2, or 1 weeks of any treatment with a second therapeutic agent. In some embodiments, the Notch1 binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

Therapeutic agents used for the treatment of hematologic cancers include, but are not limited to, antibiotics such as daunorubicin, doxorubicin, mitoxantrone and idarubicin; topoisomerase inhibitors such as etoposide, teniposide, and topotecan; DNA synthesis inhibitors such as carboplatin; DNA-damaging agents such as cyclophosphamide and ifosfamide; cytotoxic enzymes such as asparaginase and pegasparagase; tyrosine kinases inhibitors such as imatinib mesylate, dasatinib and nilotinib; antimetabolites such as azacitidine, clofarabine, cytarabine, cladribine, fludarabine, hydroxyurea, mercaptopurine, methotrexate, thioguanine and nelarabine; synthetic hormones such as prednisone, prednisolone and dexamethasone, antimitotic agents such as vincristine and proteasome inhibitors such as bortezomib.

Therapeutic agents that may be administered in combination with the Notch1 binding agents include the above name therapeutic agents as well as other chemotherapeutic agents. Thus, in some embodiments, the method or treatment involves the combined administration of a Notch1 binding agent or antibody and a chemotherapeutic agent or cocktail of multiple different chemotherapeutic agents. Treatment with a Notch1 binding agent or antibody can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Chemotherapeutic agents useful in the instant invention include, but are not limited to, alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel and docetaxel; chlorambucil; gemcitabine; 6-thioguanine; mercaptopurine; platinum analogs such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a vinca alkaloid, such as vincristine, binblastine, vinorelbine, or vindesine, or pharmaceutically acceptable salts, acids, or derivatives thereof.

In some embodiments, the treatment involves a Notch1 binding agent (e.g., an antibody) as described herein in combination with chemotherapeutic agent selected from the group consisting of prednisone, vincristine, daunorubicin, L-asparaginase, methotrexate and cyclophosphamide. In some embodiments, the additional therapeutic agent is imatinib, nelarabine or dastinib. In some embodiments, the additional therapeutic agent is idarubicin, cytosine arabinoside, mitoxantrone or gemtuzumab ozogamicin.

In certain embodiments, the treatment involves the combined administration of a Notch1 binding agent (e.g., an antibody) of the present invention and radiation therapy. Treatment with the Notch1 binding agent can occur prior to, concurrently with, or subsequent to administration of radiation therapy. Dosing schedules for such radiation therapy can be determined by the skilled medical practitioner. In some embodiments, the binding agent or antibody is administered after radiation treatment. In some embodiments, the binding agent or antibody is administered with radiation therapy.

In some embodiments, a second therapeutic agent comprises an antibody. Thus, treatment can involve the combined administration of a Notch1 binding agent (e.g. an antibody) of the present invention with other antibodies against additional tumor-associated antigens including, but not limited to, antibodies that bind to EGFR, ErbB2, DLL4, Notch, or NF-κB. Exemplary, anti-DLL4 antibodies, are described, for example, in U.S. Pat. No. 7,750,124. Additional anti-DLL4 antibodies are described in, e.g., International Patent Pub. Nos. WO 2008/091222 and WO 2008/0793326, and U.S. Patent Application Pub. Nos. 2008/0014196; 2008/0175847; 2008/0181899; and 2008/0107648. Exemplary anti-Notch antibodies, are described, for example, in U.S. Patent Application Pub. No. 2008/0131434. Combined administration can include co-administration, either in a single pharmaceutical formulation or using separate formulations, or consecutive administration in either order but generally within a time period such that all active agents can exert their biological activities simultaneously.

Furthermore, treatment with the Notch1 binding agents described herein can include combination treatment with one or more cytokines (e.g., lymphokines, interleukins, tumor necrosis factors, and/or growth factors) or can be accompanied by surgical removal of tumors, cancer cells or any other therapy deemed necessary by a treating physician. For the treatment of the disease, the appropriate dosage of an antibody or other agent of the present invention depends on the type of disease to be treated, the severity and course of the disease, the responsiveness of the disease, whether the antibody is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antagonist. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the antibody or agent in bodily fluids or tissues.

The present invention provides kits comprising the antibodies described herein and that can be used to perform the methods described herein. In some embodiments, a kit comprises at least one purified antibody against human Notch1, in one or more containers. In some embodiments, a kit comprises at least one purified antibody against a non-ligand binding membrane proximal region of the extracellular domain of human Notch1, in one or more containers. In some embodiments, a kit comprises the antibody 52M51 or a humanized variant of 52M51.

EXAMPLES

Example 1

Antibodies were generated against a non-ligand binding region of Notch1, specifically the non-ligand binding membrane proximal region of the extracellular domain. In certain embodiments, recombinant polypeptide fragments of the human Notch1 extracellular domain were generated as antigens for antibody production. Standard recombinant DNA technology was used to isolate polynucleotides encoding the membrane proximal region of the extracellular domain of human Notch1 amino acids 1427-1732 (SEQ ID NO:1). These polynucleotides were separately ligated in-frame N-terminal to a human Fc and histidine-tag and cloned into a transfer plasmid vector for baculovirus-mediated expression in insect cells. Standard transfection, infection, and cell culture protocols were used to produce recombinant insect cells expressing the corresponding Notch1 polypeptide corresponding to a membrane proximal region comprising amino acids 1427-1732 (SEQ ID NO:2) (O'Reilly et al., 1994, Baculovirus Expression Vectors: A Laboratory Manual, Oxford: Oxford University Press).

Notch1 membrane proximal region (Notch1 amino acids 1472-1732) polypeptide was purified from insect cell lysates using protein A and $Ni^{++}$-chelate affinity chromatography as known to one skilled in the art. Purified Notch1 membrane proximal region polypeptide was dialyzed against PBS (pH=7), concentrated to approximately 1 mg/ml, and sterile filtered in preparation for immunization.

Mice (n=3) were immunized with purified Notch1 antigen protein (Antibody Solutions; Mountain View, Calif.) using standard techniques. Blood from individual mice was screened approximately 70 days after initial immunization for antigen recognition using ELISA and FACS analysis (as described herein). The two animals with the highest antibody titers were selected for final antigen boost after which spleen cells were isolated for hybridoma production. Hybridoma cells were plated at 1 cell per well in 96 well plates, and the supernatant from each well screened by ELISA and FACS analysis against Notch1 membrane proximal region polypeptide. Several hybridomas with high antibody titer were selected and scaled up in static flask culture. Antibodies were purified from the hybridoma supernatant using protein A or protein G agarose chromatography. Purified monoclonal antibodies were tested again by FACS as described herein. Several antibodies that recognized the membrane proximal region of the extracellular domain of human Notch1 were isolated. A hybridoma cell line expressing antibody 52M51 was deposited with ATCC under the conditions of the Budapest Treaty on Aug. 7, 2008 and assigned ATTC Patent Deposit Designation PTA-9405. The nucleotide and predicted protein sequences of both the heavy chain (SEQ ID NO:9 and 10) and light chain (SEQ ID NO:3 and 4) of antibody 52M51 were determined.

Human Antibodies

In alternative embodiments, human antibodies that specifically recognize the non-ligand binding membrane proximal region of the extracellular domain of a Notch1 receptor are isolated using phage display technology. In certain embodiments, a synthetic antibody library containing human antibody variable domains is screened for specific and high affinity recognition of a Notch receptor antigen described herein. In certain embodiments, a human Fab phage display library is screened using a series of recombinant proteins comprising the non-ligand binding membrane proximal region of the extracellular domain of a Notch 1 receptor. Briefly, $2 \times 10^{13}$ Fab displaying phage particles are incubated with recombinant protein (passively immobilized) in round one, the non-specific phage are washed off, and then specific phage are eluted with either low pH (cells) or DTT (recombinant protein). The eluted output is used to infect TG1 F+ bacteria, rescued with helper phage, and then Fab display induced with IPTG (0.25 mM). This process is repeated for two additional rounds and then round three is screened in ELISA against passively immobilized antigen (5 m/ml).

CDR cassettes in the library are specifically exchanged via unique flanking restriction sites for antibody optimization. Optimized human variable regions are then cloned into an Ig expression vector containing human IgG1 heavy-chain and kappa light-chain for expression of human antibodies in CHO cells.

Epitope Mapping

To identify antibodies that recognize specific a non-ligand binding membrane proximal region of the Notch1 receptor extracellular domains, epitope mapping is performed. In certain embodiments, mammalian expression plasmid vectors comprising a CMV promoter upstream of polynucleotides that encode fragments of the extracellular Notch1 domain as Fc fusion proteins are generated using standard recombinant DNA technology. In certain embodiments, epitope mapping of the 52M series of non-ligand binding region antibodies is done using a series of fusion proteins and deletions of the membrane proximal region of the extracellular domain of a human Notch1 from about amino acid 1427 to about amino acid 1732. These recombinant fusion proteins are expressed in transiently transfected HEK 293 cells from which conditioned medium is collected twenty-four to forty-eight hours post-transfection for ELISA.

In certain embodiments, the Notch1 fusion protein fragments are separated on SDS-PAGE gels and probed with both anti-Fc antibodies to detect the presence of all fusion proteins versus anti-Notch1 antibodies to detect the domains recognized by each anti-Notch antibody.

Example 2

Humanized antibodies against a membrane proximal region of the extracellular domain of a human Notch1 were generated. The variable domains of the murine monoclonal antibody 52M51 were isolated and sequenced from the hybridoma line using degenerate PCR essentially as described in Larrick, J. M., et al., 1989, *Biochem. Biophys. Res. Comm.* 160:1250 and Jones, S. T. & Bendig, M. M., 1991, *Bio/Technology* 9:88. Human heavy and light chain variable framework regions likely to be structurally similar to the parental 52M51 antibody amino acid sequences are then considered as reference human framework regions to help guide the design of novel synthetic frameworks. To identify the human framework regions bearing similarity to 52M51 murine frameworks, the predicted protein sequences encoded by the $V_H$ and $V_L$ murine variable domains of 52M51 are compared with human antibody sequences encoded by expressed human cDNA using BLAST searches for human sequence deposited in Genbank. Using this method, expressed human cDNA sequences (e.g., Genbank DA975021, DB242412) and gel inline Vh domains (e.g. IGHV1-24) were selected for further analysis in designing heavy chain frameworks. Similarly, expressed human cDNA sequences (e.g. Genbank CD709370, CD707373) and germline VI (e.g. IGLV7-46, IGLV8-61) were considered in designing light chain frameworks.

The amino acid differences between candidate humanized framework heavy chains and the parent murine monoclonal antibody 52M51 heavy chain variable domain and light chain variable domains were evaluated for likely importance, and a judgment made as to whether each difference in position contributes to proper folding and function of the variable domain. This analysis was guided by examination of solved crystal structures of other antibody fragments (e.g., the structure of Fab 2E8 as described in Trakhanov et al., 1999, *Acta Crystallogr D Biol Crystallogr* 55:122-28, as well as other protein crystal structures (e.g., protein data bank structures 1ADQ and 1GIG)). Structures were modeled using computer software including Jmol, quick PDB, and Pymol. Consideration was given to the potential impact of an amino acid at a given position on the packing of the β-sheet framework, the interaction between the heavy and light chain variable domains, the degree of solvent exposure of the amino acid side chain, and the likelihood that an amino acid would impact the positioning of the CDR loops. From this analysis, nine candidate $V_H$ chains fused in-frame to the human IgG2 constant region and eight candidate V1 chains fused in frame with the human IgLC1 constant region were conceived and chemically synthesized. The candidate heavy chains comprise: i) a synthetic framework designed to resemble natural human frameworks and ii) the parental 52M51 murine antibody CDRs.

The functionality of each candidate variant humanized heavy and light chain was tested by co-transfection into mammalian cells. Each of the nine candidate humanized 52M51 heavy chains described above was co-transfected into HEK 293 cells with the murine 52M51 light chain cDNA, and conditioned media was assayed by ELISA for Notch1 binding activity. The 52M51 heavy chain variant exhibiting the most robust binding was selected. This variant "52M51-H4"

(SEQ ID NO:22) contains, in addition to murine CDRs, variation at 3 framework positions within the Vh framework, Kabat positions 20, 48, and 71 in comparison with an example human framework (e.g. IGHV1-24). The 52M51-H4 humanized heavy chain was then co-transfected into HEK293 cells with each of the eight candidate humanized light chains, and conditioned media was again assayed for antigen binding by ELISA. Two light chain variants "52M51 L3" (SEQ ID NO:26) and "52M51 L4" (SEQ ID NO:30) were found to exhibit better binding than the other candidates and were chosen for further study. Variant 52M51 L3 contains, in addition to murine CDRs, variation at 1 framework position at Kabat position 49 in comparison to an example human framework (e.g., IGLV7-46). Two humanized variant antibodies, 52M51H4L3 and 52M51H4L4, were developed. The polynucleotide encoding 52M51H4L3 was deposited with the ATCC under the conditions of the Budapest Treaty on Oct. 15, 2008, and assigned designation number PTA-9549.

The affinities for human and mouse Notch1 were determined using a Biacore 2000 instrument. Briefly, recombinant human and mouse Notch1 proteins were immobilized on a CM5 chip using standard amine based chemistry (NHS/EDC). Different antibody concentrations were injected over the protein surfaces and kinetic data were collected over time. The data was fit using the simultaneous global fit equation to yield dissociation constants ($K_D$, nM) for each Notch1 (Table 2).

TABLE 2

IgG Dissociation Constants ($K_D$)

| Antibody | Human Notch1 (nM) | Mouse Notch1 (nM) |
|---|---|---|
| 52M51 | 2.86 | NB |
| 52M51H4L3 | 4.33 | NB |
| 52M51H4L4 | 7.35 | NB |

Example 3

Notch Receptor Signaling

The ability of Notch1 antibodies to block ligand-mediated Notch signaling was determined. HeLa cells engineered to over-express Notch1 (Notch1-HeLa) cultured in DMEM supplemented with antibiotics and 10% FCS were co-transfected with 1) pGL4 8×CBF firefly luciferase containing a Notch responsive promoter upstream of a firefly luciferase reporter gene to measure Notch signaling levels in response to DLL4 ligand; and 2) a *Renilla* luciferase reporter (Promega, Madison, Wis.) as an internal control for transfection efficiency. Transfected cells were added to cultures plates coated overnight with 200 ng/well of hDLL4-Fc protein, and antibodies to Notch1 were then added to the cell culture medium. Forty-eight hours following transfection, luciferase levels were measured using a dual luciferase assay kit (Promega, Madison Wis.) with firefly luciferase activity normalized to *Renilla* luciferase activity. The ability of antibodies to inhibit Notch1 pathway activation was thus determined. Antibodies 52M51, 52M63, 52M74, and 52M80, generated against a membrane proximal region of the extracellular domain of human Notch1 (FIG. 1A) significantly reduced luciferase activity indicative of reduced Notch1 signaling as compared to other Notch1 antibodies (FIG. 1B). Further, a humanized variant of antibody 52M51, variant 52M51H4L3 displayed similar potency in reducing luciferase activity (FIG. 1C).

Cleavage of Notch receptors by furin, ADAM, and gamma-secretase results in formation of the Notch intracellular domain (ICD) that then triggers downstream Notch signaling in the nucleus. The ability of Notch1 antibodies to block ligand-mediated receptor activation was determined by Western blot analysis. Notch1-HeLa cells were grown in suspension culture in 293-SMII media (Invitrogen, Carlsbad Calif.). Cultured cells were transferred to 96-well plates in which select wells had been pre-coated with human DLL4-Fc fusion protein (2 µg/ml) in DMEM plus 2% FBS and 1 µM MG132 (Calbiochem, San Diego Calif.). Antibodies generated against a membrane proximal region of the extracellular domain of human Notch1 were added to the cell culture medium, and cells were incubated at 37° C. for five hours. Wells were then aspirated and the cells resuspended in 2×SDS running buffer. Samples were sonicated at room temperature, and subjected to SDS-PAGE and Western blot analysis using an antibody specific for the cleaved Notch1 ICD according to the manufacturer's recommendations (Cell Signaling Technology, Danvers Mass.). Antibody 52M51 as well as antibodies 52M63, 52M74, and 52M80 significantly inhibited the generation of ICD after ligand stimulation (FIG. 1D).

Example 4

Evaluation of Anti-Notch1 Antibodies in a Leukemia Xenograft Model

Six- to eight-week old NOD/SCID mice received 350 rads total body irradiation from a Pantak HF320 X-ray machine with an MXR X-ray tube. Immediately thereafter, $1 \times 10^7$ human bone marrow mononuclear cells (MNCs) (Lonza, Walkersville Md.) were injected in 0.2 ml sterile phosphate-buffered saline (PBS) via tail vein. Seven days later, $5 \times 10^6$ viable primary human leukemia cells were suspended in 0.2 ml PBS and injected via tail vein. Starting one day later, the animals were treated with either control antibody (LZ1) or antibody that binds the membrane proximal region of the extracellular domain of human Notch1 (52M51). Antibodies were administered at a dose of 15 mg/kg i.p. once a week.

Five weeks after leukemia cell injection and antibody treatment, the level of engraftment of the leukemia cells in the mice was assessed by flow cytometry. Two-color immunofluorescence was used to identify human leukemia cells. Mouse spleens were analyzed for human cells using an antibody against the human CD45 marker. Cell suspensions of mouse spleens were lysed in Pharmlyse (BD Biosciences, San Jose Calif.) then washed and resuspended in HBSS plus 2% FBS. In every case, cells were stained with an antibody to CD34 (BD Biosciences, San Jose Calif.) in addition to antibody to CD45. A mouse antibody generated against human lysozyme (LZ-1) served as an isotype control antibody. Cells were also stained with DAPI as a marker of cell viability.

After staining, cells were washed, resuspended in HBSS plus 2% FBS and maintained on ice prior to analysis. Cells were analyzed using a Canto II flow cytometer (Beckman Coulter, Brea Calif.). Nonviable cells were gated out based on DAPI-uptake, matched isotype controls were run for each tissue sample and used to define gate settings, which excluded at least 99.9% of the cells in the isotype control. Spleens from naive NOD/SCID mice were used as additional controls to verify the gate settings. Human leukemia cell engraftment was defined as expression of at least 0.1% CD45-positive cells in a sample.

As shown in FIG. 2, mice injected with human leukemia cells and treated with anti-Notch1 antibody 52M51 had a significantly lower level of engraftment (39.7%, p<0.001) as compared to mice treated with a control antibody (61.8%).

Example 5

In Vitro Evaluation of Notch1 Inhibition in HPB-ALL Cells

HPB-ALL cells were acquired from DSMZ (Deutsche Sammlung von Mikroorganismen and Zellkulturen). The HPB-ALL cell line was established from the peripheral blood of a patient with acute lymphoblastic leukemia and thymoma and is classified as a human T cell leukemia. 5000 HPB-ALL cells were plated in each well of 96 well plates in growth medium (RPMI with 15% FBS) and treated with anti-Notch1 antibody 52M51 (-■-), a control antibody (-▼-) or dibenzazepine, a gamma secretase inhibitor (-●-). The antibodies were used at a concentration of 100 ug/ml with 3 fold serial dilutions to 1.7 ng/ml. Dibenzazepine was used at a concentration of 12 uM with 3 fold serial dilutions to 0.2 nM and served as a positive control. The samples were analyzed in triplicate and the experiment was repeated at least 4 times. After 8 days, cell viability was analyzed using CellTiter-Glo® Luminescent Cell Viability Assay according to manufacturer's instructions (Promega, Madison Wis.). As shown in FIG. 3, anti-Notch1 antibody 52M51 was able to reduce cell viability of HBP-ALL cells demonstrating that Notch1 inhibition could have an effect on human T-cell leukemia cells in vitro.

Example 6

In Vitro Evaluation of Notch1 Inhibition on Proliferation of HPB-ALL Cells

Ki67 is a nuclear antigen present in proliferating human cells and can be used to quantify the percentage of proliferating cells in a cell culture. HBP-ALL cells were cultured in the presence of 12 uM DBZ, 100 ug/ml of 52M51, or 100 ug/ml of control antibody. After 5 days the media was refreshed, and on day 9 the cells were analyzed for Ki67 protein. Briefly, cells were washed in PBS, fixed in a solution of 4% formaldehyde in PBS for 5 minutes. Cells were washed in PBS and permeabilized using PBS buffer containing 0.5% saponin and 2.5% BSA. Ki67 protein was detected with an anti-Ki67-FITC conjugate (BD Biosciences, San Jose Calif.). As shown in FIG. 4, anti-Notch1 antibody 52M51 reduced the percentage of proliferating HPB-ALL cells by approximately 40% as compared to cells treated with control antibody (60% Ki67 positive cells compared to 98% Ki67 positive cells).

Example 7

In Vitro Evaluation of Notch1 Inhibition on ICD Formation

HBP-ALL cells were cultured in presence of 12 uM DBZ, 100 ug/ml of 52M51, 100 ug/ml of A2G1 or 100 ug/ml of control antibody. After 5 days the medium was refreshed, and cells were harvested on day 9. Whole cell protein extracts were prepared with radioimmunoprecipitation assay buffer containing protease inhibitor cocktail (Roche Molecular, Pleasanton Calif.). Proteins were separated by SDS-polyacrylamide gel electrophoresis (PAGE) and were transferred to nitrocelluose membranes. The membranes were incubated in TBS-T (Tris-Buffered Saline plus 0.1% Tween 20) containing 5% nonfat milk to block non-specific binding. The membranes were then incubated with a rabbit monoclonal antibody which detects the intracellular domain (ICD) of Notch1 (clone D3B8, Cell Signaling Technology, Danvers, Mass.) for 1 hour at room temperature in PBS-T with 0.5% milk. The membrane was also probed with mouse anti-actin antibody (clone AC-15, Sigma, St. Louis Mo.). Bound primary antibody was detected with anti-rabbit/mouse HRP conjugate antibodies (Jackson ImmunoResearch Labs, West Grove Pa.) and visualized with ECL Plus™ Western Blotting reagent (GE Healthcare, Piscataway, N.J.). As shown in FIG. 5, anti-Notch antibody 52M51 reduced the amount of ICD formation in the treated HPB-ALL cells as compared to cells treated with control antibody.

Example 8

Inhibition of HPB-ALL Tumor Growth In Vivo by Anti-Notch1 Antibody 52M51

HPB-ALL cells ($7 \times 10^6$ cells) were injected subcutaneously into 6-8 week old NOD/SCID mice. Tumors were allowed to grow until the average tumor size was approximately 111 mm$^3$. On day 13 the animals were randomized into groups (n=10 per group) and treated with a control antibody (anti-lysozyme antibody LZ-1, -■-) or an anti-Notch1 antibody 52M51 (-▼-). Antibodies were administered at 15 mg/kg twice a week by intraperitoneal injection. Tumor growth was measured on the indicated days after treatment with electronic calipers. As shown in FIG. 6, treatment with anti-Notch1 antibody 52M51 resulted in significant reduction in growth of HPB-ALL tumors as compared to the control antibody (p<0.0001).

Example 9

Evaluation of Anti-Notch1 Antibodies in a Disseminated Leukemia Xenograft Model

HPB-ALL cells were used to establish disseminated leukemia xenografts in a mouse model. HPB-ALL cells ($5 \times 10^6$ cells) were injected into the lateral tail vein of 6-8 week old NOD/SCID mice. One day after leukemia cell injection the animals were randomized into groups (n=11-13 per group) and treated with a control antibody anti-lysozyme antibody LZ-1 (-■-) or anti-Notch1 antibody 52M51 (-▲-). Antibodies were administered in one dose at 15 mg/kg. Mice were monitored at least twice each week for signs of disease, including weight loss of 15% to 20%, hunched posture and lack of grooming, cranial swelling, and hind limb paralysis. On day 38, a portion of the mice in the control antibody treatment group displayed body weight loss of 15%, and all animals from both groups were sacrificed. The presence of human leukemia cells in spleen, peripheral blood and bone marrow was then determined.

5 weeks after leukemia cell injection and antibody treatment, the level of engraftment of the leukemia cells in the mice was assessed by flow cytometry. Two-color immunofluorescence was used to identify human leukemia cells. Bone marrow, spleens and peripheral blood were harvested from the mice and analyzed for human cells using an antibody against the human CD3 marker. Cell suspensions were lysed in Pharmlyse (BD Biosciences) then washed and resuspended in HBSS plus 2% FBS. Cells were stained with anti-mouse CD45-FITC and anti-mouse H-2K$^d$-FITC (clones 30F11 and SF1-1.1.1 respectively, eBioscience, San Diego Calif.) to enumerate murine cells and anti-human CD3-PE (clone OKT3, eBioscience, San Diego Calif.) to enumerate human leukemia cells. Cells were also stained with DAPI as a marker of cell viability.

After staining, cells were washed, resuspended in HBSS plus 2% FBS and maintained on ice prior to analysis. Cells were analyzed using a Canto II flow cytometer (Beckman Coulter, Brea Calif.). Nonviable cells were gated out based on DAPI-uptake, matched isotype controls were run for each tissue sample and used to define gate settings, which excluded at least 99.9% of the cells in the isotype control. Cells from naive NOD/SCID mice and in vitro cultured HPB-ALL cells were used as additional controls to verify the gate settings.

As shown in FIG. 7, treatment with anti-Notch1 antibody 52M51 resulted in a significant reduction in the percentage of HPB-ALL cells in bone marrow as compared to treatment with the control antibody. Animals treated with control antibody had a mean of 88% human CD3+ cells in their bone marrow as compared to a mean of 16% human CD3+ cells in animals treated with 52M51 (p<0.0001). In addition, anti-Notch1 antibody 52M51 reduced the percentage of HPB-ALL cells in the spleen and peripheral blood of treated animals as compared to animals treated with the control antibody. Animals treated with control antibody had a mean of 18% human CD3+ cells in their spleens as compared to an undetectable level in animals treated with 52M51. Similarly, animals treated with control antibody had a mean of 13% human CD3+ cells in their peripheral blood as compared to an undetectable level in animals treated with 52M51.

It is understood that the examples and embodiments described herein are for illustrative purposes only and that various modifications or changes in light thereof will be suggested to persons skilled in the art and are to be included within the spirit and purview of this application.

All publications, patents and patent applications cited herein are hereby incorporated by reference in their entirety for all purposes to the same extent as if each individual publication, patent or patent application were specifically and individually indicated to be so incorporated by reference.

Sequences

Notch1 Polynucleotide encoding amino acids 1427-1732.

SEQ ID NO: 1

```
CACATCCTGGACTACAGCTTCGGGGGTGGGGCCGGGCGCGACATCCCCC
CGCCGCTGATCGAGGAGGCGTGCGAGCTGCCCGAGTGCCAGGAGGACGC
GGGCAACAAGGTCTGCAGCCTGCAGTGCAACAACCACGCGTGCGGCTGG
GACGGCGGTGACTGCTCCCTCAACTTCAATGACCCCTGGAAGAACTGCA
CGCAGTCTCTGCAGTGCTGGAAGTACTTCAGTGACGGCCACTGTGACAG
CCAGTGCAACTCAGCCGGCTGCCTCTTCGACGGCTTTGACTGCCAGCGT
GCGGAAGGCCAGTGCAACCCCCTGTACGACCAGTACTGCAAGGACCACT
TCAGCGACGGGCACTGCGACCAGGGCTGCAACAGCGCGGAGTGCGAGTG
GGACGGCTGGACTGTGCGGAGCATGTACCCGAGAGGCTGGCGGCCGGC
ACGCTGGTGGTGGTGGTGCTGATGCCGCCGGAGCAGCTGCGCAACAGCT
CCTTCCACTTCCTGCGGGAGCTCAGCCGCGTGCTGCACACCAACGTGGT
CTTCAAGCGTGACGCACACGGCCAGCAGATGATCTTCCCCTACTACGGC
CGCGAGGAGGAGCTGCGCAAGCACCCCATCAAGCGTGCCGCCGAGGGCT
GGGCCGCACCTGACGCCCTGCTGGGCCAGGTGAAGGCCTCGCTGCTCCC
TGGTGGCAGCGAGGGTGGGCGGCGGCGGAGGGAGCTGGACCCCATGGAC
GTCCGCGGCTCCATCGTCTACCTGGAGATTGACAACCGGCAGTGTGTGC
AGGCCTCCTCGCAGTGCTTCCAGAGTGCCACCGACGTGGCCGCATTCCT
GGGAGCGCTCGCCTCGCTGGGCAGCCTCAACATCCCCTACAAGATCGAG
GCCGTGCAGAGTGAGACCGTGGAGCCGCCCCCGCCG
```

Notch1 amino acids 1427-1732

SEQ ID NO: 2

```
HILDYSFGGGAGRDIPPPLIEEACELPECQEDAGNKVCSLQCNNHACGW
DGGDCSLNFNDPWKNCTQSLQCWKYFSDGHCDSQCNSAGCLFDGFDCQR
AEGQCNPLYDQYCKDHFSDGHCDQGCNSAECEWDGLDCAEHVPERLAAG
TLVVVVLMPPEQLRNSSFHFLRELSRVLHTNVVFKRDAHGQQMIFPYYG
REEELRKHPIKRAAEGWAAPDALLGQVKASLLPGGSEGGRRRRELDPMD
VRGSIVYLEIDNRQCVQASSQCFQSATDVAAFLGALASLGSLNIPYKIE
AVQSETVEPPPP
```

Mouse Antibody 52M51 Sequences:

52M51 Light chain polynucleotide sequence (Putative signal sequence is underlined)

SEQ ID NO: 3

```
ATGGCCTGGATTTCACTTATACTCTCTCTCCTGGCTCTCAGCTCAGGGGCCATTTCCCAG
GCTGTTGTGACTCAGGAATCTGCACTCACCACATCACCTGGTGAAACAGTCACACTCACT
TGTCGCTCAAGTACTGGGGCTGTTACAACTAGTAACTACGCCAACTGGGTCCAAGAAAAA
CCTGATCATTTATTCACTGGTCTAATAGGTGGTACCAACAACCGAGCTCCAGGTGTTCCT
GCCAGATTCTCAGGCTCCCTGATTGGAGACAAGGCTGCCCTCACCATCACAGGGGCACAG
ACTGAGGATGAGGCAATATATTTCTGTGCTCTATGGTACAGCAACCACTGGGTGTTCGGT
GGAGGAACCAAACTGACTGTCCTAGGCCAGCCCAAGTCTTCGCCATCAGTCACCCTGTTT
CCACCTTCCTCTGAAGAGCTCGAGACTAACAAGGCCACACTGGTGTGTACGATCACTGAT
TTCTACCCAGGTGTGGTGACAGTGGACTGGAAGGTAGATGGTACCCCTGTCACTCAGGGT
ATGGAGACAACCCAGCCTTCCAAACAGAGCAACAACAAGTACATGGCTAGCAGCTACCTG
```

-continued

ACCCTGACAGCAAGAGCATGGGAAAGGCATAGCAGTTACAGCTGCCAGGTCACTCATGAA

GGTCACACTGTGGAGAAGAGTTTGTCCCGTGCTGACTGTTCCTAG

52M51 Light chain amino acid sequence (Putative signal sequence
is underlined)
SEQ ID NO: 4
<u>MAWISLILSLLALSSGAIS</u>QAVVTQESALTTSPGETVTLTCRSSTGAVTTSNYANWVQEK

PDHLFTGLIGGTNNRAPGVPARFSGSLIGDKAALTITGAQTEDEAIYFCALWYSNHWVFG

GGTKLTVLGQPKSSPSVTLFPPSSEELETNKATLVCTITDFYPGVVTVDWKVDGTPVTQG

METTQPSKQSNNKYMASSYLTLTARAWERHSSYSCQVTHEGHTVEKSLSRADCS

52M51 Light chain variable region polynucleotide sequence
(Putative signal sequence is underlined)
SEQ ID NO: 5
<u>ATGGCCTGGATTTCACTTATACTCTCTCCTGGCTCTCAGCTCAGGGGCCATTTCCCAG</u>

GCTGTTGTGACTCAGGAATCTGCACTCACCACATCACCTGGTGAAACAGTCACACTCACT

TGTCGCTCAAGTACTGGGGCTGTTACAACTAGTAACTACGCCAACTGGGTCCAAGAAAAA

CCTGATCATTTATTCACTGGTCTAATAGGTGGTACCAACAACCGAGCTCCAGGTGTTCCT

GCCAGATTCTCAGGCTCCCTGATTGGAGACAAGGCTGCCCTCACCATCACAGGGGCACAG

ACTGAGGATGAGGCAATATATTTCTGTGCTCTATGGTACAGCAACCACTGGGTGTTCGGT

GGAGGAACCAAACTGACTGTCCTAGGC

52M51 Light chain variable region amino acid sequence (Putative
signal sequence is underlined)
SEQ ID NO: 6
<u>MAWISLILSLLALSSGAIS</u>QAVVTQESALTTSPGETVTLTCRSSTGAVTTSNYANWVQEK

PDHLFTGLIGGTNNRAPGVPARFSGSLIGDKAALTITGAQTEDEAIYFCALWYSNHWVEG

GGTKLTVLGQPKSSPSVTLEPPSSEELETNKATLVCTITDFYPGVVTVDWKVDGTPVTQG

52M51 Light chain variable region polynucleotide sequence
without putative signal sequence
SEQ ID NO: 7
CAGGCTGTTGTGACTCAGGAATCTGCACTCACCACATCACCTGGTGAAACAGTCACACTC

ACTTGTCGCTCAAGTACTGGGGCTGTTACAACTAGTAACTACGCCAACTGGGTCCAAGAA

AAACCTGATCATTTATTCACTGGTCTAATAGGTGGTACCAACAACCGAGCTCCAGGTGTT

CCTGCCAGATTCTCAGGCTCCCTGATTGGAGACAAGGCTGCCCTCACCATCACAGGGGCA

CAGACTGAGGATGAGGCAATATATTTCTGTGCTCTATGGTACAGCAACCACTGGGTGTTC

GGTGGAGGAACCAAACTGACTGTCCTAGGC

52M51 Light chain variable region amino acid sequence without
putative signal sequence
SEQ ID NO: 8
QAVVTQESALTTSPGETVTLTCRSSTGAVTTSNYANWVQEKPDHLFTGLIGGTNNRAPGV

PARFSGSLIGDKAALTITGAQTEDEAIYFCALWYSNHWVFGGGTKLTVLG

52M51 Heavy chain polynucleotide sequence (Putative signal
sequence is underlined)
SEQ ID NO: 9
<u>ATGGAATGGACCTGGGTCTTTCTCTTCCTCCTGTCAGTAACTGCAGGTGTCCACTCCCAG</u>

GTTCAGCTGCAGCAGTCTGGAGCTGAGCTGATGAAGCCTGGGGCCTCAGTGAAGATATCC

TGCAAGGCTGCTGGCTACACAATGAGAGGCTACTGGATAGAGTGGATAAAGCAGAGGCCT

GGACATGGCCTTGAGTGGATTGGACAGATTTTACCTGGAACTGGGAGAACTAACTACAAT

GAGAAGTTCAAGGGCAAGGCCACATTCACTGCAGATACATCCTCCAACACAGCCAACATG

CAACTCAGCAGCCTGACATCTGAGGACTCTGCCGTCTATTACTGTGCAAGATTTGATGGT

AACTACGGTTACTATGCTATGGACTACTGGGGTCAAGGATCCTCAGTCACCGTCTCCTCA

-continued

```
GCCAAAACGACACCCCCATCTGTCTATCCACTGGCCCCTGGATCTGCTGCCCAAACTAAC

TCCATGGTGACCCTGGGATGCCTGGTCAAGGGCTATTTCCCTGAGCCAGTGACAGTGACC

TGGAACTCTGGATCCCTGTCCAGCGGTGTGCACACCTTCCCAGCTGTCCTGCAGTCTGAC

CTCTACACTCTGAGCAGCTCAGTGACTGTCCCCTCCAGCCCTCGGCCCAGCGAGACCGTC

ACCTGCAACGTTGCCCACCCGGCCAGCAGCACCAAGGTGGACAAGAAAATTGTGCCCAGG

GATTGTGGTTGTAAGCCTTGCATATGTACAGTCCCAGAAGTATCATCTGTCTTCATCTTC

CCCCCAAAGCCCAAGGATGTCCTCACCATTACTCTGACTCCTAAGGTCACGTGTGTTGTG

GTAGACATCAGCAAGGATGATCCCGAGGTCCAGTTCAGCTGGTTTGTAGATGATGTGGAG

GTGCACACAGCTCAGACGCAACCCCGGGAGGAGCAGTTCAACAGCACTTTCCGCTCAGTC

AGTGAACTTCCCATCATGCACCAGGACTGGCTCAATGGCAAGGAGTTCAAATGCAGGGTC

AACAGTGCAGCTTTCCCTGCCCCCATCGAGAAAACCATATCCAAAACCAAAGGCAGACCG

AAGGCTCCACAGGTGTACACCATTCCACCTCCCAAGGAGCAGATGGCCAAGGATAAAGTC

AGTCTGACCTGCATGATAACAGACTTCTTCCCTGAAGACATAACAGTGGAGTGGCAGTGG

AATGGGCAGCCAGCGGAGAACTACAAGAACACTCAGCCCATCATGAACACGAATGGCTCT

TACTTCGTCTACAGCAAGCTCAATGTGCAGAAGAGCAACTGGGAGGCAGGAAATACTTTC

ACCTGCTCTGTGTTACATGAGGGCCTGCACAACCACCATACTGAGAAGAGCCTCTCCCAC

TCTCCTGGTAAATGA
```

52M51 Heavy chain amino acid sequence (Putative signal sequence is underlined)

SEQ ID NO: 10

<u>MEWTWVFLFLLSVTAGVHS</u>QVQLQQSGAELMKPGASVKISCKAAGYTMRGYWIEWIKQRP

GHGLEWIGQILPGTGRTNYNEKFKGKATFTADTSSNTANMQLSSLTSEDSAVYYCARFDG

NYGYYAMDYWGQGSSVTVSSAKTTPPSVYPLAPGSAAQTNSMVTLGCLVKGYFPEPVTVT

WNSGSLSSGVHTFPAVLQSDLYTLSSSVTVPSSPRPSETVTCNVAHPASSTKVDKKIVPR

DCGCKPCICTVPEVSSVFIFPPKPKDVLTITLTPKVTCVVVDISKDDPEVQFSWFVDDVE

VHTAQTQPREEQFNSTFRSVSELPIMHQDWLNGKEFKCRVNSAAFPAPIEKTISKTGRP

KAPQVYTIPPPKEQMAKDKVSLTCMITDFFPEDITVEWQWNGQPAENYKNTQPIMNTNGS

YFVYSKLNVQKSNWEAGNTFTCSVLHEGLHNHHTEKSLSHSPGK

52M51 Heavy chain variable region polynucleotide sequence (Putative signal sequence is underlined)

SEQ ID NO: 11

<u>ATGGAATGGACCTGGGTCTTTCTCTTCCTCCTGTCAGTAACTGCAGGTGTCCACTCCCAG</u>

GTTCAGCTGCAGCAGTCTGGAGCTGAGCTGATGAAGCCTGGGGCCTCAGTGAAGATATCC

TGCAAGGCTGCTGGCTACACAATGAGAGGCTACTGGATAGAGTGGATAAAGCAGAGGCCT

GGACATGGCCTTGAGTGGATTGGACAGATTTTACCTGGAACTGGGAGAACTAACTACAAT

GAGAAGTTCAAGGGCAAGGCCACATTCACTGCAGATACATCCTCCAACACAGCCAACATG

CAACTCAGCAGCCTGACATCTGAGGACTCTGCCGTCTATTACTGTGCAAGATTTGATGGT

AACTACGGTTACTATGCTATGGACTACTGGGGTCAAGGATCCTCAGTCACCGTCTCCTCA

52M51 Heavy chain variable region amino acid sequence (Putative signal sequence is underlined)

SEQ ID NO: 12

<u>MEWTWVFLFLLSVTAGVHS</u>QVQLQQSGAELMKPGASVKISCKAAGYTMRGYWIEWIKQRP

GHGLEWIGQILPGTGRTNYNEKFKGKATFTADTSSNTANMQLSSLTSEDSAVYYCARFDG

NYGYYAMDYWGQGSSVTVSSAKTTPPSVYPLAPGSAAQTNSMVTLGCLVKGYFPEPVTVT

```
52M51 Heavy chain variable region polynucleotide sequence
without putative signal sequence
                                             SEQ ID NO: 13
CAGGTTCAGCTGCAGCAGTCTGGAGCTGAGCTGATGAAGCCTGGGGCCTCAGTGAAGATA

TCCTGCAAGGCTGCTGGCTACACAATGAGAGGCTACTGGATAGAGTGGATAAAGCAGAGG

CCTGGACATGGCCTTGAGTGGATTGGACAGATTTTACCTGGAACTGGGAGAACTAACTAC

AATGAGAAGTTCAAGGGCAAGGCCACATTCACTGCAGATACATCCTCCAACACAGCCAAC

ATGCAACTCAGCAGCCTGACATCTGAGGACTCTGCCGTCTATTACTGTGCAAGATTTGAT

GGTAACTACGGTTACTATGCTATGGACTACTGGGGTCAAGGATCCTCAGTCACCGTCTCC

TCA

52M51 Heavy chain variable region amino acid sequence without
putative signal sequence
                                             SEQ ID NO: 14
QVQLQQSGAELMKPGASVKISCKAAGYTMRGYWIEWIKQRPGHGLEWIGQILPGTGRTNY

NEKFKGKATFTADTSSNTANMQLSSLTSEDSAVYYCARFDGNYGYYAMDYWGQGSSVTVS

SA

52M51 Heavy chain CDR1
                                             SEQ ID NO: 15
RGYWIE 52M51 Heavy chain CDR2
                                             SEQ ID NO: 16
QILPGTGRTNYNEKFKG 52M51 Heavy chain CDR3
                                             SEQ ID NO: 17
FDGNYGYYAMDY 52M51 Light chain CDR1
                                             SEQ ID NO: 18
RSSTGAVTTSNYAN 52M51 Light chain CDR2
                                             SEQ ID NO: 19
GTNNRAP 52M51 Light chain CDR3
                                             SEQ ID NO: 20
ALWYSNHWVFGGGTKL
```

Humanized 52M51 Sequences:

```
52M51-H4 Heavy chain polynucleotide sequence (Putative signal
sequence underlined)
                                             SEQ ID NO: 21
ATGGATTGGACATGGAGGGTGTTCTGCCTCCTCGCTGTGGCTCCTGGAGTCCTGAGCCAG

GTCCAGCTCGTCCAGAGCGGGGCTGAAGTCAAGAAGCCTGGCGCTAGCGTCAAAATCAGC

TGTAAGGTCAGCGGATACACACTGAGGGGATACTGGATCGAGTGGGTGAGGCAGGCTCCA

GGAAAGGGCCTGGAATGGATCGGCCAGATCCTGCCTGGAACCGGAAGGACAAATTACAAT

GAGAAGTTTAAGGGAAGGGTCACAATGACAGCAGACACAAGCACAGACACAGCTTATATG

GAACTCAGCTCCCTCAGATCCGAGGACACCGCTGTCTACTATTGTGCCAGGTTCGATGGA

AATTACGGATACTATGCCATGGATTACTGGGGACAGGGGACAACGGTCACCGTGAGCTCA

GCCAGCACAAAGGGCCCTAGCGTCTTCCCTCTGGCTCCCTGCAGCAGGAGCACCAGCGAG

AGCACAGCCGCCCTGGGCTGCCTGGTCAAGGACTACTTCCCCGAACCGGTGACGGTGTCG

TGGAACTCAGGCGCTCTGACCAGCGGCGTGCACACCTTCCCAGCTGTCCTACAGTCCTCA

GGACTCTACTCCCTCAGCAGCGTGGTGACCGTGCCCTCCAGCAACTTCGGCACCCAGACC

TACACCTGCAACGTAGATCACAAGCCCAGCAACACCAAGGTGGACAAGACAGTTGAGCGC
```

-continued

```
AAATGTTGTGTCGAGTGCCCACCGTGCCCAGCACCACCTGTGGCAGGACCGTCAGTCTTC

CTCTTCCCCCCAAAACCCAAGGACACCCTCATGATCTCCCGGACCCCTGAGGTCACGTGC

GTGGTGGTGGACGTGAGCCACGAAGACCCCGAGGTCCAGTTCAACTGGTACGTGGACGGC

GTGGAGGTGCATAATGCCAAGACAAAGCCACGGGAGGAGCAGTTCAACAGCACGTTCCGT

GTGGTCAGCGTCCTCACCGTTGTGCACCAGGACTGGCTGAACGGCAAGGAGTACAAGTGC

AAGGTCTCCAACAAAGGCCTCCCAGCCCCCATCGAGAAAACCATCTCCAAAACCAAAGGG

CAGCCCCGAGAACCACAGGTGTACACCCTGCCCCCATCCCGGGAGGAGATGACCAAGAAC

CAGGTCAGCCTGACCTGCCTGGTCAAAGGCTTCTACCCCAGCGACATCGCCGTGGAGTGG

GAGAGCAATGGGCAGCCGGAGAACAACTACAAGACCACACCTCCCATGCTGGACTCCGAC

GGCTCCTTCTTCCTCTACAGCAAGCTCACCGTGGACAAGAGCAGGTGGCAGCAGGGGAAC

GTCTTCTCATGCTCCGTGATGCATGAGGCTCTGCACAACCACTACACGCAGAAGAGCCTC

TCCCTGTCTCCGGGTAAATGA
```

52M51 H4 Heavy chain amino acid sequence (Putative signal
sequence underlined)
SEQ ID NO: 22

<u>MDWTWRVFCLLAVAPGVLS</u>QVQLVQSGAEVKKPGASVKISCKVSGYTLRGYWIEWVRQAP

GKGLEWIGQILPGTGRTNYNEKFKGRVTMTADTSTDTAYMELSSLRSEDTAVYYCARFDG

NYGYYAMDYWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDPEVQFNWYVDG

VEVHNAKTKPREEQFNSTERVVSVLTVVHQDWLNGKEYKCKVSNKGLPAPIEKTISKTKG

QPREPQVYTLPPSREEMTKNQVSLTCLVKGFYPSDIAVEWESNGQPENNYKTTPPMLDSD

GSFFLYSKLTVDKSRWQQGNVFSCSVMHEALHNHYTQKSLSLSPGK

52M51-H4 Heavy chain variable region amino acid sequence
(Putative signal sequence underlined)
SEQ ID NO: 23

<u>MDWTWRVFCLLAVAPGVLS</u>QVQLVQSGAEVKKPGASVKISCKVSGYTLRGYWIEWVRQAP

GKGLEWIGQILPGTGRTNYNEKFKGRVTMTADTSTDTAYMELSSLRSEDTAVYYCARFDG

NYGYYAMDYWGQGTTVTVSSA

52M51-H4 Heavy chain variable region amino acid sequence without
putative signal sequence
SEQ ID NO: 24

QVQLVQSGAEVKKPGASVKISCKVSGYTLRGYWIEWVRQAPGKGLEWIGQILPGTGRTNY

NEKFKGRVTMTADTSTDTAYMELSSLRSEDTAVYYCARFDGNYGYYAMDYWGQGTTVTVS

SA

52M51-L3 Light chain polynucleotide sequence (Putative signal
sequence is underlined)
SEQ ID NO: 25

<u>ATGAGCGTCCCTACAATGGCTTGGATGATGCTCCTGCTGGGACTCCTGGCTTATGGAAGC</u>

GGAGTGGATAGCCAGGCCGTCGTCACACAGGAACCTAGCCTCACCGTTAGCCCTGGAGGA

ACAGTCACACTGACCTGTAGGAGCTCCACAGGAGCTGTGACAACAAGCAATTACGCTAAC

TGGTTCCAGCAGAAGCCCGGTCAAGCCCCTAGAACCCTCATCGGCGGCACCAATAACAGA

GCTCCCGGAGTCCCCGCCAGGTTCTCCGGCTCCCTCCTGGGTGGCAAGGCTGCTCTGACA

CTCAGCGGTGCCCAGCCAGAGGATGAAGCGGAGTACTACTGTGCACTGTGGTACAGCAAC

CATTGGGTTTTCGGAGGCGGAACAAAGTTAACCGTCCTCGGGCAGCCTAAGGCTGCTCCT

AGCGTCACACTGTTCCCCCCATCTAGCGAGGAGCTGCAGGCTAACAAGGCAACCCTCGTC

TGCCTGGTTAGCGACTTCTACCCTGGCGCTGTCACAGTGGCCTGGAAAGCTGACGGCTCC
```

-continued

```
CCTGTGAAAGTTGGCGTCGAAACCACAAAGCCTTCTAAGCAGAGCAATAATAAATATGCC

GCAAGCTCCTACCTCTCCCTGACTCCTGAGCAGTGGAAAAGCCATAGGAGCTACTCCTGC

CGGGTCACACACGAAGGAAGCACAGTGGAAAAGACAGTCGCCCCTGCTGAGTGTAGCTGA
```

52M51-L3 Light chain amino acid sequence (Putative signal
sequence is underlined)
SEQ ID NO: 26

<u>MSVPTMAWMMLLLGLLAYG</u>SGVDSQAVVTQEPSLTVSPGGTVTLTCRSSTGAVTTSNYAN

WFQQKPGQAPRTLIGGTNNRAPGVPARFSGSLLGGKAALTLSGAQPEDEAEYYCALWYSN

HWVFGGGTKLTVLGQPKAAPSVTLFPPSSEELQANKATLVCLVSDFYPGAVTVAWKADGS

PVKVGVETTKPSKQSNNKYAASSYLSLTPEQWKSHRSYSCRVTHEGSTVEKTVAPAECS

52M51-L3 Light chain variable region amino acid sequence
(Putative signal sequence is underlined)
SEQ ID NO: 27

<u>MSVPTMAWMMLLLGLLAYG</u>SGVDSQAVVTQEPSLTVSPGGTVTLTCRSSTGAVTTSNYAN

WFQQKPGQAPRTLIGGTNNRAPGVPARFSGSLLGGKAALTLSGAQPEDEAEYYCALWYSN

HWVFGGGTKLTVLG

52M51-L3 Light chain variable region amino acid sequence without
putative signal sequence
SEQ ID NO: 28

SGVDSQAVVTQEPSLTVSPGGTVTLTCRSSTGAVTTSNYANWFQQKPGQAPRTLIGGTNN

RAPGVPARFSGSLLGGKAALTLSGAQPEDEAEYYCALWYSNHWVFGGGTKLTVLG

52M51-L4 Light chain polynucleotide sequence (Putative signal
sequence is underlined)
SEQ ID NO: 29

<u>ATGAGCGTCCCTACAATGGCTTGGATGATGCTCCTGCTGGGACTCCTGGCTTATGGAAGC</u>

```
GGAGTGGATAGCCAGACCGTCGTCACACAGGAACCTAGCTTTTCCGTTAGCCCTGGAGGA

ACAGTCACACTGACCTGTAGGAGCTCCACAGGAGCTGTGACAACAAGCAATTACGCTAAC

TGGTATCAGCAGACTCCCGGTCAAGCCCCTAGAACCCTCATCGGCGGCACCAATAACAGA

GCTCCCGGAGTCCCCGACAGGTTCTCCGGCTCCATCCTGGGAAATAAAGCTGCTCTGACA

ATCACAGGTGCCCAGGCTGACGATGAAAGCGACTACTACTGTGCACTGTGGTACAGCAAC

CATTGGGTTTTCGGAGGCGGAACAAAGTTAACCGTCCTCGGGCAGCCTAAGGCTGCTCCT

AGCGTCACACTGTTCCCCCCATCTAGCGAGGAGCTGCAGGCTAACAAGGCAACCCTCGTC

TGCCTGGTTAGCGACTTCTACCCTGGCGCTGTCACAGTGGCCTGGAAAGCTGACGGCTCC

CCTGTGAAAGTTGGCGTCGAAACCACAAAGCCTTCTAAGCAGAGCAATAATAAATATGCC

GCAAGCTCCTACCTCTCCCTGACTCCTGAGCAGTGGAAAAGCCATAGGAGCTACTCCTGC

CGGGTCACACACGAAGGAAGCACAGTGGAAAAGACAGTCGCCCCTGCTGAGTGTAGCTGA
```

52M51-L4 Light chain amino acid sequence (Putative signal
sequence is underlined)
SEQ ID NO: 30

<u>MSVPTMAWMMLLLGLLAYG</u>SGVDSQTVVTQEPSFSVSPGGTVTLTCRSSTGAVTTSNYAN

WYQQTPGQAPRTLIGGTNNRAPGVPDRFSGSILGNKAALTITGAQADDESDYYCALWYSN

HWVFGGGTKLTVLGQPKAAPSVTLFPPSSEELQANKATLVCLVSDFYPGAVTVAWKADGS

PVKVGVETTKPSKQSNNKYAASSYLSLTPEQWKSHRSYSCRVTHEGSTVEKTVAPAECS

-continued

52M51-L4 Light chain variable region amino acid sequence
(Putative signal sequence is underlined)

SEQ ID NO: 31

<u>MSVPTMAWMMLLLGLLAYG</u>SGVDSQTVVTQEPSFSVSPGGTVTLTCRSSTGAVTTSNYAN

WYQQTPGQAPRTLIGGTNNRAPGVPDRFSGSILGNKAALTITGAQADDESDYYCALWYSN

HWVFGGGTKLTVLG

52M51-L4 Light chain variable region amino acid sequence without
putative signal sequence

SEQ ID NO: 32

SGVDSQTVVTQEPSFSVSPGGTVTLTCRSSTGAVTTSNYANWYQQTPGQAPRTLIGGTNN

RAPGVPDRFSGSILGNKAALTITGAQADDESDYYCALWYSNHWVFGGGTKLTVLG

FLAG-tag

SEQ ID NO: 33

DYKDDDK

---

SEQUENCE LISTING

<160> NUMBER OF SEQ ID NOS: 33

<210> SEQ ID NO 1
<211> LENGTH: 918
<212> TYPE: DNA
<213> ORGANISM: Artificial Sequence
<220> FEATURE:
<223> OTHER INFORMATION: Notch1 Polynucleotide encoding amino acids
      1427-1732

<400> SEQUENCE: 1

```
cacatcctgg actacagctt cgggggtggg gccgggcgcg acatccccccc gccgctgatc      60 gaggaggcgt gcgagctgcc cgagtgccag gaggacgcgg gcaacaaggt ctgcagcctg     120
cagtgcaaca accacgcgtg cggctgggac ggcggtgact gctccctcaa cttcaatgac     180
ccctggaaga actgcacgca gtctctgcag tgctggaagt acttcagtga cggccactgt     240
gacagccagt gcaactcagc cggctgcctc ttcgacggct tgactgcca gcgtgcggaa      300 ggccagtgca ccccctgta cgaccagtac tgcaaggacc acttcagcga cgggcactgc     360
gaccagggct gcaacagcgc ggagtgcgag tgggacgggc tggactgtgc ggagcatgta     420
cccgagaggc tggcggccgg cacgctggtg gtggtggtgc tgatgccgcc ggagcagctg     480
cgcaacagct ccttccactt cctgcgggag ctcagccgcg tgctgcacac caacgtggtc     540
ttcaagcgtg acgcacacgg ccagcagatg atcttcccct actacggccg cgaggaggag     600
ctgcgcaagc accccatcaa gcgtgccgcc gagggctggg ccgcacctga cgccctgctg     660
ggccaggtga aggcctcgct gctccctggt ggcagcgagg gtgggcggcg gcggagggag     720
ctggacccca tggacgtccg cggctccatc gtctacctgg agattgacaa ccggcagtgt     780
gtgcaggcct cctcgcagtg cttccagagt gccaccgacg tggccgcatt cctgggagcg     840
ctcgcctcgc tgggcagcct caacatcccc tacaagatcg aggccgtgca gagtgagacc     900
gtggagccgc ccccgccg                                                   918
```

<210> SEQ ID NO 2
<211> LENGTH: 306
<212> TYPE: PRT
<213> ORGANISM: Artificial Sequence
<220> FEATURE:
<223> OTHER INFORMATION: Notch1 amino acids 1427-1732

<400> SEQUENCE: 2

His Ile Leu Asp Tyr Ser Phe Gly Gly Gly Ala Gly Arg Asp Ile Pro

```
  1               5                  10                 15
Pro Pro Leu Ile Glu Glu Ala Cys Glu Leu Pro Glu Cys Gln Glu Asp
              20                  25                  30

Ala Gly Asn Lys Val Cys Ser Leu Gln Cys Asn Asn His Ala Cys Gly
          35                  40                  45

Trp Asp Gly Asp Cys Ser Leu Asn Phe Asn Pro Trp Lys Asn
 50                  55                  60

Cys Thr Gln Ser Leu Gln Cys Trp Lys Tyr Phe Ser Asp Gly His Cys
 65                  70                  75                  80

Asp Ser Gln Cys Asn Ser Ala Gly Cys Leu Phe Asp Gly Phe Asp Cys
                  85                  90                  95

Gln Arg Ala Glu Gly Gln Cys Asn Pro Leu Tyr Asp Gln Tyr Cys Lys
              100                 105                 110

Asp His Phe Ser Asp Gly His Cys Asp Gln Gly Cys Asn Ser Ala Glu
              115                 120                 125

Cys Glu Trp Asp Gly Leu Asp Cys Ala Glu His Val Pro Glu Arg Leu
         130                 135                 140

Ala Ala Gly Thr Leu Val Val Val Leu Met Pro Pro Glu Gln Leu
145                 150                 155                 160

Arg Asn Ser Ser Phe His Phe Leu Arg Glu Leu Ser Arg Val Leu His
                  165                 170                 175

Thr Asn Val Val Phe Lys Arg Asp Ala His Gly Gln Gln Met Ile Phe
              180                 185                 190

Pro Tyr Tyr Gly Arg Glu Glu Leu Arg Lys His Pro Ile Lys Arg
          195                 200                 205

Ala Ala Glu Gly Trp Ala Ala Pro Asp Ala Leu Leu Gly Gln Val Lys
 210                 215                 220

Ala Ser Leu Leu Pro Gly Gly Ser Glu Gly Gly Arg Arg Arg Arg Glu
225                 230                 235                 240

Leu Asp Pro Met Asp Val Arg Gly Ser Ile Val Tyr Leu Glu Ile Asp
              245                 250                 255

Asn Arg Gln Cys Val Gln Ala Ser Ser Gln Cys Phe Gln Ser Ala Thr
              260                 265                 270

Asp Val Ala Ala Phe Leu Gly Ala Leu Ala Ser Leu Gly Ser Leu Asn
              275                 280                 285

Ile Pro Tyr Lys Ile Glu Ala Val Gln Ser Glu Thr Val Glu Pro Pro
          290                 295                 300

Pro Pro
305

<210> SEQ ID NO 3
<211> LENGTH: 705
<212> TYPE: DNA
<213> ORGANISM: Mus musculus
<220> FEATURE:
<223> OTHER INFORMATION: 52M51 Light chain polynucleotide sequence

<400> SEQUENCE: 3
atggcctgga tttcacttat actctctctc ctggctctca gctcaggggc catttcccag      60
gctgttgtga ctcaggaatc tgcactcacc acatcacctg gtgaaacagt cacactcact     120
tgtcgctcaa gtactggggc tgttacaact agtaactacg ccaactgggt ccaagaaaaa     180
cctgatcatt tattcactgg tctaataggt ggtaccaaca accgagctcc aggtgttcct     240
gccagattct caggctccct gattggagac aaggctgccc tcaccatcac aggggcacag     300
```

```
actgaggatg aggcaatata tttctgtgct ctatggtaca gcaaccactg ggtgttcggt    360
ggaggaacca aactgactgt cctaggccag cccaagtctt cgccatcagt caccctgttt    420
ccaccttcct ctgaagagct cgagactaac aaggccacac tggtgtgtac gatcactgat    480
ttctacccag gtgtggtgac agtggactgg aaggtagatg gtacccctgt cactcagggt    540
atggagacaa cccagccttc aaacagagc aacaacaagt acatggctag cagctacctg    600
accctgacag caagagcatg ggaaaggcat agcagttaca gctgccaggt cactcatgaa    660
ggtcacactg tggagaagag tttgtcccgt gctgactgtt cctag                    705
```

<210> SEQ ID NO 4
<211> LENGTH: 234
<212> TYPE: PRT
<213> ORGANISM: Mus musculus
<220> FEATURE:
<223> OTHER INFORMATION: 52M51 Light chain amino acid sequence

<400> SEQUENCE: 4

```
Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125

Gly Gln Pro Lys Ser Ser Pro Ser Val Thr Leu Phe Pro Pro Ser Ser
    130                 135                 140

Glu Glu Leu Glu Thr Asn Lys Ala Thr Leu Val Cys Thr Ile Thr Asp
145                 150                 155                 160

Phe Tyr Pro Gly Val Val Thr Val Asp Trp Lys Val Asp Gly Thr Pro
                165                 170                 175

Val Thr Gln Gly Met Glu Thr Thr Gln Pro Ser Lys Gln Ser Asn Asn
            180                 185                 190

Lys Tyr Met Ala Ser Ser Tyr Leu Thr Leu Thr Ala Arg Ala Trp Glu
        195                 200                 205

Arg His Ser Ser Tyr Ser Cys Gln Val Thr His Glu Gly His Thr Val
    210                 215                 220

Glu Lys Ser Leu Ser Arg Ala Asp Cys Ser
225                 230
```

<210> SEQ ID NO 5
<211> LENGTH: 387
<212> TYPE: DNA
<213> ORGANISM: Mus musculus
<220> FEATURE:
<223> OTHER INFORMATION: 52M51 Light chain variable region
      polynucleotide sequence

<400> SEQUENCE: 5

```
atggcctgga tttcacttat actctctctc ctggctctca gctcagggc catttcccag    60 gctgttgtga ctcaggaatc tgcactcacc acatcacctg gtgaaacagt cacactcact   120
tgtcgctcaa gtactgggc tgttacaact agtaactacg ccaactgggt ccaagaaaaa   180
cctgatcatt tattcactgg tctaataggt ggtaccaaca accgagctcc aggtgttcct   240
gccagattct caggctccct gattggagac aaggctgccc tcaccatcac aggggcacag   300
actgaggatg aggcaatata tttctgtgct ctatggtaca gcaaccactg ggtgttcggt   360
ggaggaacca aactgactgt cctaggc                                       387
```

<210> SEQ ID NO 6
<211> LENGTH: 180
<212> TYPE: PRT
<213> ORGANISM: Mus musculus
<220> FEATURE:
<223> OTHER INFORMATION: 52M51 Light chain variable region amino acid
      sequence

<400> SEQUENCE: 6

```
Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125

Gly Gln Pro Lys Ser Ser Pro Ser Val Thr Leu Phe Pro Pro Ser Ser
    130                 135                 140

Glu Glu Leu Glu Thr Asn Lys Ala Thr Leu Val Cys Thr Ile Thr Asp
145                 150                 155                 160

Phe Tyr Pro Gly Val Val Thr Val Asp Trp Lys Val Asp Gly Thr Pro
                165                 170                 175

Val Thr Gln Gly
            180
```

<210> SEQ ID NO 7
<211> LENGTH: 330
<212> TYPE: DNA
<213> ORGANISM: Mus musculus
<220> FEATURE:
<223> OTHER INFORMATION: 52M51 Light chain variable region
      polynucleotide sequence without putative signal sequence

<400> SEQUENCE: 7

```
caggctgttg tgactcagga atctgcactc accacatcac ctggtgaaac agtcacactc    60
acttgtcgct caagtactgg ggctgttaca actagtaact acgccaactg ggtccaagaa   120
aaacctgatc atttattcac tggtctaata ggtggtacca caaccgagc tccaggtgtt   180
```

```
cctgccagat tctcaggctc cctgattgga gacaaggctg ccctcaccat cacaggggca      240
cagactgagg atgaggcaat atatttctgt gctctatggt acagcaacca ctgggtgttc      300
ggtggaggaa ccaaactgac tgtcctaggc                                      330
```

```
<210> SEQ ID NO 8
<211> LENGTH: 110
<212> TYPE: PRT
<213> ORGANISM: Mus musculus
<220> FEATURE:
<223> OTHER INFORMATION: 52M51 Light chain variable region amino
      acid sequence without putative signal sequence

<400> SEQUENCE: 8
```

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly
            100                 105                 110
```

```
<210> SEQ ID NO 9
<211> LENGTH: 1395
<212> TYPE: DNA
<213> ORGANISM: Mus musculus
<220> FEATURE:
<223> OTHER INFORMATION: 52M51 Heavy chain polynucleotide sequence

<400> SEQUENCE: 9
```

```
atggaatgga cctgggtctt tctcttcctc ctgtcagtaa ctgcaggtgt ccactcccag       60
gttcagctgc agcagtctgg agctgagctg atgaagcctg ggcctcagt gaagatatcc      120 tgcaaggctg ctggctacac aatgagaggc tactggatag agtggataaa gcagaggcct      180
ggacatggcc ttgagtggat tggacagatt ttacctggaa ctgggagaac taactacaat      240
gagaagttca gggcaaggc cacattcact gcagatacat cctccaacac agccaacatg      300
caactcagca gcctgacatc tgaggactct gccgtctatt actgtgcaag atttgatggt      360
aactacggtt actatgctat ggactactgg ggtcaaggat cctcagtcac cgtctcctca      420
gccaaaacga caccccatc tgtctatcca ctggcccctg gatctgctgc ccaaactaac      480
tccatggtga ccctgggatg cctggtcaag ggctatttcc ctgagccagt gacagtgacc      540
tggaactctg gatccctgtc cagcggtgtg cacaccttcc cagctgtcct gcagtctgac      600
ctctacactc tgagcagctc agtgactgtc ccctccagcc tcggcccag cgagaccgtc      660 acctgcaacg ttgcccaccc ggccagcagc accaaggtgg acaagaaaat tgtgcccagg      720
gattgtggtt gtaagccttg catatgtaca gtcccagaag tatcatctgt cttcatcttc      780
cccccaaagc ccaaggatgt cctcaccatt actctgactc ctaaggtcac gtgtgttgtg      840
gtagacatca gcaaggatga tcccgaggtc cagttcagct ggtttgtaga tgatgtggag      900
gtgcacacag ctcagacgca accccgggag gagcagttca acagcacttt ccgctcagtc      960
```
agtgaacttc ccatcatgca ccaggactgg ctcaatggca aggagttcaa atgcagggtc  1020
aacagtgcag ctttccctgc ccccatcgag aaaaccatat ccaaaaccaa aggcagaccg  1080
aaggctccac aggtgtacac cattccacct cccaaggagc agatggccaa ggataaagtc  1140
agtctgacct gcatgataac agacttcttc cctgaagaca taacagtgga gtggcagtgg  1200
aatgggcagc cagcggagaa ctacaagaac actcagccca tcatgaacac gaatggctct  1260
tacttcgtct acagcaagct caatgtgcag aagagcaact gggaggcagg aaatactttc  1320
acctgctctg tgttacatga gggcctgcac aaccaccata ctgagaagag cctctcccac  1380
tctcctggta aatga  1395

<210> SEQ ID NO 10
<211> LENGTH: 464
<212> TYPE: PRT
<213> ORGANISM: Mus musculus
<220> FEATURE:
<223> OTHER INFORMATION: 52M51 Heavy chain amino acid sequence

<400> SEQUENCE: 10

```
Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Ala Gly Tyr Thr Met
        35                  40                  45

Arg Gly Tyr Trp Ile Glu Trp Ile Lys Gln Arg Pro Gly His Gly Leu
    50                  55                  60

Glu Trp Ile Gly Gln Ile Leu Pro Gly Thr Gly Arg Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Asn Met Gln Leu Ser Ser Leu Thr Ser Glu Asp Ser Ala Val
            100                 105                 110

Tyr Tyr Cys Ala Arg Phe Asp Gly Asn Tyr Gly Tyr Tyr Ala Met Asp
        115                 120                 125

Tyr Trp Gly Gln Gly Ser Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Pro Arg Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
```

```
                275                 280                 285
Glu Val Gln Phe Ser Trp Phe Asp Asp Val Glu Val His Thr Ala
    290                 295                 300
Gln Thr Gln Pro Arg Glu Gln Phe Asn Ser Thr Phe Arg Ser Val
305                 310                 315                 320
Ser Glu Leu Pro Ile Met His Gln Asp Trp Leu Asn Gly Lys Glu Phe
                325                 330                 335
Lys Cys Arg Val Asn Ser Ala Ala Phe Pro Ala Pro Ile Glu Lys Thr
                340                 345                 350
Ile Ser Lys Thr Lys Gly Arg Pro Lys Ala Pro Gln Val Tyr Thr Ile
                355                 360                 365
Pro Pro Pro Lys Glu Gln Met Ala Lys Asp Lys Val Ser Leu Thr Cys
    370                 375                 380
Met Ile Thr Asp Phe Phe Pro Glu Asp Ile Thr Val Glu Trp Gln Trp
385                 390                 395                 400
Asn Gly Gln Pro Ala Glu Asn Tyr Lys Asn Thr Gln Pro Ile Met Asn
                405                 410                 415
Thr Asn Gly Ser Tyr Phe Val Tyr Ser Lys Leu Asn Val Gln Lys Ser
                420                 425                 430
Asn Trp Glu Ala Gly Asn Thr Phe Thr Cys Ser Val Leu His Glu Gly
                435                 440                 445
Leu His Asn His His Thr Glu Lys Ser Leu Ser His Ser Pro Gly Lys
    450                 455                 460

<210> SEQ ID NO 11
<211> LENGTH: 420
<212> TYPE: DNA
<213> ORGANISM: Mus musculus
<220> FEATURE:
<223> OTHER INFORMATION: 52M51 Heavy chain variable region
      polynucleotide sequence

<400> SEQUENCE: 11
atggaatgga cctgggtctt tctcttcctc ctgtcagtaa ctgcaggtgt ccactcccag      60
gttcagctgc agcagtctgg agctgagctg atgaagcctg gggcctcagt gaagatatcc     120
tgcaaggctg ctggctacac aatgagaggc tactggatag agtggataaa gcagaggcct     180
ggacatggcc ttgagtggat tggacagatt ttacctggaa ctgggagaac taactacaat     240
gagaagttca gggcaaggc cacattcact gcagatacat cctccaacac agccaacatg     300
caactcagca gcctgacatc tgaggactct gccgtctatt actgtgcaag atttgatggt     360
aactacggtt actatgctat ggactactgg ggtcaaggat cctcagtcac cgtctcctca     420

<210> SEQ ID NO 12
<211> LENGTH: 180
<212> TYPE: PRT
<213> ORGANISM: Mus musculus
<220> FEATURE:
<223> OTHER INFORMATION: 52M51 Heavy chain variable region amino acid
      sequence

<400> SEQUENCE: 12

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Ala Gly Tyr Thr Met
        35                  40                  45
```

Arg Gly Tyr Trp Ile Glu Trp Ile Lys Gln Arg Pro Gly His Gly Leu
        50                  55                  60

Glu Trp Ile Gly Gln Ile Leu Pro Gly Thr Gly Arg Thr Asn Tyr Asn
 65                  70                  75                  80

Glu Lys Phe Lys Gly Lys Ala Thr Phe Thr Ala Asp Thr Ser Ser Asn
                 85                  90                  95

Thr Ala Asn Met Gln Leu Ser Ser Leu Thr Ser Glu Asp Ser Ala Val
            100                 105                 110

Tyr Tyr Cys Ala Arg Phe Asp Gly Asn Tyr Gly Tyr Tyr Ala Met Asp
            115                 120                 125

Tyr Trp Gly Gln Gly Ser Ser Val Thr Val Ser Ala Lys Thr Thr
        130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr
            180

<210> SEQ ID NO 13
<211> LENGTH: 363
<212> TYPE: DNA
<213> ORGANISM: Mus musculus
<220> FEATURE:
<223> OTHER INFORMATION: 52M51 Heavy chain variable region
      polynucleotide sequence without putative signal sequence

<400> SEQUENCE: 13
caggttcagc tgcagcagtc tggagctgag ctgatgaagc ctggggcctc agtgaagata     60
tcctgcaagg ctgctggcta cacaatgaga ggctactgga tagagtggat aaagcagagg    120
cctggacatg gccttgagtg gattggacag attttacctg gaactgggag aactaactac    180
aatgagaagt tcaagggcaa ggccacattc actgcagata catcctccaa cacagccaac    240
atgcaactca gcagcctgac atctgaggac tctgccgtct attactgtgc aagatttgat    300
ggtaactacg gttactatgc tatggactac tggggtcaag gatcctcagt caccgtctcc    360
tca                                                                   363

<210> SEQ ID NO 14
<211> LENGTH: 122
<212> TYPE: PRT
<213> ORGANISM: Mus musculus
<220> FEATURE:
<223> OTHER INFORMATION: 52M51 Heavy chain variable region amino acid
      sequence without putative signal sequence

<400> SEQUENCE: 14

Gln Val Gln Leu Gln Gln Ser Gly Ala Glu Leu Met Lys Pro Gly Ala
 1               5                  10                  15

Ser Val Lys Ile Ser Cys Lys Ala Ala Gly Tyr Thr Met Arg Gly Tyr
            20                  25                  30

Trp Ile Glu Trp Ile Lys Gln Arg Pro Gly His Gly Leu Glu Trp Ile
        35                  40                  45

Gly Gln Ile Leu Pro Gly Thr Gly Arg Thr Asn Tyr Asn Glu Lys Phe
     50                  55                  60

Lys Gly Lys Ala Thr Phe Thr Ala Asp Thr Ser Ser Asn Thr Ala Asn
 65                  70                  75                  80

```
Met Gln Leu Ser Ser Leu Thr Ser Glu Asp Ser Ala Val Tyr Tyr Cys
            85                  90                  95

Ala Arg Phe Asp Gly Asn Tyr Gly Tyr Tyr Ala Met Asp Tyr Trp Gly
        100                 105                 110

Gln Gly Ser Ser Val Thr Val Ser Ser Ala
        115                 120

<210> SEQ ID NO 15
<211> LENGTH: 6
<212> TYPE: PRT
<213> ORGANISM: Mus musculus
<220> FEATURE:
<223> OTHER INFORMATION: 52M51 Heavy chain CDR1

<400> SEQUENCE: 15

Arg Gly Tyr Trp Ile Glu
1               5

<210> SEQ ID NO 16
<211> LENGTH: 17
<212> TYPE: PRT
<213> ORGANISM: Mus musculus
<220> FEATURE:
<223> OTHER INFORMATION: 52M51 Heavy chain CDR2

<400> SEQUENCE: 16

Gln Ile Leu Pro Gly Thr Gly Arg Thr Asn Tyr Asn Glu Lys Phe Lys
1               5                   10                  15

Gly

<210> SEQ ID NO 17
<211> LENGTH: 12
<212> TYPE: PRT
<213> ORGANISM: Mus musculus
<220> FEATURE:
<223> OTHER INFORMATION: 52M51 Heavy chain CDR3

<400> SEQUENCE: 17

Phe Asp Gly Asn Tyr Gly Tyr Tyr Ala Met Asp Tyr
1               5                   10

<210> SEQ ID NO 18
<211> LENGTH: 14
<212> TYPE: PRT
<213> ORGANISM: Mus musculus
<220> FEATURE:
<223> OTHER INFORMATION: 52M51 Light chain CDR1

<400> SEQUENCE: 18

Arg Ser Ser Thr Gly Ala Val Thr Thr Ser Asn Tyr Ala Asn
1               5                   10

<210> SEQ ID NO 19
<211> LENGTH: 7
<212> TYPE: PRT
<213> ORGANISM: Mus musculus
<220> FEATURE:
<223> OTHER INFORMATION: 52M51 Light chain CDR2

<400> SEQUENCE: 19

Gly Thr Asn Asn Arg Ala Pro
1               5

<210> SEQ ID NO 20
<211> LENGTH: 16
```

```
<212> TYPE: PRT
<213> ORGANISM: Mus musculus
<220> FEATURE:
<223> OTHER INFORMATION: 52M51 Light chain CDR3

<400> SEQUENCE: 20

Ala Leu Trp Tyr Ser Asn His Trp Val Phe Gly Gly Gly Thr Lys Leu
1               5                   10                  15

<210> SEQ ID NO 21
<211> LENGTH: 1401
<212> TYPE: DNA
<213> ORGANISM: Artificial Sequence
<220> FEATURE:
<223> OTHER INFORMATION: 52M51-H4 Heavy chain polynucleotide sequence

<400> SEQUENCE: 21
atggattgga catggagggt gttctgcctc ctcgctgtgg ctcctggagt cctgagccag      60
gtccagctcg tccagagcgg ggctgaagtc aagaagcctg gcgctagcgt caaaatcagc     120
tgtaaggtca gcggatacac actgagggga tactggatcg agtgggtgag gcaggctcca     180
ggaaagggcc tggaatggat cggccagatc ctgcctggaa ccggaaggac aaattacaat     240
gagaagttta gggaagggt cacaatgaca gcagacacaa gcacagacac agcttatatg      300
gaactcagct ccctcagatc cgaggacacc gctgtctact attgtgccag gttcgatgga     360
aattacggat actatgccat ggattactgg ggacagggga caacggtcac cgtgagctca     420
gccagcacaa agggccctag cgtcttccct ctggctccct gcagcaggag caccagcgag     480
agcacagccg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggacccctga ggtcacgtgc     840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagccccc atcgagaaaa ccatctccaa aaccaaaggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401

<210> SEQ ID NO 22
<211> LENGTH: 466
<212> TYPE: PRT
<213> ORGANISM: Artificial Sequence
<220> FEATURE:
<223> OTHER INFORMATION: 52M51 H4 Heavy chain amino acid sequence

<400> SEQUENCE: 22

Met Asp Trp Thr Trp Arg Val Phe Cys Leu Leu Ala Val Ala Pro Gly
```

```
  1               5                   10                  15
Val Leu Ser Gln Val Gln Leu Val Gln Ser Gly Ala Glu Val Lys Lys
             20                  25                  30
Pro Gly Ala Ser Val Lys Ile Ser Cys Lys Val Ser Gly Tyr Thr Leu
             35                  40                  45
Arg Gly Tyr Trp Ile Glu Trp Val Arg Gln Ala Pro Gly Lys Gly Leu
             50                  55                  60
Glu Trp Ile Gly Gln Ile Leu Pro Gly Thr Gly Arg Thr Asn Tyr Asn
 65                  70                  75                  80
Glu Lys Phe Lys Gly Arg Val Thr Met Thr Ala Asp Thr Ser Thr Asp
             85                  90                  95
Thr Ala Tyr Met Glu Leu Ser Ser Leu Arg Ser Glu Asp Thr Ala Val
             100                 105                 110
Tyr Tyr Cys Ala Arg Phe Asp Gly Asn Tyr Gly Tyr Tyr Ala Met Asp
             115                 120                 125
Tyr Trp Gly Gln Gly Thr Thr Val Thr Val Ser Ser Ala Ser Thr Lys
 130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
             165                 170                 175
Val Thr Val Ser Trp Asn Ser Gly Ala Leu Thr Ser Gly Val His Thr
             180                 185                 190
Phe Pro Ala Val Leu Gln Ser Ser Gly Leu Tyr Ser Leu Ser Ser Val
             195                 200                 205
Val Thr Val Pro Ser Ser Asn Phe Gly Thr Gln Thr Tyr Thr Cys Asn
 210                 215                 220
Val Asp His Lys Pro Ser Asn Thr Lys Val Asp Lys Thr Val Glu Arg
225                 230                 235                 240
Lys Cys Cys Val Glu Cys Pro Pro Cys Pro Ala Pro Pro Val Ala Gly
             245                 250                 255
Pro Ser Val Phe Leu Phe Pro Pro Lys Pro Lys Asp Thr Leu Met Ile
             260                 265                 270
Ser Arg Thr Pro Glu Val Thr Cys Val Val Val Asp Val Ser His Glu
             275                 280                 285
Asp Pro Glu Val Gln Phe Asn Trp Tyr Val Asp Gly Val Glu Val His
 290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
             325                 330                 335
Glu Tyr Lys Cys Lys Val Ser Asn Lys Gly Leu Pro Ala Pro Ile Glu
             340                 345                 350
Lys Thr Ile Ser Lys Thr Lys Gly Gln Pro Arg Glu Pro Gln Val Tyr
             355                 360                 365
Thr Leu Pro Pro Ser Arg Glu Glu Met Thr Lys Asn Gln Val Ser Leu
             370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
             405                 410                 415
Leu Asp Ser Asp Gly Ser Phe Phe Leu Tyr Ser Lys Leu Thr Val Asp
             420                 425                 430
```

-continued

```
Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 23
<211> LENGTH: 141
<212> TYPE: PRT
<213> ORGANISM: Artificial Sequence
<220> FEATURE:
<223> OTHER INFORMATION: 52M51-H4  Heavy chain variable region amino
      acid sequence

<400> SEQUENCE: 23

Met Asp Trp Thr Trp Arg Val Phe Cys Leu Leu Ala Val Ala Pro Gly
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Val Ser Gly Tyr Thr Leu
        35                  40                  45

Arg Gly Tyr Trp Ile Glu Trp Val Arg Gln Ala Pro Gly Lys Gly Leu
    50                  55                  60

Glu Trp Ile Gly Gln Ile Leu Pro Gly Thr Gly Arg Thr Asn Tyr Asn
65                  70                  75                  80

Glu Lys Phe Lys Gly Arg Val Thr Met Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Arg Phe Asp Gly Asn Tyr Gly Tyr Tyr Ala Met Asp
        115                 120                 125

Tyr Trp Gly Gln Gly Thr Thr Val Thr Val Ser Ser Ala
    130                 135                 140

<210> SEQ ID NO 24
<211> LENGTH: 122
<212> TYPE: PRT
<213> ORGANISM: Artificial Sequence
<220> FEATURE:
<223> OTHER INFORMATION: 52M51-H4  Heavy chain variable region amino
      acid sequence without putative signal sequence

<400> SEQUENCE: 24

Gln Val Gln Leu Val Gln Ser Gly Ala Glu Val Lys Lys Pro Gly Ala
1               5                   10                  15

Ser Val Lys Ile Ser Cys Lys Val Ser Gly Tyr Thr Leu Arg Gly Tyr
            20                  25                  30

Trp Ile Glu Trp Val Arg Gln Ala Pro Gly Lys Gly Leu Glu Trp Ile
        35                  40                  45

Gly Gln Ile Leu Pro Gly Thr Gly Arg Thr Asn Tyr Asn Glu Lys Phe
    50                  55                  60

Lys Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Asp Gly Asn Tyr Gly Tyr Tyr Ala Met Asp Tyr Trp Gly
            100                 105                 110
```

Gln Gly Thr Thr Val Thr Val Ser Ser Ala
        115                 120

<210> SEQ ID NO 25
<211> LENGTH: 720
<212> TYPE: DNA
<213> ORGANISM: Artificial Sequence
<220> FEATURE:
<223> OTHER INFORMATION: 52M51-L3 Light chain polynucleotide sequence

<400> SEQUENCE: 25

```
atgagcgtcc ctacaatggc ttggatgatg ctcctgctgg gactcctggc ttatggaagc      60
ggagtggata gccaggccgt cgtcacacag gaacctagcc tcaccgttag ccctggagga     120
acagtcacac tgacctgtag gagctccaca ggagctgtga caacaagcaa ttacgctaac     180
tggttccagc agaagcccgg tcaagcccct agaaccctca tcggcggcac caataacaga     240
gctcccggag tccccgccag gttctccggc tccctcctgg gtggcaaggc tgctctgaca     300
ctcagcggtg cccagccaga ggatgaagcg gagtactact gtgcactgtg gtacagcaac     360
cattgggttt tcggaggcgg aacaaagtta accgtcctcg gcagcctaa ggctgctcct      420 agcgtcacac tgttcccccc atctagcgag gagctgcagg ctaacaaggc aaccctcgtc     480
tgcctggtta gcgacttcta ccctggcgct gtcacagtgg cctggaaagc tgacggctcc     540
cctgtgaaag ttggcgtcga aaccacaaag ccttctaagc agagcaataa taaatatgcc     600
gcaagctcct acctctccct gactcctgag cagtggaaaa gccataggag ctactcctgc     660
cgggtcacac acgaaggaag cacagtggaa aagacagtcg cccctgctga gtgtagctga     720
```

<210> SEQ ID NO 26
<211> LENGTH: 239
<212> TYPE: PRT
<213> ORGANISM: Artificial Sequence
<220> FEATURE:
<223> OTHER INFORMATION: 52M51-L3 Light chain amino acid sequence

<400> SEQUENCE: 26

Met Ser Val Pro Thr Met Ala Trp Met Met Leu Leu Gly Leu Leu
1               5                   10                  15

Ala Tyr Gly Ser Gly Val Asp Ser Gln Ala Val Val Thr Gln Glu Pro
            20                  25                  30

Ser Leu Thr Val Ser Pro Gly Gly Thr Val Thr Leu Thr Cys Arg Ser
        35                  40                  45

Ser Thr Gly Ala Val Thr Thr Ser Asn Tyr Ala Asn Trp Phe Gln Gln
    50                  55                  60

Lys Pro Gly Gln Ala Pro Arg Thr Leu Ile Gly Gly Thr Asn Asn Arg
65                  70                  75                  80

Ala Pro Gly Val Pro Ala Arg Phe Ser Gly Ser Leu Leu Gly Gly Lys
                85                  90                  95

Ala Ala Leu Thr Leu Ser Gly Ala Gln Pro Glu Asp Glu Ala Glu Tyr
            100                 105                 110

Tyr Cys Ala Leu Trp Tyr Ser Asn His Trp Val Phe Gly Gly Gly Thr
        115                 120                 125

Lys Leu Thr Val Leu Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Val Ser Asp Phe Tyr Pro Gly Ala Val Thr Val Ala Trp Lys

```
                       165                 170                 175
Ala Asp Gly Ser Pro Val Lys Val Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Arg Val Thr His
    210                 215                 220

Glu Gly Ser Thr Val Glu Lys Thr Val Ala Pro Ala Glu Cys Ser
225                 230                 235

<210> SEQ ID NO 27
<211> LENGTH: 134
<212> TYPE: PRT
<213> ORGANISM: Artificial Sequence
<220> FEATURE:
<223> OTHER INFORMATION: 52M51-L3 Light chain variable region amino acid
      sequence

<400> SEQUENCE: 27

Met Ser Val Pro Thr Met Ala Trp Met Met Leu Leu Leu Gly Leu Leu
1               5                   10                  15

Ala Tyr Gly Ser Gly Val Asp Ser Gln Ala Val Val Thr Gln Glu Pro
            20                  25                  30

Ser Leu Thr Val Ser Pro Gly Gly Thr Val Thr Leu Thr Cys Arg Ser
        35                  40                  45

Ser Thr Gly Ala Val Thr Thr Ser Asn Tyr Ala Asn Trp Phe Gln Gln
    50                  55                  60

Lys Pro Gly Gln Ala Pro Arg Thr Leu Ile Gly Gly Thr Asn Asn Arg
65                  70                  75                  80

Ala Pro Gly Val Pro Ala Arg Phe Ser Gly Ser Leu Leu Gly Gly Lys
                85                  90                  95

Ala Ala Leu Thr Leu Ser Gly Ala Gln Pro Glu Asp Glu Ala Glu Tyr
            100                 105                 110

Tyr Cys Ala Leu Trp Tyr Ser Asn His Trp Val Phe Gly Gly Gly Thr
        115                 120                 125

Lys Leu Thr Val Leu Gly
        130

<210> SEQ ID NO 28
<211> LENGTH: 115
<212> TYPE: PRT
<213> ORGANISM: Artificial Sequence
<220> FEATURE:
<223> OTHER INFORMATION: 52M51-L3 Light chain variable region amino acid
      sequence without putative signal sequence

<400> SEQUENCE: 28

Ser Gly Val Asp Ser Gln Ala Val Val Thr Gln Glu Pro Ser Leu Thr
1               5                   10                  15

Val Ser Pro Gly Gly Thr Val Thr Leu Thr Cys Arg Ser Ser Thr Gly
            20                  25                  30

Ala Val Thr Thr Ser Asn Tyr Ala Asn Trp Phe Gln Gln Lys Pro Gly
        35                  40                  45

Gln Ala Pro Arg Thr Leu Ile Gly Gly Thr Asn Asn Arg Ala Pro Gly
    50                  55                  60

Val Pro Ala Arg Phe Ser Gly Ser Leu Leu Gly Gly Lys Ala Ala Leu
65                  70                  75                  80

Thr Leu Ser Gly Ala Gln Pro Glu Asp Glu Ala Glu Tyr Tyr Cys Ala
```

85                  90                  95
Leu Trp Tyr Ser Asn His Trp Val Phe Gly Gly Gly Thr Lys Leu Thr
                100                 105                 110

Val Leu Gly
        115

<210> SEQ ID NO 29
<211> LENGTH: 720
<212> TYPE: DNA
<213> ORGANISM: Artificial Sequence
<220> FEATURE:
<223> OTHER INFORMATION: 52M51-L4 Light chain polynucleotide sequence

<400> SEQUENCE: 29

```
atgagcgtcc ctacaatggc ttggatgatg ctcctgctgg gactcctggc ttatggaagc    60
ggagtggata gccagaccgt cgtcacacag gaacctagct tttccgttag ccctggagga   120
acagtcacac tgacctgtag agctccacag ggagctgtga caacaagcaa ttacgctaac   180
tggtatcagc agactcccgg tcaagcccct agaaccctca tcggcggcac caataacaga   240
gctcccggag tccccgacag gttctccggc tccatcctgg gaaataaagc tgctctgaca   300
atcacaggtg cccaggctga cgatgaaagc gactactact gtgcactgtg gtacagcaac   360
cattgggttt tcggaggcgg aacaaagtta accgtcctcg gcagcctaa ggctgctcct   420
agcgtcacac tgttccccc atctagcgag gagctgcagg ctaacaaggc aaccctcgtc   480
tgcctggtta gcgacttcta ccctggcgct gtcacagtgg cctggaaagc tgacggctcc   540
cctgtgaaag ttggcgtcga aaccacaaag ccttctaagc agagcaataa taaatatgcc   600
gcaagctcct acctctccct gactcctgag cagtggaaaa gccataggag ctactcctgc   660
cgggtcacac acgaaggaag cacagtggaa aagacagtcg cccctgctga gtgtagctga   720
```

<210> SEQ ID NO 30
<211> LENGTH: 239
<212> TYPE: PRT
<213> ORGANISM: Artificial Sequence
<220> FEATURE:
<223> OTHER INFORMATION: 52M51-L4 Light chain amino acid sequence

<400> SEQUENCE: 30

Met Ser Val Pro Thr Met Ala Trp Met Met Leu Leu Leu Gly Leu Leu
1               5                   10                  15

Ala Tyr Gly Ser Gly Val Asp Ser Gln Thr Val Val Thr Gln Glu Pro
                20                  25                  30

Ser Phe Ser Val Ser Pro Gly Gly Thr Val Thr Leu Thr Cys Arg Ser
            35                  40                  45

Ser Thr Gly Ala Val Thr Thr Ser Asn Tyr Ala Asn Trp Tyr Gln Gln
        50                  55                  60

Thr Pro Gly Gln Ala Pro Arg Thr Leu Ile Gly Gly Thr Asn Asn Arg
65                  70                  75                  80

Ala Pro Gly Val Pro Asp Arg Phe Ser Gly Ser Ile Leu Gly Asn Lys
                85                  90                  95

Ala Ala Leu Thr Ile Thr Gly Ala Gln Ala Asp Asp Glu Ser Asp Tyr
            100                 105                 110

Tyr Cys Ala Leu Trp Tyr Ser Asn His Trp Val Phe Gly Gly Gly Thr
        115                 120                 125

Lys Leu Thr Val Leu Gly Gln Pro Lys Ala Ala Pro Ser Val Thr Leu
    130                 135                 140

```
Phe Pro Pro Ser Ser Glu Glu Leu Gln Ala Asn Lys Ala Thr Leu Val
145                 150                 155                 160

Cys Leu Val Ser Asp Phe Tyr Pro Gly Ala Val Thr Val Ala Trp Lys
            165                 170                 175

Ala Asp Gly Ser Pro Val Lys Val Gly Val Glu Thr Thr Lys Pro Ser
        180                 185                 190

Lys Gln Ser Asn Asn Lys Tyr Ala Ala Ser Ser Tyr Leu Ser Leu Thr
    195                 200                 205

Pro Glu Gln Trp Lys Ser His Arg Ser Tyr Ser Cys Arg Val Thr His
210                 215                 220

Glu Gly Ser Thr Val Glu Lys Thr Val Ala Pro Ala Glu Cys Ser
225                 230                 235

<210> SEQ ID NO 31
<211> LENGTH: 134
<212> TYPE: PRT
<213> ORGANISM: Artificial Sequence
<220> FEATURE:
<223> OTHER INFORMATION: 52M51-L4 Light chain variable region amino acid
      sequence

<400> SEQUENCE: 31

Met Ser Val Pro Thr Met Ala Trp Met Met Leu Leu Leu Gly Leu Leu
1               5                   10                  15

Ala Tyr Gly Ser Gly Val Asp Ser Gln Thr Val Thr Gln Glu Pro
            20                  25                  30

Ser Phe Ser Val Ser Pro Gly Gly Thr Val Thr Leu Thr Cys Arg Ser
        35                  40                  45

Ser Thr Gly Ala Val Thr Thr Ser Asn Tyr Ala Asn Trp Tyr Gln Gln
    50                  55                  60

Thr Pro Gly Gln Ala Pro Arg Thr Leu Ile Gly Gly Thr Asn Asn Arg
65                  70                  75                  80

Ala Pro Gly Val Pro Asp Arg Phe Ser Gly Ser Ile Leu Gly Asn Lys
                85                  90                  95

Ala Ala Leu Thr Ile Thr Gly Ala Gln Ala Asp Asp Glu Ser Asp Tyr
            100                 105                 110

Tyr Cys Ala Leu Trp Tyr Ser Asn His Trp Val Phe Gly Gly Gly Thr
        115                 120                 125

Lys Leu Thr Val Leu Gly
        130

<210> SEQ ID NO 32
<211> LENGTH: 115
<212> TYPE: PRT
<213> ORGANISM: Artificial Sequence
<220> FEATURE:
<223> OTHER INFORMATION: 52M51-L4  Light chain variable region amino
      acid sequence without putative signal sequence

<400> SEQUENCE: 32

Ser Gly Val Asp Ser Gln Thr Val Thr Gln Glu Pro Ser Phe Ser
1               5                   10                  15

Val Ser Pro Gly Gly Thr Val Thr Leu Thr Cys Arg Ser Ser Thr Gly
            20                  25                  30

Ala Val Thr Thr Ser Asn Tyr Ala Asn Trp Tyr Gln Gln Thr Pro Gly
        35                  40                  45

Gln Ala Pro Arg Thr Leu Ile Gly Gly Thr Asn Asn Arg Ala Pro Gly
    50                  55                  60
```

```
Val Pro Asp Arg Phe Ser Gly Ser Ile Leu Gly Asn Lys Ala Ala Leu
 65              70                  75                  80

Thr Ile Thr Gly Ala Gln Ala Asp Asp Glu Ser Asp Tyr Tyr Cys Ala
                 85                  90                  95

Leu Trp Tyr Ser Asn His Trp Val Phe Gly Gly Gly Thr Lys Leu Thr
                100                 105                 110

Val Leu Gly
        115

<210> SEQ ID NO 33
<211> LENGTH: 7
<212> TYPE: PRT
<213> ORGANISM: Artificial Sequence
<220> FEATURE:
<223> OTHER INFORMATION: FLAG-tag

<400> SEQUENCE: 33

Asp Tyr Lys Asp Asp Asp Lys
1               5
```

What is claimed is:

1. A method of treating a hematologic cancer in a human subject comprising administering to the subject a therapeutically effective amount of an antibody that specifically binds human Notch1, wherein the hematologic cancer is selected from the rout of acute myelogenous leukemia, Hodgkin lymphoma, multiple myeloma, and T-cell acute lymphoblastic leukemia, and wherein the antibody comprises:
   (a) a heavy chain CDR1 comprising RGYWIE (SEQ ID NO:15); a heavy chain CDR2 comprising QILPGTGRT-NYNEKFKG (SEQ ID NO:16); and a heavy chain CDR3 comprising FDGNYGYYAMDY (SEQ ID NO:17); and
   (b) a light chain CDR1 comprising RSSTGAVTTSNYAN (SEQ ID NO:18); a light chain CDR2 comprising GTNNRAP (SEQ ID NO:19); and a light chain CDR3 comprising ALWYSNHWVFGGGTKL (SEQ ID NO:20).

2. The method of claim 1, wherein the antibody comprises:
   (a) a heavy chain variable region comprising an amino acid sequence selected from the group consisting of SEQ ID NO:14 and SEQ ID NO:24; and
   (b) a light chain variable region comprising an amino acid sequence selected from the group consisting of SEQ ID NO:8, SEQ ID NO:28, and SEQ ID NO:32.

3. The method of claim 1, wherein the antibody is a recombinant antibody, a monoclonal antibody, a chimeric antibody, a humanized antibody, an antigen-binding antibody fragment a bispecific antibody, a monospecific antibody, a monovalent antibody, an IgG1 antibody, or an IgG2 antibody.

4. The method of claim 1, wherein the antibody is the antibody encoded by the plasmid deposited with the ATCC as Patent Deposit PTA-9549.

5. The method of claim 1, wherein the hematologic cancer is T-cell acute lymphoblastic leukemia.

6. The method, of claim 1, which further comprises administering at least one additional therapeutic agent.

7. The method of claim 6, wherein the additional therapeutic agent is a chemotherapeutic agent.

8. The method of claim 6, wherein the antibody is administered with radiation therapy, and/or after radiation therapy.

9. The method of claim 1, wherein the antibody comprises:
   (a) a heavy chain variable region comprising the amino acid sequence of SEQ ID NO:24; and
   (b) a light chain variable region comprising the amino acid sequence of SEQ ID NO:28.

10. The method of claim 3, wherein the antibody is a monoclonal antibody.

11. The method of claim 3, wherein the antibody is an IgG2 antibody.

* * * * *

UNITED STATES PATENT AND TRADEMARK OFFICE
CERTIFICATE OF CORRECTION

PATENT NO. : 8,834,875 B2
APPLICATION NO. : 13/005966
DATED : September 16, 2014
INVENTOR(S) : Edward Thein Htun Van Der Horst Page 1 of 1

It is certified that error appears in the above-identified patent and that said Letters Patent is hereby corrected as shown below:

IN THE CLAIMS:

Column 97, Line 30, please change "rout" to --group consisting--.

Signed and Sealed this
Twenty-fourth Day of February, 2015

Michelle K. Lee
*Deputy Director of the United States Patent and Trademark Office*